US006436691B1

(12) United States Patent
Slater et al.

(10) Patent No.: US 6,436,691 B1
(45) Date of Patent: Aug. 20, 2002

(54) CHEMICAL COMPOUNDS

(75) Inventors: Anthony Michael Slater; David Charles Blakey; David Huw Davies; John Frederick Hennam, all of Macclesfield (GB); Laurent Francois Andre Hennequin, Reims Cedex (FR); Peter Robert Marsham; Robert Ian Dowell, both of Macclesfield (GB)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 09/011,769

(22) PCT Filed: Aug. 13, 1996

(86) PCT No.: PCT/GB96/01975
§ 371 (c)(1),
(2), (4) Date: Feb. 13, 1998

(87) PCT Pub. No.: WO97/07769
PCT Pub. Date: Mar. 6, 1997

(30) Foreign Application Priority Data

Aug. 16, 1995 (GB) ................................. 9516810
May 25, 1996 (GB) ................................. 9611019
Jun. 12, 1996 (GB) ................................. 9612295

(51) Int. Cl.[7] ..................... C12N 9/64; C12N 15/57; C12N 15/62; A61K 39/395; A61K 38/48

(52) U.S. Cl. ................... 435/226; 435/69.1; 435/252.3; 435/320.1; 435/471; 435/69.7; 530/387.1; 424/94.63; 424/178.1; 514/2; 536/23.2; 536/23.4

(58) Field of Search ................ 435/226, 471, 435/252.3, 320.1; 424/178.1, 182.1, 1.17, 1.1; 514/12; 530/391.1, 391.7; 536/23.2, 23.4; 562/11

(56) References Cited

U.S. PATENT DOCUMENTS

| 4,364,934 A | 12/1982 | Drayna et al. ......... 530/388.75 |
| 4,650,762 A | * 3/1987 | Boross et al. ............... 435/180 |
| 4,975,278 A | 12/1990 | Senter et al. ............ 424/178.1 |

(List continued on next page.)

FOREIGN PATENT DOCUMENTS

| WO | WO 88/07378 | 10/1988 |
| WO | WO 89/10140 | 11/1989 |
| WO | WO 90/07929 | 7/1990 |

(List continued on next page.)

OTHER PUBLICATIONS

Graf et al., Selective Alteration of Substrate Specificity by Replacement of Aspartic Acid–189 with Lysine in the Binding Pocket of Trypsin, Biochemistry, 1987 vol. 26, 261–62623.

(List continued on next page.)

*Primary Examiner*—Ponnathapu Achutamurthy
(74) *Attorney, Agent, or Firm*—Morgan, Lewis & Bockius LLP

(57) ABSTRACT

Antibody Directed Enzyme Prodrug Therapy (ADEPT) systems for use in cancer based on mutated carboxypeptidase B (CPB) enzymes. Enzyme conjugates for ADEPT are substantially non-immunogenic in humans comprising a targeting moiety (for example an antibody) capable of binding with a tumor associated antigen, the targeting moiety being linked to a mutated form of a CPB enzyme capable of converting a prodrug into an antineoplastic drug wherein the prodrug is not significantly convertible into antineoplastic drug in humans by natural unmutated enzyme. A preferred enzyme mutant is human pancreatic CPB comprising a Lys or Arg residue at position 253. Suitable mustard prodrugs are disclosed in the specification.

18 Claims, 17 Drawing Sheets

U.S. PATENT DOCUMENTS

| | | | |
|---|---|---|---|
| 5,389,537 A | | 2/1995 | Raines et al. ............... 435/199 |
| 5,433,955 A | | 7/1995 | Bredehorst et al. ......... 424/94.3 |
| 5,593,674 A | * | 1/1997 | Drayna et al. ............... 435/221 |
| 5,632,990 A | | 5/1997 | Bagshawe et al. ........ 424/178.1 |
| 5,837,516 A | * | 11/1998 | Ballinger et al. ........... 435/221 |
| 5,945,329 A | * | 8/1999 | Breddam et al. ........... 435/223 |
| 5,948,668 A | * | 9/1999 | Hartman et al. ............. 435/212 |
| 5,985,281 A | * | 11/1999 | Taylorson et al. ........ 424/178.1 |
| 5,985,627 A | * | 11/1999 | Mortensen et al. ......... 435/129 |
| 6,140,100 A | * | 10/2000 | Smith et al. ................. 435/226 |

FOREIGN PATENT DOCUMENTS

| | | |
|---|---|---|
| WO | WO 93/15208 | 8/1993 |
| WO | WO 95/13095 | 5/1995 |
| WO | WO 96/20011 | 7/1996 |
| WO | WO 96/23064 | 8/1996 |
| WO | WO 97/07769 | 3/1997 |

OTHER PUBLICATIONS

Soman et al., Electrical Potentials in Trypsin Isozymes, Biochemistry, 1989 vol. 28, 9918–9926.

McGrath et al., Structure of an Engineered, Metal–Actuated Switch in Trypsin, Biochemistry, 1993 vol. 32, 1914–1919.

Tsu et al., Structured Basis for the Broad Substrate Specificity of Fiddler Crab Collagenolytic Serine Protease 1, Biochemistry, 1997 vol. 36, 5393–501.

Sprang et al., Studies of Specificity and Catalysis in Trypsin by Structural Analysis of Site–Directed Mutants, CRC Critical Reviews in Biotechnology, 1988 vol. 8, Issue 3, 225–236.

Bone et al., Mutation Remodeling of Enzyme Specificity, Methods in Enzymology, 1991, vol. 202, 643,671.

Craik et al., Redesigning Trypsin Via Genetic Engineerng, Journal of Cellular Biochemistry, 1987 vol. 33, 199–211.

Wilke et al., Crystal Structure of Rat Trpsin–S195C at –150°–Analysis of Low Activity of Recombinant and Semisynthetic Thio Proteases, Journal of Molecular Biology, 1991 vol. 219, 511–523.

Wilke et al., Crystallographic Analysis of Trypsin–G226A—A Specificity Pocket Mutant of Rat Trypsin with Altered Binding and Catalysis, Journal of Molecular Biology, 1991 vol. 219, 525–532.

Perona et al., Relocating a Negative Charge in the Binding Pocket of Trypsin, Journal of Molecular Biology, 1993 vol. 230, 934,949.

Craik et al., Redesigning Trypsin: Alteration of Substrate Specificity, Science, Apr. 1985, vol.228 291–297.

Sprang et al., The Three–Dimensional Structure of $Asn^{102}$ Mutant of Trypsin: Role of $Asp^{102}$ in Serine Protease Catalysis Aug. 1997, Science vol. 237 905–909.

Phillips et al., Transition–State Characterization: A new Approach Combining Inhibitor Analogues and Variation in Enzyme Structure, Biochemistry, 1992, vol. 31 959–963.

Kuefner et al., Carboxypeptidase–Mediated Release of Methotrexate from Methotrexate α–Peptides, Biochemistry, 1989, vol. 28 2288–2297.

Hwang et al., Why ion pair reversal by protein engineering is unlikely to suceed, Nature, Jul 1988, vol. 334 270–272.

Rectenwald et al. Protein Engineering and design—Method and industrial relevance, Journal of Biotechnology, 1993, vol. 28 1–23.

Wells et al., Designing substrate specificity by protein engineering of electrostatic interactions, Proc. Natl. Acad. Sci. USA, Mar. 1987, vol. 84 1219–1223.

Olesen et al., Altering substrate preference of carboxypeptidase Y by a novel strategy of mutagenesis eliminating wild type background. Protein Entineering. 1993, vol. 6 409–415.

Teragona–Fiol, et al., Identification by site–directed mutagenesis of amino acids in the B2 subsite of bovine pancreatic ribonuclease A, Protein Engineering, 1993, vol. 6 901–906.

Lesk et al., Antibody Structure and Structural Predictions Useful in Guiding Antibody Engineering, Antibody Engineering, 1992–pp. 1–38.

Bosslet et al., Tumor–selective prodrug activation by fusion protein–mediated catalysis, Cancer Research, vol. 54, Apr. 15, 1994, pp. 2151–2159, XP002000814 cited in the application, see p. 2151, col. 1, para. 1,see p 2151, col. 2, para. 2.

Vitols et al., Methotrexate–α–Phenylalanine: Optimization of Methtrexate Prodrug for Activation by Carboxypeptidase A–Monocolonal Antibody Conjugate[1], Cancer Research, Feb. 1995, vol 55 pp. 478–481.

Faming et al., Structural Evolution of an Enzyme Specificity, The Structure of Rat Carboxypeptidase A2 at 1.9Å Resolution, Journal of Biological Chemistry, Dec. 1991, vol. 266 pp. 24606–24612.

Davies et al, A novel bisiodo–phenol mustard prodrug, ZD2767P for antibody–directed enzyme prodrug therapy, Data Biosis Biosciences Information Services, AN=95:187056, XP002000815, see abstract & 86th Annual Meeting of the Americ. Assoc. For Cancer Res. & Proceedings of the Americ. Assoc. For Cancer Res. Annual Meting, vol. 36, No. 0, Mar. 18–22, 1995, p. 482.

Wallace et al, Invitro and in vivo activities of monoclonal antibody–alkaline phosphatase conjugates in combination with phenol mustard phosphate, Bioconjugate Chemistry, vol. 2, No. 5, Sep. 1, 1991, 349–352.

Kim et al., Crystal Structure of the Complex of Carboxypeptidase A with a Strongly Bound Phosphonate in a New Crystalline Form: Comparison with Structures of Other Complexes, Biochemistry, 1990, vol. 29 5546–5555.

Eaton et al., Isolation, Molecular Cloning, and partial Characterization of a Novel Carboxypeptidase B from Human Plasma, The Journal of Biological Chemistry, Nov. 1991, vol. 266 21833–21838.

Yamamoto et al., Isolation of a cDNA Encoding a Human Serum Marker for Acute Pancreatitis, Identification of Pancreas–Specific Protein As Pancreatic Procarboxypeptidase B*, The Journal of Biological Chemistry, Feb. 1992, vol. 267. 2575–2581 (vol. 267).

Abstract #3188, Miller et al, Mutant human carboxypetpidase A1 and A2 (CPA1 and CPA2) for use in anbobody–directed enzyme prodrug therapy (ADEPT) of solid tumors: optimization of mutated active site substrate specificity, Proceedings of the American Assocation for Cancer Research, Mar. 1996, vol. 37 467.

* cited by examiner

Human Pancreatic Carboxypeptidase B

FIG. 4 pICI266 expression vector - gene cloning

```
TCACACTTTGCAAAGCATTAGCATTTTGTCCATAAGATAAGCGGATCCTGCCTGAGGGTTTTTGCCGGACTCTCTACTGTTTCTCCAT  1170
                                        PelB                                          NcoI

ACCTGTTTTTCTGGATGGAGTAAGACC ATGAAATACCTATTGCCTACGGCAGCCGCTGGATTGTTATTACTGCTGCCAACCAGCCATG  1260
                            MetLysTyrLeuLeuProThrAlaAlaAlaGlyLeuLeuLeuLeuLeuAlaAlaGlnProAlaMet
Insert gene
        KpnI    BglII       XbaI        XhoI    AsuII EcoRI
GCGGTACCAATAGACAGATCTAGATGTCTCTAGAGTTGTTACCTCGAGTTCGAAGAATTCCTAGAGTCGACATTATATTACTAATTAATTGGGG  1350
AlaValProIleAlaAspLeuMetSerLeuAspValThrSerSerSerLysAsnSer *
                                SphI ACCCTAGAGGTCCCCTTTTTTATTTTAAAAAGCATGCGGATCCGTCGGAAATACAGGAACGCACGCTGGATGGCCCTTGCTGGGATGGT  1440
```

FIG. 6
Growth medium

| Component | Concentration g/l deionised water |
|---|---|
| Potassium di-hydrogen orthophosphate | 3.0 |
| di-sodium hydrogen orthophosphate | 6.0 |
| Sodium chloride | 0.5 |
| Casein hydrolysate | 2.0 |
| Ammonium sulphate | 10.0 |
| Glycerol | 35.0 |
| Yeast extract | 20.0 |
| Magnesium sulphate heptahydrate | 0.5 |
| Calcium chloride di-hydrate | 0.03 |
| Thiamine | 0.008 |
| Iron sulphate heptahydrate | 0.04 |
| Citric acid | 0.02 |
| Trace element solution (TES)* | 0.5 ml/l |
| Tetracycline hydrochloride | 0.01 |

\* Trace element solution (TES)

| Component | mg per 10ml de-ionised water |
|---|---|
| Aluminium chloride hexahydrate | 2.0 |
| Cobalt chloride hexahydrate | 0.8 |
| Potassium chromium sulphate dodecahydrate | 0.2 |
| Copper chloride dihydrate | 0.2 |
| Boric acid | 0.1 |
| Potassium iodide | 2.0 |
| Manganese sulphate monohydrate | 2.0 |
| Nickel sulphate hexahydrate | 0.09 |
| Sodium molybdate dihydrate | 0.4 |
| Zinc sulphate heptahydrate | 0.4 |

CHEMICAL COMPOUNDS

The invention relates to mutant CPB enzymes for use with prodrugs in ADEPT systems.

| Abbreviations | |
|---|---|
| Ac | acetyl |
| ADEPT | antibody directed enzyme prodrug therapy |
| BOC | tert-butoxycarbonyl |
| CPB | carboxypeptidase B |
| DCCI | 1,3-dicyclohexylcarbodiimide |
| DMAP | 4-dimethylaminopyridine |
| DMF | N,N-dimethyl-formamide |
| DMSO | dimethylsulfoxide |
| Et | ethyl |
| EDCI | 1-(3-dimethylaminopropyl)-3-ethyl-carbodiimide |
| HCPB | human CPB |
| HOBT | 1-hydroxybenzotriazole |
| PCR | polymerase chain reaction |
| TFA | trifluoroacetic acid |
| THF | tetrahydrofuran |

Targeting of drugs selectively to kill cancer cells in a patient has long been a problem for medical research. ADEPT is one approach to overcome the problem. ADEPT uses a tumour selective agent such as an antibody conjugated to an enzyme. The conjugate is administered to the patient (usually intravenously), allowed to localise at the tumour site(s) and clear from the general circulation. Subsequently a prodrug is administered to the patient which is converted by the enzyme (localised at the tumour sites) into a cytotoxic drug which kills tumour cells. Since one molecule of enzyme can catalyse generation of many cytotoxic drug molecules an amplification effect is produced. Furthermore tumour cells not displaying the antigen recognised by the antibody (tumours usually display microheterogeneity) are also killed by enzymically amplified generation of the cytotoxic drug. A known system uses the procaryotic enzyme carboxypeptidase G2 (CPG2) as the enzyme component (see WO 88/07378).

A further problem with known systems is that repeated administration of the conjugate results in a host immune response rendering the therapy less effective. The antibody component is generally a mouse monclonal antibody which can be humanised using known techniques to reduce immunogenicity. However reduction of the immunogenicity of the enzyme component has proved more problematic. This is because the enzyme component must not be present naturally in the human host circulation otherwise premature conversion of prodrug to cytotoxic drug will occur and little selective toxicity to tumours will be observed.

These problems have been addressed in part by International Patent application WO 95/13095 (Wellcome Foundation). This application proposed ADEPT using mutant mammalian enzymes to activate prodrugs which are not activated by the corresponding native enzyme. However only ADEPT systems using mutants of carboxypeptidase A were enabled in the disclosure.

According to one aspect of the present invention there is provided a conjugate which is substantially non-immunogenic in humans comprising a targeting moiety capable of binding with a tumour associated antigen, the targeting moiety being linked to a mutated form of a carboxypeptidase B (CPB) enzyme capable of converting a prodrug into an antineoplastic drug wherein the prodrug is not significantly convertible into antineoplastic drug in humans by natural unmutated enzyme.

Preferably the targeting moiety is an antibody.

Preferably the antibody is a F(ab')2 antibody fragment.

Preferably the enzyme is mutated to comprise a polarity change in its active site such that it can turn over a prodrug with a complementary polarity.

Preferably the enzyme is any one of the following pancreatic human CPB mutants:

pancreatic human CPB having amino acid Asp 253 substituted by any one of Arg, Asn, Gln or Lys optionally in combination with any one or more amino acid substitutions selected from:

- natural amino acid Gln 54 substituted by any one of Arg, Lys or Asn;
- natural amino acid Asp 145 substituted by any one of Val, Leu, Ile or Ala;
- natural amino acid Ile 201 substituted by any one of Ser or Thr;
- natural amino acid Ser 205 substituted by any one of Asn, Gln, His, Lys or Arg;
- natural amino acid Ile 245 substituted by any one of Ser, Thr, Ala, Val, Leu, Asn, Gln, Lys, Arg or His;
- natural amino acid Ala 248 substituted by any one of Asn, Gln, Lys, Arg, His, Ser or Thr;
- natural amino acid Gly 251 substituted by any one of Thr, Asn, Ser, Gln, His, Lys, Arg, Val, Ile, Leu, Met, Phe, Ala or Norleucine; and
- natural amino acid Cys 288 substituted by any one of Ser, Thr, Ala, Val, Leu or Ile.

More preferably the enzyme is any one of the following pancreatic human CPB mutants:

pancreatic human CPB having natural amino acid Asp 253 substituted by any one of Arg or Lys and natural amino acid Gly 251 substituted by any one of Thr, Asn, Ser, Gln, Lys or Val, optionally in combination with any one or more amino acid substitutions selected from:

- natural amino acid Gln 54 substituted by Arg;
- natural amino acid Asp 145 substituted by Ala;
- natural amino acid Ile 201 substituted by Ser;
- natural amino acid Ser 205 substituted by Asn;
- natural amino acid Ile 245 substituted by any one of Ser, Ala or His;
- natural amino acid Ala 248 substituted by any one of His, Ser or Asn; and
- natural amino acid Cys 288 substituted by any one of Ser or Ala.

More preferably the enzyme is any one of the following pancreatic human CPB mutants:

pancreatic human CPB having natural amino acid Asp 253 substituted by any one of Arg or Lys and natural amino acid Gly 251 substituted by any one of Thr, Asn or Ser optionally in combination with any one or more amino acid substitutions selected from:

- natural amino acid Gln 54 substituted by Arg;
- natural amino acid Asp 145 substituted by Ala;
- natural amino acid Ile 201 substituted by Ser;
- natural amino acid Ser 205 substituted by Asn;
- natural amino acid lie 245 substituted by Ala;
- natural amino acid Ala 248 substituted by any one of Ser or Asn; and
- natural amino acid Cys 288 substituted by Ser.

Especially the enzyme is any one of the following pancreatic human CPB mutants:

D253K; D253R; [G251N, D253K]; [G251T, D253K]; [G251S, D253K]; [G251T, D253R]; [A248S,G251T, D253K]; [A248N,G251N,D253K]; [A248S,G251N, D253K]; or [S205N,G251N,D253K].

According to another aspect of the present invention there is provided a matched two component system designed for use in a host in which the components comprise:
(i) a first component that is a targeting moiety capable of binding with a tumour associated antigen, the targeting moiety being linked to a CPB enzyme capable of converting a prodrug into an antineoplastic drug and;
(ii) a second component that is a prodrug convertible under the influence of the enzyme to the antineoplastic drug;
wherein:
the enzyme is a mutated form of a CPB enzyme;
the first component is substantially non-immunogenic in the host and; the prodrug is not significantly convertible into antineoplastic drug in the host by natural unmutated host enzyme.

The term "the prodrug is not significantly convertible into antineoplastic drug in the host by natural unmutated host enzyme" means that the prodrug does not give undue untargeted toxicity problems on administration to the host.

The term "substantially non-immunogenic" means that the first component (conjugate) can be administered to the host on more than one occasion without causing significant host immune response as would be seen with for example the use of a mouse antibody linked to a bacterial enzyme in a human host.

Preferably the mutated enzyme is based on an enzyme from the same species as the host for which the system is intended for use but the mutated enzyme may be based on a host enzyme from a different species as long as the structure of the enzyme is sufficiently conserved between species so as not to create undue immunogenicity problems.

Preferably the targeting moiety is an antibody, especially an antibody fragment such as for example F(ab')$_2$. Linkage to enzyme for conjugate synthesis may be effected by known methods such as use of heterobifunctional reagents as cross-linkers or by gene fusion or any other suitable method. Antibody may be from the same host (eg use of mouse antibody in mice) or the antibody may be manipulated such that it is not significantly recognised as foreign in the chosen host (eg use of chimeric, CDR grafted or veneered mouse antibodies in humans). Preferably the first component is a conjugate as defined above.

Transplantation of the variable domains of rodent antibodies into the constant domains of human antibodies (Chimeric antibodies) or building the antigen binding loops (CDRS) of rodent antibodies into a human antibody (CDR grafting) have both been shown to greatly decrease the immunogenicity of the rodent antibody in preclinical studies in monkeys and in patients. Even CDR grafted antibodies incorporate a large number (>50) of amino acids from the rodent antibody sequence into the human framework. Despite this in monkeys and patients greatly reduced immunogenicity has been reported. This provides evidence that mutating a very limited number of amino acids in the catalytic site of a host enzyme is likely to result in an enzyme with minimal immunogenicity and certainly lower immunogenicity than a non-host enzyme. The reader is directed to the following references: A. Mountain and J. R. Adair, Biotechnology and Genetic Engineering Reviews 10, 1–142, 1992; G. Winter and V. J. Harris, Trends in Pharmacological Sciences, 14, 139–143, 1993; I. I. Singer et al, J. Immunol, 150, 2844–57, 1993; J. Hakimi et al, J. Immunol, 147, 11352–59, 1991 and; J. D. Isacs et al, The Lancet, 340, 748–752, 1992. The constant region domains may be for example human IgA, IgE, IgG or IgM domains. Human IgG2 and 3 (especially IgG2) are preferred but IgG 1 and 4 isotypes may also be used. Human antibodies per se may also be used such as those generated in mice engineered to produce human antibodies. (Fishwald et al. in Nature Biotechnology (1996), 14, 845–851).

The host enzyme is mutated to give a change in mode of interaction between enzyme and prodrug in terms of recognition of substrate compared with the native host enzyme.

Preferably the enzyme mutation is a polarity change in its active site such that it turns over a prodrug with a complementary polarity; the prodrug not being significantly turned over by the unmutated host enzyme. Preferably the natural host enzyme recognises its natural substrate by an ion pair interaction and this interaction is reversed in the design of mutated enzyme and complementary prodrug. In this specification the term "active site" includes amino acid residues involved in any aspect of substrate recognition and/or catalytic functionality.

Point mutations will be referred to as follows: natural amino acid (using the 1 letter nomenclature), position, new amino acid. For example "D253K" means that at position 253 of mature active HCPB an aspartic acid (D) has been changed to lysine (K). Multiple mutations in one enzyme will be shown between square brackets with individual mutations separated by commas.

In this specification the term CPB includes the following:
i) mature, pro and prepro forms of the enzyme with or without "tags" (eg c-myc);
ii) any carboxypeptidase with specificity for peptidic substrates having Lys or Arg at the C terminus having substantial sequence identity (preferably at least 60% identity, more preferably at least 70% identity, more preferably at least 80% identity and especially at least 90% identity) with mature active pancreatic HCPB within each of the key substrate binding sites 187–206 and 238–268;
preferably human pancreatic and plasma CPB enzymes (the pancreatic enzyme disclosed herein is preferred);
unless indicated otherwise or self evident from the context.

Naturally occurring allelic variants of CPBs are also contemplated. An allelic variant is an alternate form of sequence which may have a substitution, deletion or addition at one or more positions, which does not substantially alter the function of the CPB.

To determine the degree of identity between a carboxypeptidase and mature active pancreatic HCPB at its key substrate binding sites the following procedure is followed to align the sequences. When amino acid residues 109 to 415 of SEQ ID NO: 39 are renumbered 1 to 307, and aligned with other carboxypeptidases using a Clustal method with PAM250 residue weighting as described in the LASER-GENE biocomputing software for MACINTOSH User's Guide, A Manual for the LASERGENE system (2nd Edition, 1994, published by DNASTAR Inc., 1228 South Park Street, Madison, Wis. 53715, USA) the key zinc binding residues (at H66, E69 and H194), the key terminal-carboxy substrate binding residues (at R124, N141, R142, and Y246) and the catalytic residues (at R124, Y246 and E268) are essentially aligned. The key substrate recognition residue is deemed to be D253, with the substrate recognition pocket lying between the core β-sheet (including residues 187 to 206) and the active-site surface loop and helix (residues 238 to 268). Residues 263–268 (within sequence 238–268) are beta strand, although they are part of the core beta sheet.

Mutant CPBs of the invention are mutants of any of the above CPBs having the desired property required for the invention. The following mutants of pancreatic HCPB are preferred: D253K, D253R and; especially [G251N,D253R]; corresponding mutations in other CPBs are also contemplated. Key mutation positions are also set out in the following table.

| MUTATIONS FOR CHANGE OF HCPB SPECIFICITY | | | |
|---|---|---|---|
| Original Residue | Exemplary Substitution | Preferred Substitution | Especially Preferred Substitution |
| Gln 54 (Q54) | Arg, Lys, Asn | Arg | Arg |
| Asp 145 (D145) | Val, Leu, Ile, Ala | Ala | Ala |
| Ile 201 (I201) | Ser, Thr | Ser | Ser |
| Ser 205 (S205) | Asn, Gln, His, Lys, Arg | Asn | Asn |
| Ile 245 (I245) | Ser, Thr, Ala, Val, Leu, Asn, Gln, Lys, Arg, His | Ser, Ala, His | Ala |
| Ala 248 (A248) | Asn, Gln, Lys, Arg, His, Ser, Thr | His, Ser, Asn | Ser, Asn |
| Gly 251 (G251) | Thr, Asn, Ser, Gln, His, Lys, Arg, Val, Ile, Leu, Met, Phe, Ala, Norleucine | Thr, Asn, Ser Gln, Lys, Val | Thr, Asn, Ser |
| Asp 253 (D253) | Arg, Gln, Asn, Lys | Lys, Arg | Lys for prodrugs based on Glu recognition Arg for prodrugs based on Asp recognition |
| Cys 288 (C288) | Ser, Thr, Ala, Val, Leu, Ile | Ser, Ala | Ser |

Notes
1. Preferred mutation combinations of the above positions always have a change at position 253. More preferred mutation combinations have a change at both position 253 and 251. Changes at position 253, optionally in combination with position 251, are believed to be the key mutations for change of HCPB specificity.
2. Especially preferred combinations are [G251N, D253K] and [G251T, D253K]. Another especially preferred combination is [G215S, D253K].

A mutant CPB of the invention may also comprise other "conservative" mutations (insertions, substitutions and/or deletions) that do not significantly alter the properties of the key mutation. For the purposes of this document a conservative amino acid substitution is a substitution whose probability of occurring in nature is greater than ten times the probability of that substitution occurring by chance (as defined by the computational methods described by Dayhoff et al, Atlas of Protein Sequence and Structure, 1971, page 95–96 and FIGS. 9–10) and as set out in the following table.

| CONSERVATIVE SUBSTITUTIONS | | |
|---|---|---|
| Original | Exemplary Substitutions | Preferred Substitutions |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

References on CPBs include the following: Folk J E in The Enzymes Vol III, Academic Press (1971), pg 57; Coll M et al (1991) EMBO Journal 10, 1–9; Eaton D L et al (1991) J Biol Chem 266, 21833–21838; Yamamoto K et al (1992) J Biol Chem 267, 2575–2581; U.S. Pat. No. 5,364,934 (Genentech) and; International Patent Application WO 95/14096 (Eli Lilly).

According to another aspect of the present invention there is provided a system as hereinbefore defined for use in a method of controlling the growth of neoplastic cells in a host in which the method comprises administration to said host an effective amount of a first component, allowing the first component to clear substantially from the general circulation, and administering an effective amount of a second component. Preferably the components are administered intravenously.

According to another aspect of the invention there is provided a method of treating neoplastic cells in a host in which the method comprises administration to said host an effective amount of a first component, allowing the first component to clear substantially from the general circulation, and administering an effective amount of a second component wherein the components form a two component system as defined herein. Preferably the components are administered intravenously.

According to another aspect of the present invention there is provided a pharmaceutical composition comprising an effective tumour localising amount of a first component as hereinbefore defined and a pharmaceutically acceptable carrier or diluent. Preferably the composition is suitable for intravenous administration. Preferably the first component is supplied as a dry solid which is reconstituted before use with a suitable diluent.

According to another aspect of the present invention there is provided a pharmaceutical composition comprising an effective antitumour amount of a second component as hereinbefore defined and a pharmaceutically acceptable carrier or diluent. Preferably the composition is suitable for intravenous administration. Preferably the second component is supplied as a dry solid which is reconstituted before use with a suitable diluent.

*E.coli* MSD 1646 containing pCG330 (also known as pICI1698) was deposited under the Budapest Treaty on Nov. 23rd 1994 with the National Collection of Industrial and Marine Bacteria (NCIMB), 23 St Machar Drive, Aberdeen, Scotland, United Kingdom AB2 1RY; the accession number is NCIMB 40694. NCIMB 40694 is another aspect of the present invention.

Antibody A5B7 was deposited as hybridoma deposit reference 93071411 under the Budapest Treaty on Jul. 14th 1993 at ECACC, PHLS Centre for Applied Microbiology & Research, Porton Down, Salisbury, Wiltshire SP4 OJG, UK. A humanised antibody A5B7 in the form of a F(ab')$_2$ is preferred.

Antibody 806.077 was deposited as hybridoma deposit reference 96022936 under the Budapest Treaty on Feb. 29th 1996 at ECACC, PHLS centre for Applied Microbiology & Research, Porton Down, Salisbury, Wiltshire SP4 OJG, UK. Antibody 806.077 is an alternative anti-CEA antibody to A5B7 which is suitable for use in the present invention.

According to another aspect of the present invention there is provided a method of making a first component (conjugate) as herein described by linking:

a targeting moiety capable of binding with a tumour associated antigen and;

an enzyme capable of converting a prodrug into an antineoplastic drug wherein the enzyme is a mutated form of a host CPB enzyme. Linking may be effected by chemical or molecular biological techniques.

According to another aspect of the present invention there is provided a first component of the present invention.

According to another aspect of the present invention there is provided a polynucleotide sequence capable of encoding a first component (conjugate) of the present invention.

According to another aspect of the present invention there is provided a vector comprising a polynucleotide sequence capable of encoding a first component of the present invention.

According to another aspect of the present invention there is provided a cell comprising a vector or a polynucleotide sequence capable of encoding a first component of the present invention.

According to another aspect of the present invention there is provided a mutant CPB enzyme having the desired properties of the invention.

According to another aspect of the present invention there is provided a polynucleotide sequence capable of encoding a mutant CPB enzyme of the present invention. The present invention further relates to polynucleotides which hybridize to the polynucleotides encoding mutant CPBs if there is at least 70% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences.

According to another aspect of the present invention there is provided a vector comprising a polynucleotide sequence capable of encoding a mutant CPB enzyme of the present invention. The polynucleotide sequence may be included in any one of a variety of expression vehicles, in particular vectors or plasmids for expressing a polypeptide. Such vectors include chromosomal, nonchromosomal and synthetic DNA sequences, e.g., derivatives of SV40; bacterial plasmids; phage DNA; yeast plasmids; vectors derived from combinations of plasmids and phage DNA, viral DNA such as vaccinia, adenovirus, fowl pox virus, and pseudorabies. However, any other plasmid or vector may be used as long they are replicable and viable in the host. The appropriate DNA sequence may be inserted into the vector by a variety of procedures.

In general, the DNA sequence is inserted into an appropriate restriction endonuclease site(s) by procedures known in the art. Such procedures and others are deemed to be within the scope of those skilled in the art. The DNA sequence in the expression vector is operatively linked to an appropriate expression control sequence(s) (promoter) to direct mRNA synthesis. As representative examples of such promoters, there may be mentioned: LTR or SV40 promoter, the $E.coli.$ lac or trp, the phage lambda P.sub.L promoter and other promoters known to control expression of genes in prokaryotic or eukaryotic cells or their viruses. The expression vector also contains a ribosome binding site for translation initiation and a transcription terminator. The vector may also include appropriate sequences for amplifying expression. In addition, the expression vectors preferably contain a gene to provide a phenotypic trait for selection of transformed host cells such as dihydrofolate reductase or neomycin resistance for eukaryotic cell culture, or such as tetracycline or ampicillin resistance in $E.coli.$ The vector containing the appropriate DNA sequence as hereinabove described, as well as an appropriate promoter or control sequence, may be employed to transform an appropriate host to permit the host to express the protein. As representative examples of appropriate hosts, there may be mentioned: bacterial cells, such as $E.coli$, Streptomyces, *Salmonella Typhimurium;* fungal cells, such as yeast; insect cells such as Drosophila and Sf9; animal cells such as NSO, CHO, COS or Bowes melanoma; plant cells, etc. The selection of an appropriate host is deemed to be within the scope of those skilled in the art from the teachings herein. More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence.

Large numbers of suitable vectors and promoters are known to those of skill in the art, and are commercially available. The following vectors are provided by way of example. Bacterial: pQE70, pQE60, pQE-9 (Qiagen), pbs, pD10, phagescript, psiX174, pbluescript SK, pbsks, pNH8A,pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host. Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda P.sub.R, P.sub.L and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described construct. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by for example calcium phosphate transfection, DEAE-Dextran mediated transfection, lipofection (cationic lipid-mediated delivery of polynucleotides [Felgner et al. in Methods: A Companion to Methods in Enzymology (1993)

5, 67–75] or electroporation (Davis, L., Dibner, M., Battey, I., Basic Methods in Molecular Biology, (1986)). The skilled reader will be able to select the most appropriate method for a given host. The constructs in host cells can be used in a conventional manner to produce the gene product encoded by the recombinant sequence. Alternatively, the polypeptides of the invention can be synthetically produced by conventional peptide synthesizers. Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers. Generally, recombinant expression vectors will include origins of replication and selectable markers permitting transformation of the host cell, e.g., the ampicillin resistance gene of E. Coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), alpha-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product. Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E.coli, Bacillus subtilis, Salmonella typhimurium and various species within the genera Pseudomonas, Streptomyces, and Staphylococcus, although others may also be employed as a matter of choice. As a representative but nonlimiting example, useful expression vectors for bacterial use can comprise a selectable marker and bacterial origin of replication derived from commercially available plasmids comprising genetic elements of the well known cloning vector pBR322 (ATCC 37017), pAT153 and pBluescript. Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents, such methods are well known to those skilled in the art. Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the NSO, C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking non-transcribed sequences. DNA sequences derived from the SV40 splice, and polyadenylation sites may be used to provide the required nontranscribed genetic elements. Expression products are recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography hydroxylapatite chromatography and lectin chromatography. It is preferred to have low concentrations (approximately 0.15–5 mM) of calcium ion present during purification. (Price et al., J. Biol. Chem., 244:917 (1969). Protein refolding steps can be used, as necessary, in completing configuration of the mature protein. Finally, high performance liquid chromatography (HPLC) can be employed for final purification steps. The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated with mammalian or other eukaryotic carbohydrates or may be nonglycosylated. Polypeptides of the invention may also include an initial methionine amino acid residue.

Other systems of expression are also contemplated such as for example transgenic non-human mammals in which the gene of interest, preferably cut out from a vector and preferably in association with a mammary promoter to direct expressed protein into the animal's milk, is introduced into the pronucleus of a mammalian zygote (usually by microinjection into one of the two nuclei (usually the male nucleus) in the pronucleus) and thereafter implanted into a foster mother. A proportion of the animals produced by the foster mother will carry and express the introduced gene which has integrated into a chromosome. Usually the integrated gene is passed on to offspring by conventional breeding thus allowing ready expansion of stock. Preferably the protein of interest is simply harvested from the milk of female transgenic animals. The reader is directed to the following publications: Simons et al. (1988), Bio/Technology 6:179–183; Wright et al. (1991) Bio/

Technology 9:830–834; U.S. Pat. Nos. 4,873,191 and 5,322,775. Manipulation of mouse embryos is described in Hogan et al, "Manipulating the Mouse Embryo; A Laboratory Manual", Cold Spring Harbor Laboratory 1986.

Transgenic plant technology is also contemplated such as for example described in the following publications: Swain W. F. (1991) TIBTECH 9: 107–109; Ma J. K. C. et al (1994) Eur. J. Immunology 24: 131–138; Hiatt A. et al (1992) FEBS Letters 307:71–75; Hein M. B. et al (1991) Biotechnology Progress 7: 455–461; Duering K. (1990) Plant Molecular Biology 15: 281–294.

If desired, host genes can be inactivated or modified using standard procedures as outlined briefly below and as described for example in "Gene Targeting; A Practical Approach", IRL Press 1993. The target gene or portion of it is preferably cloned into a vector with a selection marker (such as Neo) inserted into the gene to disrupt its function. The vector is linearised then transformed (usually by electroporation) into embryonic stem (ES) cells (eg derived from a 129/Ola strain of mouse) and thereafter homologous recombination events take place in a proportion of the stem cells. The stem cells containing the gene disruption are expanded and injected into a blastocyst (such as for example from a C57BL/6J mouse) and implanted into a foster mother for development. Chimeric offspring can be identified by coat colour markers. Chimeras are bred to ascertain the contribution of the ES cells to the germ line by mating to mice with genetic markers which allow a distinction to be made between ES derived and host blastocyst derived gametes. Half of the ES cell derived gametes will carry the gene modification. Offspring are screened (eg by Southern blotting) to identify those with a gene disruption (about 50% of progeny). These selected offspring will be heterozygous and therefore can be bred with another heterozygote and homozygous offspring selected thereafter (about 25% of progeny). Transgenic animals with a gene knockout can be crossed with transgenic animals produced by known techniques such as microinjection of DNA into pronuclei, sphaeroplast fusion (Jakobovits et al. (1993) Nature 362 255–258) or lipid mediated transfection (Lamb et al. (1993) Nature Genetics 5 22–29) of ES cells to yield transgenic animals with an endogenous gene knockout and foreign gene replacement.

ES cells containing a targeted gene disruption can be further modified by transforming with the target gene sequence containing a specific alteration, which is preferably cloned into a vector and linearised prior to transformation. Following homologous recombination the altered gene is introduced into the genome. These embryonic stem cells can subsequently be used to create transgenics as described above.

The term "host cell" includes any procaryotic or eucaryotic cell suitable for expression technology such as for example bacteria, yeasts, plant cells and non-human mammalian zygotes, oocytes, blastocysts, embryonic stem cells and any other suitable cells for transgenic technology. If the context so permits the term "host cell" also includes a transgenic plant or non-human mammal developed from transformed non-human mammalian zygotes, oocytes, blastocysts, embryonic stem cells, plant cells and any other suitable cells for transgenic technology.

According to another aspect of the present invention there is provided a cell comprising a vector or a polynucleotide sequence capable of encoding a mutant CPB enzyme of the present invention. According to another aspect of the present invention there is provided a nucleotide sequence encoding a mature human pancreatic carboxypeptidase B defined in SEQ ID NO: 39 from position 109 onwards or a mutant thereof in which there is a cysteine residue encoded at position 243. This cysteine residue at position 243 in the cloned sequence is not observed in other published human pancreatic carboxypeptidase B sequences, as highlighted by Yamamoto et al, in the Journal of Biological Chemistry, v267, 2575–2581, 1992, where she shows a gap in her sequence following the position numbered 244, when aligned with other mammalian pancreatic carboxypeptidase B amino acid sequences (see discussion in Reference Example 6). Preferably the nucleotide sequence is in isolated form, that is to say at least partially purified from any naturally occurring form. Preferably the mutants are mutant CPB enzymes suitable for the present invention.

According to another aspect of the present invention there is provided a method of making human pancreatic carboxypeptidase B or a mutant thereof in which there is a cysteine residue encoded at position 243 comprising expression in a host cell of a nucleotide sequence encoding a mature human pancreatic carboxypeptidase B defined in SEQ ID NO: 39 from position 109 onwards or a mutant thereof in which there is a cysteine residue encoded at position 243.

According to another aspect of the present invention there is provided prodrugs of Formula 1 wherein:

w represents a direct bond or $CH_2$ $R^1$ and $R^2$ independently represent Cl, Br, I or —$OSO_2Me$ $R^3$ and $R^4$ independently represent H, $C_{1-3}$alkyl, $C_{1-3}$alkoxy, F or Cl $C_4$alkyl or $R^5$ and $R^6$ independently represent H or $C_{1-4}$alkyl or $R^3$ and $R^6$ together can represent —CH=CH—CH=CH— to form a bicyclic ring system optionally containing 1–3 heteroatoms selected from O, N and S X is selected from —$CHR^7CHR^8$— where $R^7$ and $R^8$ are selected from H and $C_{1-4}$alkyl optionally substituted with phenyl provided at least $R^7$ or $R^8$ is H;

—$NHCHR^9$— where $R^9$ is selected from H;

the side chain of common amino acids including for example the side chain of Ala, Arg, Asn, Asp, Cys, Glu, Gln, His, Ile, Leu, Lys, Met, Phe, Ser, Thr, Trp, Tyr & Val;

$(CH_2)_n CONHR^{10}$ where n=1–3 and $R^{10}$ is selected from $C_{1-6}$alkyl, cyclopentyl, cyclohexyl and phenyl and each $R^{10}$ listed hereinbefore is optionally substituted with halogen, $C_{1-4}$alkyl or $C_{1-4}$alkoxy;

—NH—$N(R^{12})$— where $R^{12}$ is selected from H and $C_{1-4}$alkyl;

Y represents NH or O

Z is selected from

—$(CH_2)_n$—$CO_2H$ (n=1–4)

—$CH_2OCH_2CO_2H$

—$CH_2$—CH=CH—$CO_2H$

—$(CH_2)_n$tetrazol-5yl (n=1–4)

—$(CH_2)_n CONHSO_2R^{11}$ (n=1–4) in which $R^{11}$ is selected from $C_{1-4}$alkyl —$(CH_2)_n SO_2NH_2$ (n=1–4) and salts thereof.

According to another aspect of the present invention there is provided any one of the following compounds or a pharmaceutically acceptable salt thereof:

a) N-(4-{4-[bis-(2-chloroethyl)-amino]-3-methyl-phenoxy}-benzoyl)-L-alanine;

b) N-[N-(4-{4-[bis-(2-chloroethyl)-amino]-3-methyl-phenoxy}-benzoyl)-L-alanine]-L-glutamic acid;

c) N-(4-{4-[bis-(2-chloroethyl)-amino]-phenoxy}-benzoyl)-L-alanine; or d) N-[N-(4-{4-bis-(2-chloroethyl)-amino]-phenoxy}-benzoyl)-L-alanine]-L-glutamic acid.

Compounds b) and d) are preferred prodrug second components of the invention. Compounds a) and c) are the corresponding drugs.

According to another aspect of the present invention there is provided a compound of Formula 1 or prodrugs b) or d) described above or a pharmaceutically acceptable salt thereof for use as a medicament.

According to another aspect of the present invention there is provided the compound of Formula 1 or prodrugs b) or d) described above or a pharmaceutically acceptable salt thereof for preparation of a a medicament for treatment of cancer (in combination with a first component of the invention).

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of Formula 1 may exist in optically active or racemic forms by virtue of one or more asymmetric carbon atoms, the invention includes in its definition any such optically active or racemic form which possesses the property of being a substrate for mutant CPBs of the invention. However in compounds of Formula 1, at the carbon atom having groups Y, Z and COOH attached, if there is a corresponding free amino acid then the carbon atom preferably has an L configuration in the corresponding free amino acid.

The synthesis of optically active forms may be carried out by standard techniques of organic chemistry well known in the art, for example by synthesis from optically active starting materials or by resolution of a racemic form. Similarly, substrate properties against mutant CPBs may be evaluated using the standard laboratory techniques.

A suitable pharmaceutically-acceptable salt of a basic compound of Formula 1 is, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of an acidic compound of Formula 1 is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

The compounds of this invention may be utilized in compositions such as tablets, capsules or elixirs for oral administration, suppositories for rectal administration, sterile solutions or suspensions for parenteral or intramuscular administration, and the like. The compounds of this invention can be adminstered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg. per patient per day which can be administered in single or multiple doses.

Preferably, the dosage range will be about 2.5 to 250 mg. per patient per day; more preferably about 2.5 to 75 mg. per patient per day.

Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions and discussed below.

About 1 to 100 mg. of compound or mixture of compounds of Formula 1 or a physiologically acceptable salt thereof is compounded with a physiologically acceptable vehicle, carrier, excipient, binder, preservative, stabilizer, flavor, etc., in a unit dosage form as called for by accepted pharmaceutically practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

A compound of the invention of Formula I, or a pharmaceutically-acceptable salt thereof, may be prepared by any process known to be applicable to the preparation of structurally-related compounds. Such procedures are provided as a further feature of the invention and are illustrated by the following representative examples in which variable groups have any of the meanings defined hereinbefore unless otherwise indicated. Where a synthesis of a particular compound is expanded upon below it will be appreciated that the general methodology can be applied to cover all compounds of the particular structure under discussion.

1. Compounds with W=Direct Bond

Such compounds may be prepared as outlined in FIG. 9. These prodrugs are cleaved by mutant CPB to liberate an intermediate which further collapses to release the corresponding phenol mustard (typical $IC_{50}$=1.5 $\mu$M).

Suitable reagents for steps a–d include:
(a) DCCI, HOBT or water soluble carbodiimide (EDCI) or isobutyl chloroformate/triethylamine;
(b) TFA (if $P_1$=t-butyl, $P_2$ is benzyl) or $H_2$,Pd/C (if $P_1$ is benzyl and $P_2$=t-butyl);
(c) EDCI,DHAP,$CHCl_3$,
(d) $H_2$/Pd/C if $P_2$=benzyl or TFA if t-butyl is used in the protection.

Compound 2 in FIG. 9 i) When Y=NH$_2$ and P$_2$ is a protecting group such as benzyl, and when Z is for example —(CH$_2$)$_n$—CO$_2$H (n=1–4) then when n=1, dibenzyl L-aspartic acid is used; when n=2, L-glutamic acid dibenzyl ester is used and; when n=3, L-2-amino adipic acid dibenzyl ester is used.

ii) When Z is —(CH$_2$)$_n$-tetrazole: in the case of for example n=2, the sequence of reactions illustrated in FIG. 10 is used to generate the required dibenzyl protected intermediate from the known methyl ester. Suitable reagents for steps a–e include:
  (a) Cs$_2$CO$_3$, PhCH$_2$Br, DMF;
  (b) 10% Pd/C, H$_2$,BOC-O-BOC;
  (c) NaOH, MeOH, H$_2$O;
  (d) Cs$_2$CO$_3$, PhCH$_2$Br, DMF; isomers separated;
  (e) HCl, ether, CH$_2$Cl$_2$ iii) When Z is —(CH$_2$)$_n$CONHSO$_2$R$^{11}$ in the case of for example n=2 and R$^{11}$=Me, the protected intermediate is made from N-BOC-α-benzyl glutamic acid as illustrated in FIG. 11. Suitable reagents for steps a–b include:
  (a) MeSO$_2$NH$_2$, DCCI, DMAP;
  (b) HCl, EtOAc.

When Z=—(CH$_2$)$_n$SO$_2$NH$_2$ in the case for example n=2, then L-2-amino-4-sulfamoylbutyric acid-benzyl ester, produced from L-2-amino-4-sulfamoylbutyric acid (Aldrich Chemical Company), is used.

v) Compounds where Y is OH are generated by established routes or by for example using compounds such as L-malic acid instead of the corresponding L-glutamic acid.

Compound 3 in FIG. 9 i) When X=—CH$_2$CH$_2$— the intermediate can be made by reacting a compound illustrated as compound 2 in FIG. 9 with succinic anhydride to generate the half succinate ester where P$_1$=H. Alternatively half esters of succinic acid can be used to couple to the above intermediate instead of using succinic anhydride.

ii) When X=—NHCH(R$^9$)— the prodrug is cleaved by mutant CPB to generate a compound of Formula 5 which is directly cytotoxic. For example when R$^9$ =(CH$_2$)$_2$CONH—nC$_4$H and R$^1$=R$^2$=Cl, R$^3$=R$^4$=R$^5$=R$^6$=H the cytotoxicity versus LoVo cells is about IC$_{50}$=20 μM.

To make compounds where X=NHCH(R$^9$) conventional peptide coupling methodology is used as illustrated in FIG. 12. The intermediate is then treated with acid (eg HCl/ether) to form the free amine. Coupling to the phenol mustard is carried out as illustrated in FIG. 13. Suitable reagents for step a include:
  1. para-nitrophenylchloroformate, triethylamine, chloroform
  2. triethylamine, CH$_2$Cl$_2$ or;
  1. COCl$_2$/Quinoline, CH$_2$Cl$_2$
  2. triethylamine, CH$_2$Cl$_2$ Compounds where W=CH2 and X=—NH—NH(R$^{12}$)—

Such compounds may be synthesised as illustrated in FIG. 14. Suitable reagents for steps a–b include:
  (a) BOC—N(R$^{12}$)—NH$_2$, EDAC, CH$_2$Cl$_2$; TFA, HCl/ETOAc
  (b)
    1. pyridine, CH$_2$Cl$_2$
    2. triethylamine, CH$_2$Cl$_2$ The resulting product is then deprotected by standard methods.

When a pharmaceutically-acceptable salt of a compound of the formula I is required, it may be obtained, for example, by reaction of said compound with a suitable acid or base using a conventional procedure. When an optically active form of a compound of the formula I is required, it may be obtained by carrying out one of the aforesaid procedures using an optically active starting material, or by resolution of a racemic form of said compound using a conventional procedure.

Further uses of mutant CPBs of the invention include the following.

i) Carboxypeptidase enzymes may be used for the sequential removal of C-terminal amino acids from proteins and, following amino acid analysis of the residues released, can be used for determining the C-terminal amino acid sequence of proteins (R. P. Ambler, in: Methods in Enzymology, 1967, vol. X1, 436–445, Academic Press). The use of a mutant CPB possessing specificity for C-terminal aspartate and glutamate residues allows the use of these enzymes in extending the scope and ease of C-terminal analysis by carboxypeptidase digestion.

ii) Mutant enzymes may be used as enzyme labels in immunoassays. Product from substrate (prodrug) turnover may be detected by any suitable technique eg HPLC. Immunoassay techniques using enzymes as labels are described in A Practical Guide to ELISA by D. M. Kemeny, Pergamon Press 1991.

The invention will now be described by the following non-limiting Examples (with reference to the Reference Examples) in which:

(i) evaporations were carried out by rotary evaporation in vacuo and work-up procedures were carried out after removal of residual solids by filtration;

(ii) operations were carried out at room temperature, that is in the range 18–25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany;

(iv) yields are given for illustration only and are not necessarily the maximum attainable;

(v) the end-products of the Formula I have satisfactory microanalyses and their structures were confirmed by nuclear magnetic resonance (NMR) and mass spectral techniques; unless otherwise stated, CDCl$_3$ solutions of the end-products of the Formula I were used for the determination of NMR spectral data, chemical shift values were measured on the delta scale; the following abbreviations have been used: s, singlet; d, doublet; t, triplet; m, multiplet;

(vi) intermediates were not generally fully characterised and purity was assessed by thin layer chromatographic, infra-red (IR) or NMR analysis;

(vii) melting points are uncorrected and were determined using a Mettler SP62 automatic melting point apparatus or an oil-bath apparatus; melting points for the end-products of the formula I were determined after crystallisation from a conventional organic solvent such as ethanol, methanol, acetone, ether or hexane, alone or in admixture and;

(viii) all temperatures are in °C.

A BRIEF DESCRIPTION OF THE FIGURES IS SET OUT BELOW

FIG. 4 illustrates pICI1266 expression vector gene cloning SEQ ID NO: 87).

FIG. 6 lists the composition of a growth medium.

FIGS. 7–14 illustrate chemical synthetic procedures.

Figure 15:
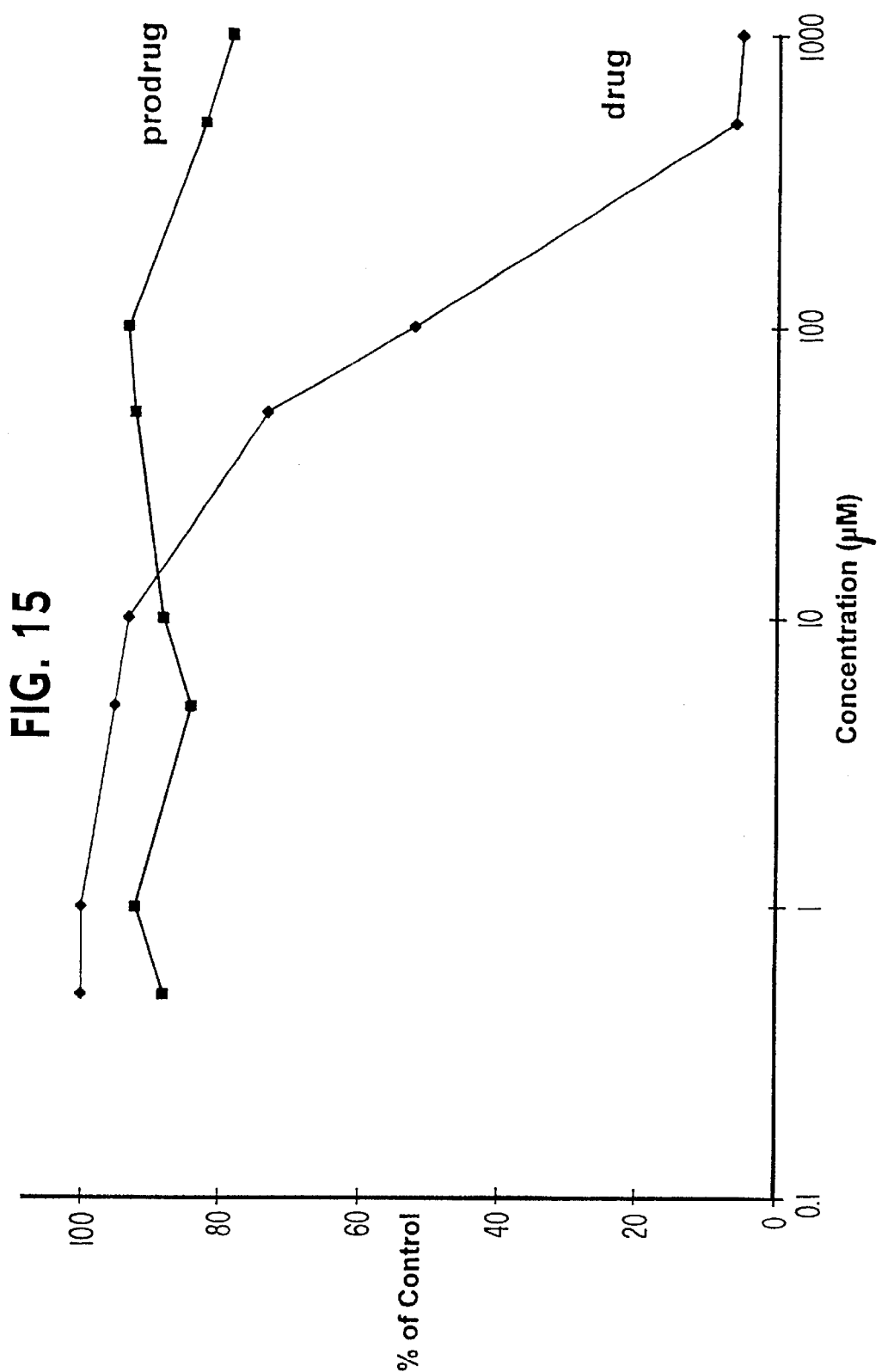

FIG. 15 shows cytotoxicity of the prodrug of Example 21 alone and corresponding drug of Example 22 alone in LoVo tumour cells.

Figure 16:
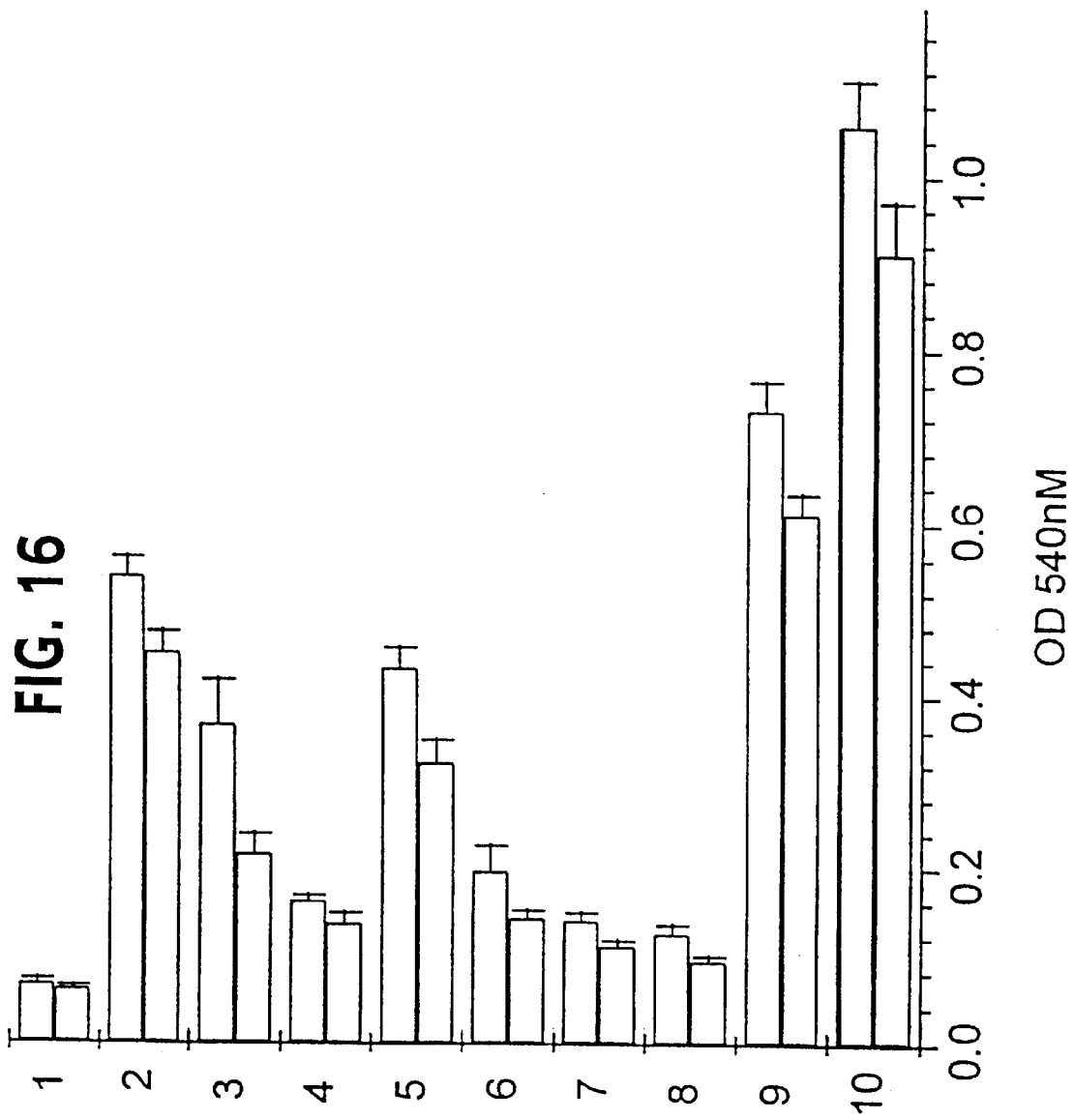

FIG. 16 shows cytotoxicity of the prodrug of Example 21 in the presence of the mutated enzyme, D253K HCPB in LoVo tumour cells. Numbered rows represent the following: 1=blank (no cells); 2–4=the drug of Example 22 at 50, 100 & 200 μM respectively; 5–8=the prodrug of Example 21 in the presence of 1.47, 2.4, 5.9 & 11.75 μg/ml of D253K HCPB respectively; 9=the prodrug of Example 21 at 500 μM; and 10=control (cells only). Each numbered row contains 2 bars (with margin of error indicated) wherein each bar represents data from 6 wells on a plate.

Figure 17:
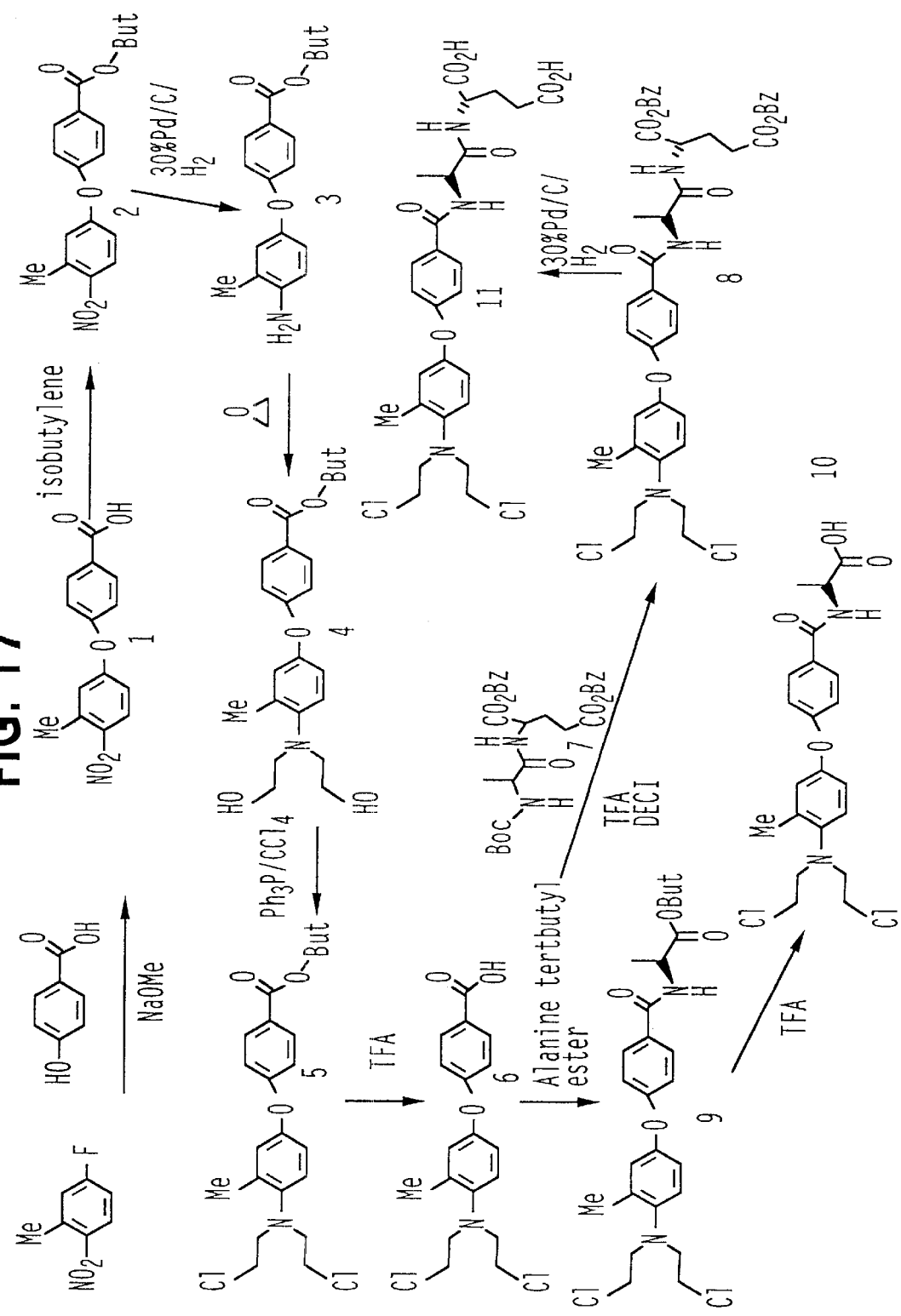

FIG. 17 illustrates a chemical synthesis.

Figure 8:
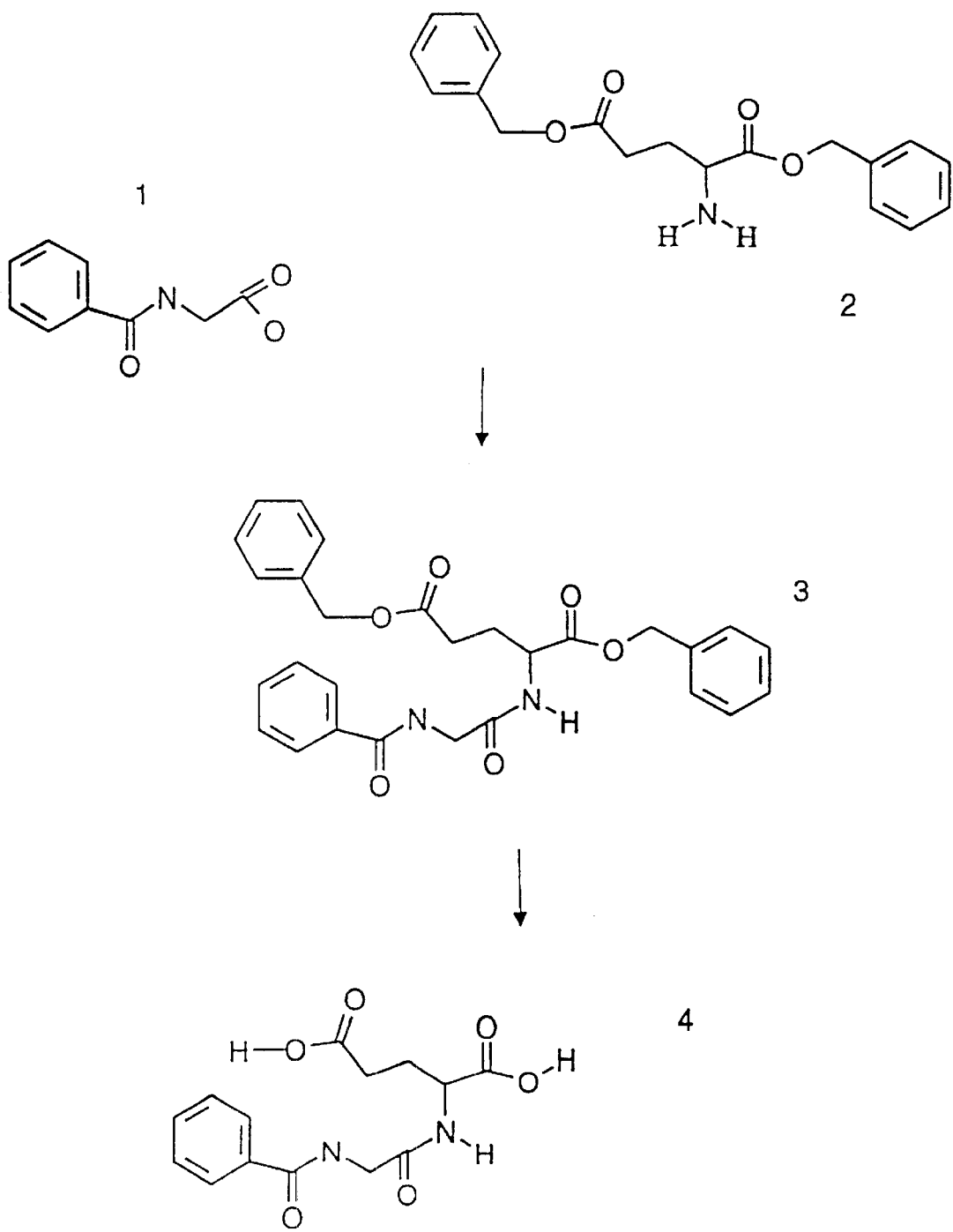
Figure 9:
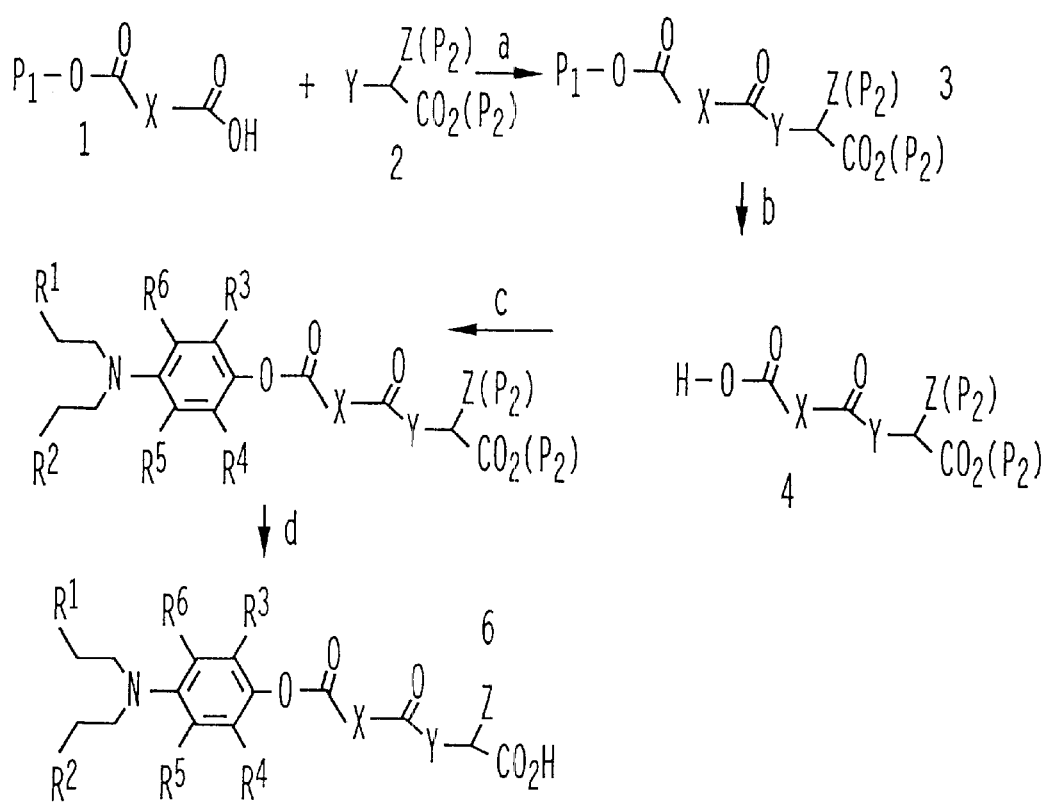
Figure 10:
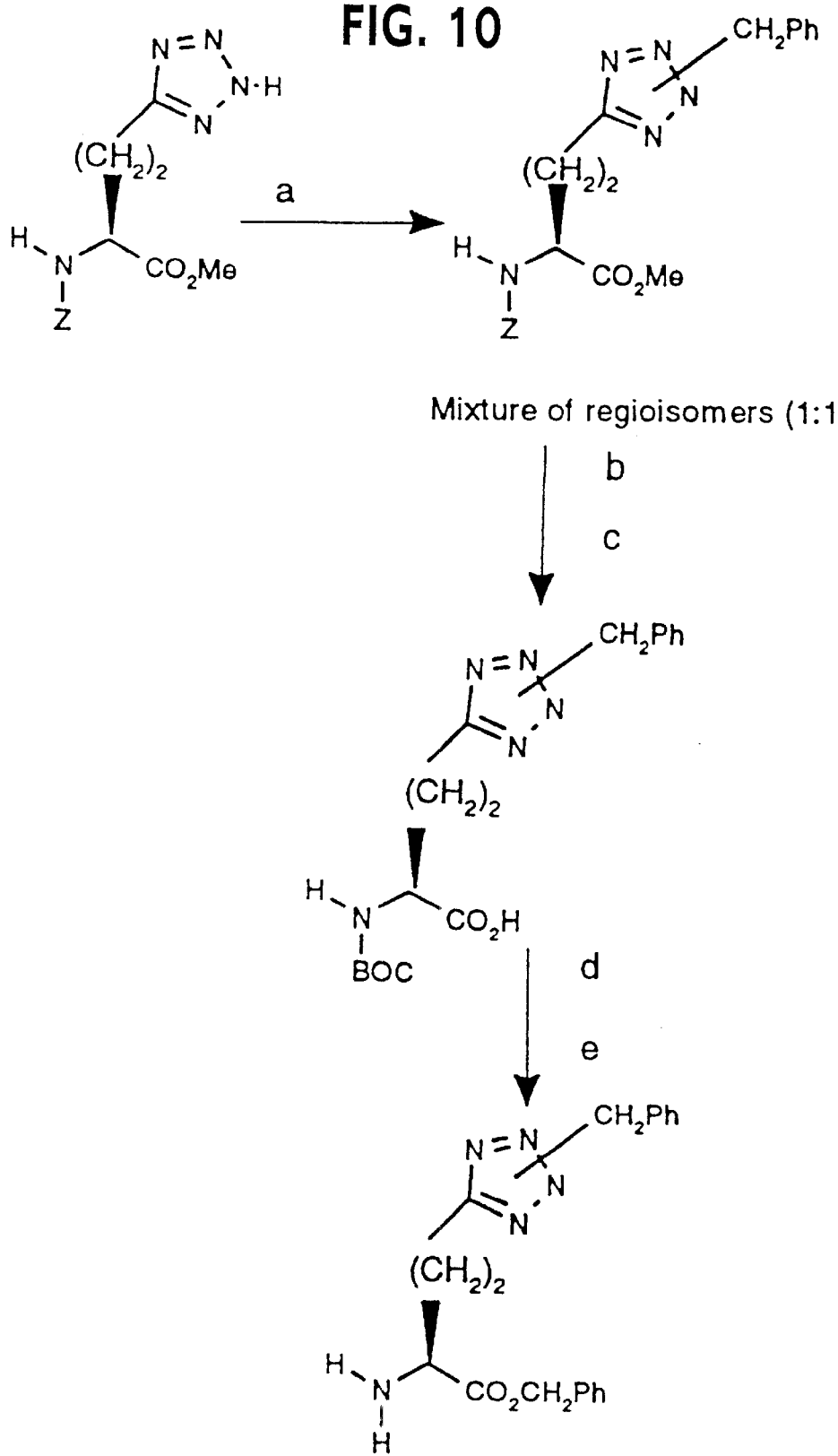
Figure 11:
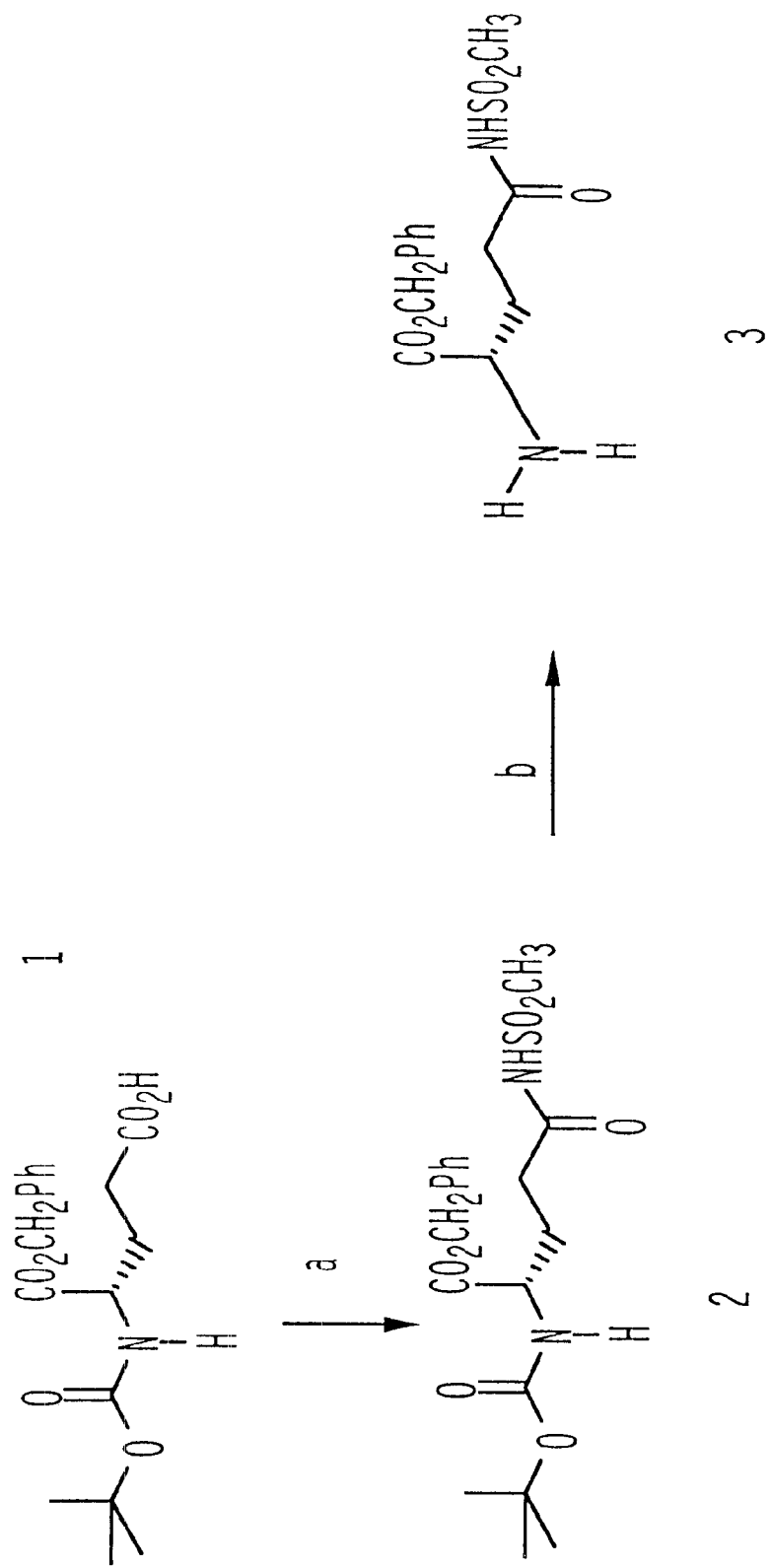
Figure 12:
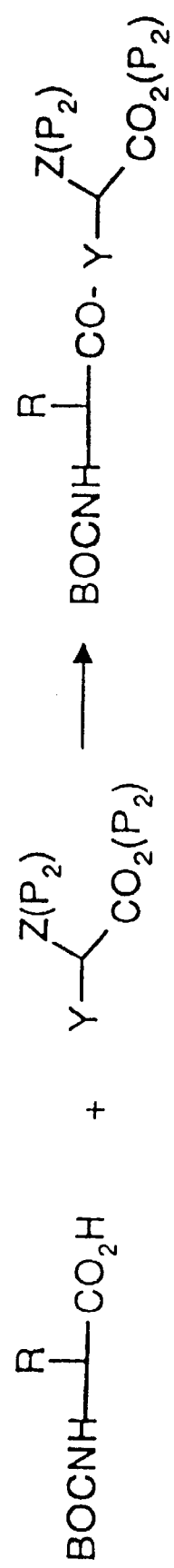
Figure 13:
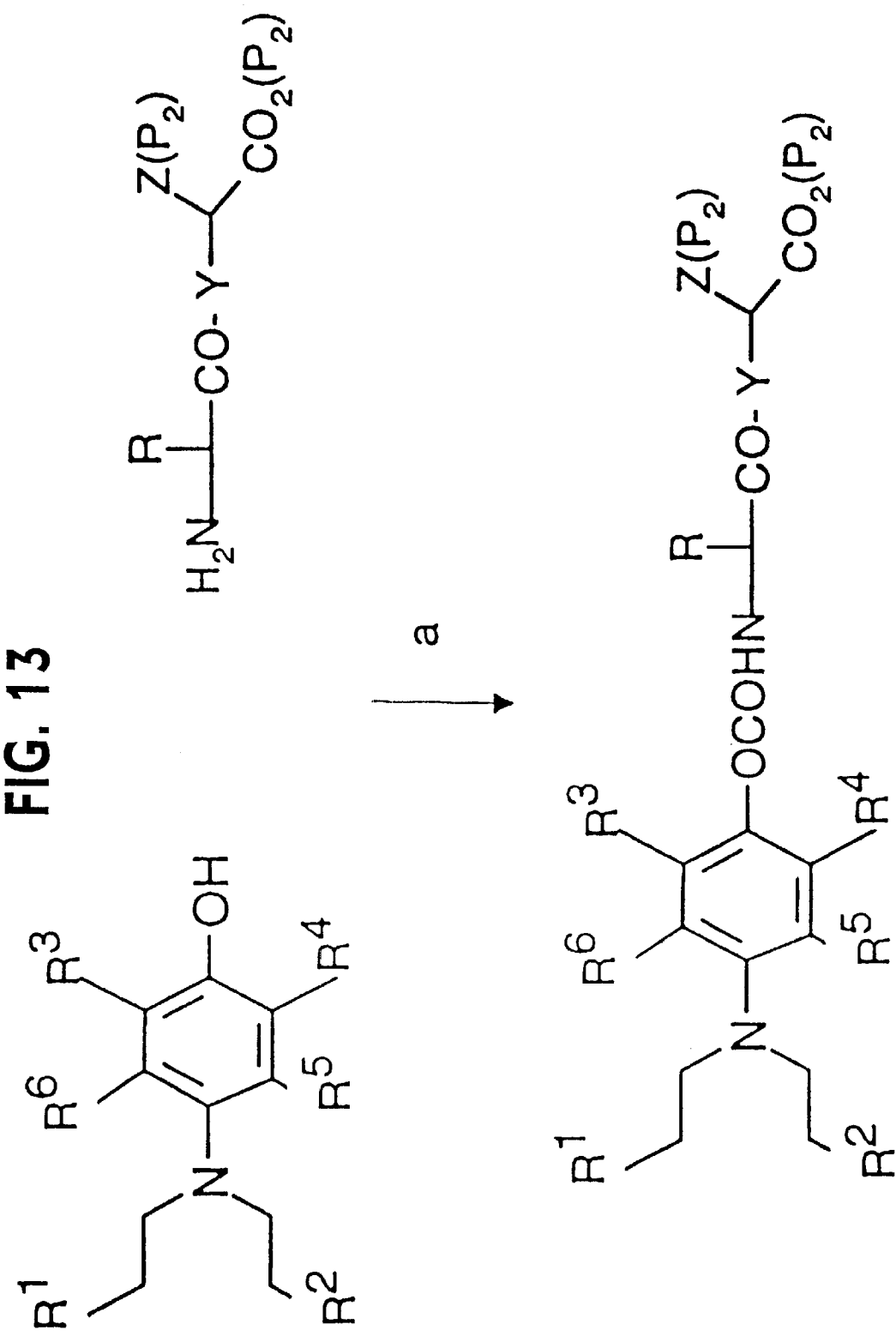
Figure 14:
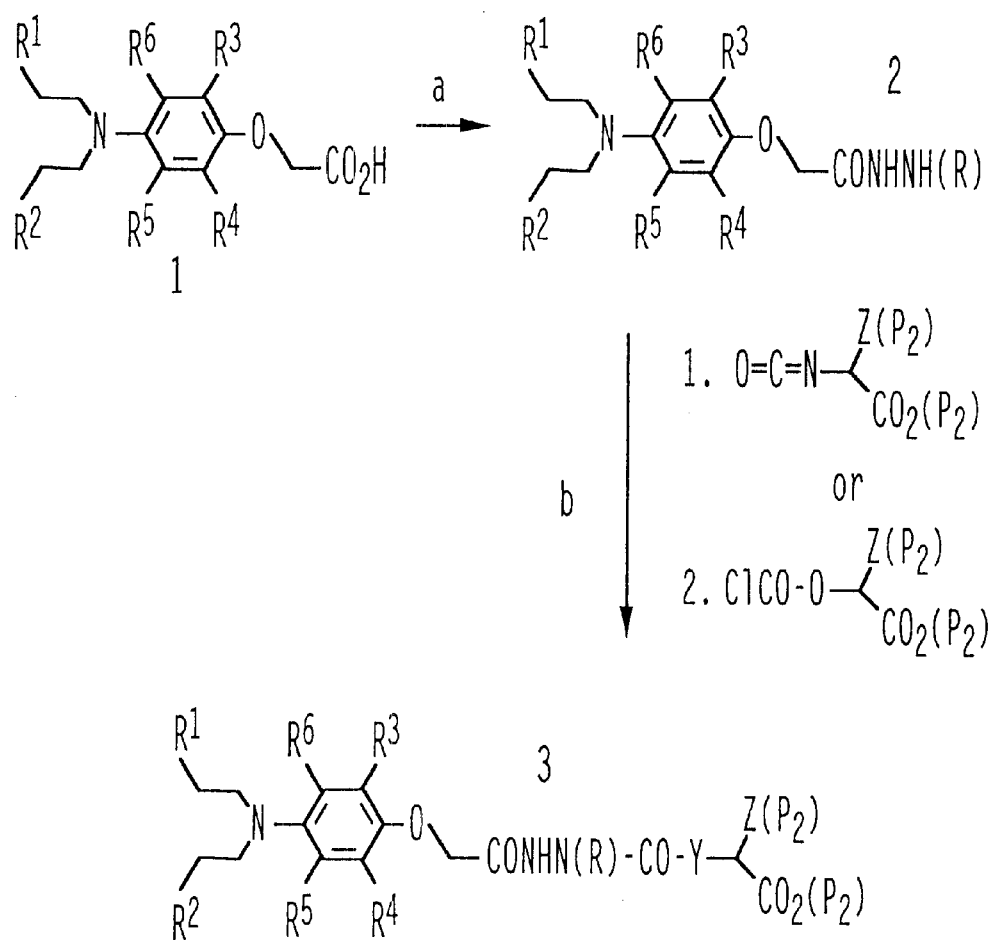

REFERENCE EXAMPLE 1
Synthesis of Hippuryl-L-Glutamic Acid (see FIG. 8)

Hippuryl-L-glutamic acid dibenzyl ester (compound 3) (2.06 g, $4.2 \times 10^{-3}$ moles) and 30% Pd/Carbon (50% moist) (0.77 g) in THF were stirred in an atmosphere of hydrogen for 1.5 hours. The mixture was filtered through diatomaceous silica (Celite™) and the filtrate evaporated to dryness. Trituration with diethyl ether gave the desired end product as a white crystalline solid 1.02 g (78%). Melting point 169–171° C. 20D=–2.5°.

NMR DMSO d6 12.3, 2H (broad); 8.7, 1H (t); 8.2, 1H (t); 7.9, 2H (m); 7.5, 3H (m); 4.3, 1H (m); 3.9, 2H (m); 2.3, 2H (t); 1.9, 2H (m)

The starting material compound 3 was prepared as follows. To a solution of hippuric acid (0.90 g, $5 \times 10^{-3}$ moles) and L-glutamic acid dibenzyl ester (2.50 g, $5 \times 10^{-3}$ moles) in DMF (35 ml) was added 1-hydroxybenzotriazole (0.73 g, $5.5 \times 10^{-3}$ moles), triethylamine (1.4 ml, $9.7 \times 10^{-3}$ moles) and 1(3-dimethyl-aminopropyl)-3-ethylcarbodiimide, HCl salt (1.05 g, $5.5 \times 10^{-3}$ moles). The mixture was stirred overnight at room temperature, poured into water (400 ml) and extracted twice with ethyl acetate (100 ml). The combined extracts were washed with saturated sodium bicarbonate solution, water, 2N HCl and water. The organic phase was dried over MgSO$_4$ and evaporated to obtain the desired starting material as a yellow oil. 2.06 g (84%).

NMR DMSO d6 8.7, 1H (t); 8.4, 1H (d); 7.9, 2H (m); 7.5, 3H (m); 7.35, 10H (m); 5.15, 2H (s); 5.05, 2H (s); 4.4, 1H (m); 3.9, 2H (t); 2.0, 4H (m).

REFERENCE EXAMPLE 2
Synthesis of Hippuryl-L-Aspartic Acid

Hippuryl-L-aspartic acid dibenzyl ester (1.28 g, $2.7 \times 10^{-3}$ moles) and 30% Pd/Carbon (50% moist) (0.51 g) in THF were stirred in an atmosphere of hydrogen for 3 hours. The mixture was filtered through Celite™ and the filtrate evaporated to dryness. Trituration with diethyl ether gave an off-white crystalline solid 0.62 g (78%).

Melting point 200–202° C. 20D=+7.9°.

NMR DHSO d6 12.5, 2H (broad); 8.7, 1H (t); 8.2, 1H (d); 7.7, 2H (m); 7.5, 3H (m); 4.6, 1H (m); 3.9, 2H (d); 2.7, 2H (m)

The starting material was synthesised as follows. To a solution of hippuric acid (0.90 g, $5 \times 10^{-3}$ moles) and L-aspartic acid dibenzyl ester (2.31 g, $5 \times 10^{-3}$ moles) in DMF (35 ml) was added 1-hydroxybenzotriazole (0.73 g, $5.5 \times 10^{-3}$ moles), triethylamine (1.4 ml, $9.7 \times 10^{-3}$ moles) and 1-(3-dimethyl-aminopropyl)-3-ethylcarbodiimide, HCl salt (1.05 g, $5.5 \times 10^{-3}$ moles). The mixture was stirred for 4 hours at room temperature then poured into water (450 ml) and extracted twice with ethyl acetate (100 ml). The extract was washed with saturated sodium bicarbonate solution, water, 2N HCl and water. The organic phase was dried over MgSO$_4$ and evaporated to dryness to obtain the desired starting material as a yellow oil. 1.90 g (80%)

NHR DMSO d6 8.7, 1H, (t); 8.45, 1H, (d); 7.9, 2H (m); 7.5, 3H (m); 7.3, 10H (m); 5.15, 2H (s); 5.05, 2H (s); 4.8, 1H (m); 3.9, 2H (m); 2.9, 2H (m).

REFERENCE EXAMPLE 3
Enzymic activity of recombinant HCPB against Hipp-Arg

Purified human CPB, produced as described in Reference Example 12, was assayed for its ability to convert hippuryl-L-arginine (Hipp-Arg; Sigma) to hippuric acid using a spectrophotometric assay.

The Km and kcat for native HCPB were determined by measuring the initial rate of conversion of Hipp-Arg to hippuric acid at 254 nM using a range of Hipp-Arg concentrations (0.75–0.125 mM) and a CPB enzyme concentration of 1 μg/ml. Measurements were carried out at 37° C. in 0.25 mM Tris HCl buffer, pH 7.5 using 1 cm path length cuvettes in a total volume of 1.0 ml using a Perkin Elmer Lambda 2 spectrophotometer. Km and Vmax values were calculated using the ENZFITTER software programme (Biosoft, Perkin Elmer). Kcat was calculated from Vmax by dividing by the enzyme concentration in the reaction mixture.

The results for human CPB against Hipp-Arg were:

Km=0.18 mM kcat=65 s$^{-1}$

The results demonstrate that the recombinant HCPB is enzymatically active and can cleave the amide bond in Hipp-Arg to release Hippuric acid.

Figure 7:
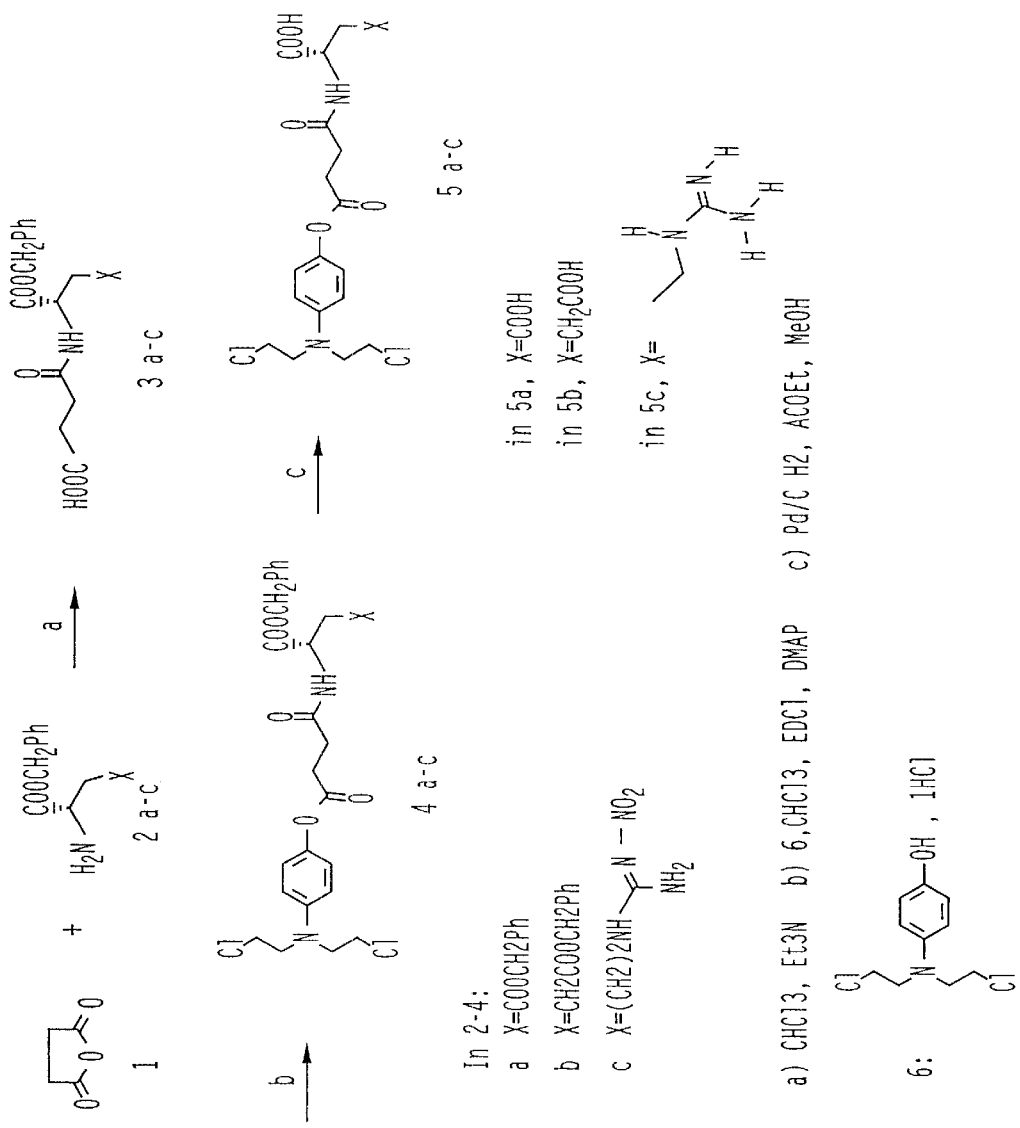

REFERENCE EXAMPLE 4
Synthesis of an Arginine Mustard Prodrug (See FIG. 7)

(2S),2-(3-{4-[bis-(2-chloroethyl)-amino)-phenoxycarbonyl}-propionyl-amino)-5-guanidino-pentoic acid (compound 5c, FIG. 7)

A solution of (2S),2-(3-{4-[bis-(2-chloroethyl)-amino)-phenoxycarbonyl}-propionyl-amino)-5-(2-nitro)-guanidino-pentoic acid benzyl ester (compound 4c, FIG. 7) (275 mg; 0.44 mmol) in ethyl acetate/MeOH (1/1: V/V) (8 ml) containing 10% Pd/C (200 mg) was hydrogenated in a Paar apparatus at 80 psi for 6 h. After filtration the organic layer was evaporated. The resulting oil was recrystallised using CH$_2$Cl$_2$/diethyl ether to give the desired compound 5c as a white solid (180 mg), yield 84%.

$^1$HNMR (CD$_3$OD): 1.55–1.7 (m, 3H); 1.8–1.9 (m, 1H); 2.6–2.7 (m, 2H); 2.75–2.85 (m, 1H); 2.9–2.95 (m, 1H); 3.1–3.2 (m, 2H); 3.6–3.7 (m, 4H); 3.7–3.8 (m, 4H); 4.3 (dd, 1H); 6.75 (dd, 2H); 6.95 (dd, 2H).

MS (ESI): 512–514 (MNa)+

Anal (C$_{20}$H$_{29}$N$_5$O$_4$Cl$_2$ 1.5 H$_2$O)

Calc. C, 47.91; H, 6.43; N, 13.97.

Found C, 47.7; H, 6.21; N, 14.26.

Starting material compound 4c was prepared as follows. To a solution of (2S),2-amino-5-(2-nitro)-guanidino-pentoic acid benzyl ester (compound 2c) (654 mg; 1 mmol) in CHCl$_3$ (10 ml) was added dihydro-furan-2,5-dione (compound 1) (120 mg; 2 mmol) followed by triethylamine (202 mg; 2 mmol) dropwise. After stirring for 2h at room temperature, the solvent was evaporated and the crude residue was dissolved in water. pH was adjusted to 2.5 with 2N HCl. The aqueous layer was extracted with ethyl acetate. The organic layer was washed with brine, dried (MgSO$_4$) and evaporated to give (2S),2-(3-carboxy-propionylamino)-5-(2-nitro)-guanidino-pentoic acid benzyl ester (compound 3c). The resulting solid was triturated with diethylether and filtered off: 280 mg (68%).

1HNMR (CD3OD): 1.52–1.68 (m, 2H); 1.7–1.8 (m, 1H); 1.85–1.95 (m, 1H); 2.45–2.7 (m, 4H); 3.15–3.3 (m, 2H); 4.5 (m, 1H); 5.15 (dd, 2H); 7.25–7.4 (m, 5H)

MS (ESI): 432 [MNa]+

To a suspension of compound 3c (204 mg; 0.5 mmol) in CHCl$_3$ (5 ml) was added 4-[bis(2-chloroethyl)amino]-phenol (compound 6) (135 mg; 0.5 mmol), EDCI (19 mg; 0.5 mmol) followed by DMAP (18 mg; 0.75 mmol). After stirring at room temperature for 6h, the solvent was evaporated. The residue was partitioned between ethyl acetate and water and the aqueous phase acidifed to pH=3 with 2N HCI. After extraction with ethyl acetate, the organic layer was washed with brine, dried (MgSO$_4$) and evaporated. The residue was purified by flash chromatography using CH$_2$Cl$_2$/MeOH (95/5: V/V) as eluant to give the desired starting material 4c as a white foam (281 mg) yield: 90%. 4c: $^1$HNMR (CD$_3$OD): 1.55–1.7 (m, 2H); 1.7–1.8 (m, 1H); 1.85–1.95 (m, 1H); 2.55–2.75 (m, 2H); 2.8–2.9 (m, 2H); 3.15–3.25 (m, 2H); 3.6–3.7 (m, 4H); 3.7–3.8 (m, 4H); 4.5 (dd, 1H); 5.15 (dd, 2H); 6.7 (d, 2H); 6.95 (d, 2H); 7.32 (m, 5H)

MS (ESI): 647–649 [MNa]+

REFERENCE EXAMPLE 5

Synthesis of succinic acid mono-{4-[N,N-bis(2-chloroethyl)amino]-phenyl} ester (also called "intermediate" herein)

To a suspension of succinic anhydride (225 mg, 2.25 mmol) in CHCl$_3$ (10 ml) was added under stirring, 4-[N,N-bis(2-chloroethyl)-amino]phenol (compound 6, FIG. 7; 203 mg, 0.75 mmol) followed by triethylamine (75 mg, 0.75 mmol). The mixture was stirred overnight and the solvent evaporated. The crude residue was dissolved in EtOAC/Et$_2$O/H$_2$O and under stirring the pH was adjusted to 3. The organic layer was washed with water, brine, dried (MgSO$_4$), and evaporated. The resulting oil was crystallised from Et$_2$O/hexane and the white solid was filtered off and dried under vacuum to obtain the desired end product (210 mg; yield 83%). Melting point 98–100° C.

MS (ESI): 356–358 [MNa]$^+$ $^1$H NMR (CDCl$_3$): 2.8 (dd, 2H); 2.9 (dd,2H); 3.65 (dd, 4H); 3.75 (dd, 4H); 6.65 (d, 2H); 7.0 (d, 2H)

Analysis (C$_{14}$H$_{17}$Cl$_2$O$_4$N 0.2H$_2$O):

Calc. %C, 49.78; H, 5.19; N, 4.15.

Found %C, 49.9; H, 5.3; N, 4.2.

REFERENCE EXAMPLE 6

Cloning of Human Pancreatic Carboxypeptidase B (HCPB)

Standard molecular biology techniques, such as restriction enzyme digestion, ligation, kinase reactions, dephosphorylation, polymerase chain reaction (PCR), bacterial transformations, gel electrophoresis, buffer preparation and DNA generation, purification and isolation, were carried out as described by Maniatis et al., (1989) Molecular Cloning, A Laboratory Manual; Second edition: Cold Spring Harbor Laboratory, Cold Spring Harbor, N.Y., or following the recommended procedures of manufacturers of specific products. In most cases enzymes were purchased from New England BioLabs, but other suppliers, and equivalent procedures may be used. Oligonucleotide sequences were prepared in an Applied Biosystems 380A DNA synthesiser from 5'dimethoxytrityl base-protected nucleoside-2-cyanoethyl-N,N'-di-isopropyl-phosphoramidites and protected nucleoside linked to controlled-pore glass supports on a 0.2 pmol scale, according to the protocols supplied by Applied Biosystems Inc.

The coding sequence for human pancreatic carboxypeptidase B was obtained from a human pancreatic cDNA library cloned in the λgt10 vector (Clontech, Human pancreas 5' STRETCH cDNA, HL1163a) using PCR technology, and cloned into the plasmid vector pBluescript II KS+ (Stratagene).

Typically, an aliquot of the cDNA library (5 μl at a tires of >10$^8$ pfu/ml) was mixed with 100 pMols of two oligonucleotide primers, BPT1 and BPB1, (SEQ ID NO: 28 and SEQ ID NO: 29), dNTPs to a final concentration of 200 μM, Taq polymerase reaction buffer, and 2.5 U of Taq polymerase in a final volume of 100 μl. The mixture was heated at 94° C. for 10 minutes prior to addition to the Taq enzyme, and the PCR incubation was carried out using 30 cycles of 94° C. for 1.5 minutes, 50° C. for 2 minutes, and 72° C. for 2 minutes, followed by a single incubation of 72° C. for 9.9 minutes at the end of the reaction.

Figure 1:
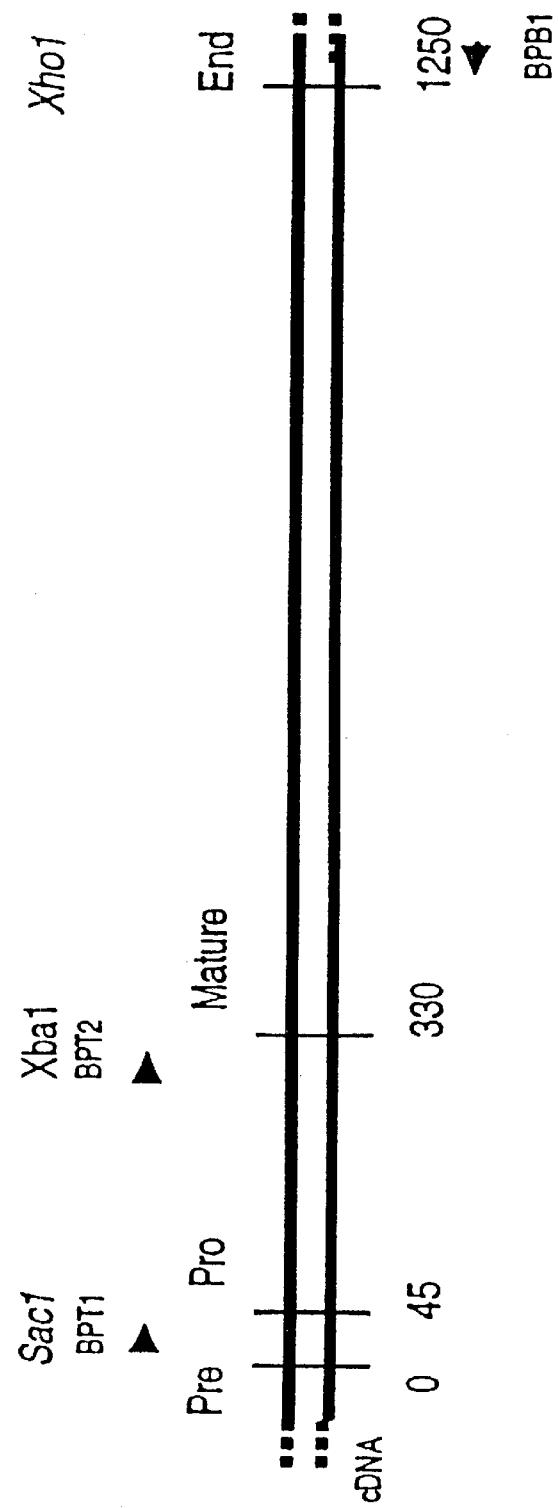
FIG. 1 illustrates pancreatic HCPB cloning.

The two oligonucleotide primers were designed to allow PCR extension from the 5' of the gene from BPT1 (SEQ ID NO: 28), between the start of the pre-sequence and the start of the pro-sequence, and PCR extension back from the 3' end of the gene from BPB1 (SEQ ID NO: 29), as shown in FIG. 1. BPT1 and BPB1 are also designed to introduce unique restriction sites, SacI and XhoI respectively, into the PCR product.

An aliquot of the PCR product was analysed for DNA of the correct size (about 1250 base pairs) by agarose gel electrophoresis and found to contain predominantly a band of the correct size. The remainder of the product from the reaction mix was purified and separated from excess reagents using a Centricon 100 microconcentrator column (Amicon), followed by DNA isolation by ethanol/sodium acetate precipitation, centrifugation, vacuum drying and re-suspension in distilled water. The isolated DNA was restriction digested with enzymes SacI and XhoI, and a band of the correct size (about 1250 base pairs) purified and isolated from agarose gel electrophoresis using excision and glass-milk (Geneclean, Stratec Scientific, or other similar product).

pBluescript II KS+ double stranded DNA (Stratagene) was restriction digested with SacI enzyme, and the product dephosphorylation treated with calf intestinal alkaline phosphatase to remove 5'phosphoryl groups and reduce re-ligation and vector background following transformation. The DNA product was purified from enzyme reaction contaminants using glass-milk, and then restriction digested with XhoI enzyme. DNA of the correct size (about 2850 base pairs) was purified and isolated by agarose gel electrophoresis using excision and glass-milk (Geneclean, Stratec Scientific, or other similar product).

Aliquots of both restricted and purified DNA samples were checked for purity and concentration estimation using agarose gel electrophoresis compared with known standards.

From these estimates ligation mixes were prepared to clone the HCPB gene into the vector, using a molar ratio of about 1 vector to 2.5 insert (1 pBluescript II KS+ to 2.5 HCPB PCR product), and a final DNA concentration of about 2.5 ng/μl, in the presence of T4 DNA ligase, 1 mM ATP and enzyme buffer.

Following the ligation reaction the DNA mixture was used to transform E.coli strain DH5α (Gibco-BRL, maximum efficiency competent cells). Cell aliquots were plated on L-agar nutrient media containing 100 μg/ml ampicillin as selection for plasmid vector, and incubated over-night at 37° C. Colonies containing plasmids with inserts of interest were identified by hybridisation.

About 200 colonies were picked and plated onto duplicate sterile nitro-cellulose filters (Schleicher and Schull), pre-wet on plates of L-agar nutrient media containing 100 μg/ml ampicillin as selection for plasmid vector, and incubated over-night at 37° C. One duplicate plate is stored at 4° C., and acts as a source of live cells for the colonies, the other plate is treated to denature and fix the DNA from the individual colonies to the nitro-cellulose. The nitro-cellulose filter is removed from the agar plate and placed in succession onto Whatman filter papers soaked in:
1. 10% SDS for 2 minutes
2. 0.5M NaOH, 1.5M NaCl for 7 minutes
3. 0.5M NaOH, 1.5M NaCl for 4 minutes
4. 0.5M NaOH, 1.5M NaCl for 2 minutes
5. 0.5M Tris pH7.4, 1.5M NaCl for 2 minutes
6. 2×SSC (standard saline citrate) for 2 minutes.

The filter is then placed on a Whatman filter paper soaked in 10×SSC and the denatured DNA is crossed linked to the nitro-cellulose by ultra violet light treatment (Spectrolinker XL-1500 UV crosslinker). The filters are then allowed to air dry at room temperature, and are then pre-hybridised at 60° C. for one hour in a solution of 6×SSC with gentle agitation (for example using a Techne HB-1D hybridizer). Pre-hybridization blocks non-specific DNA binding sites on the filters.

In order to determine which colonies contain DNA inserts of interest the DNA crosslinked to the nitro-cellulose filter is hybridised with a radio-labelled $^{32}$P-DNA probe prepared from HCPB PCR product of the pancreatic cDNA library (see above). About 50 ng of DNA was labelled with 5 μCi of $^{32}$P-dCTP (~3000 Ci/mMol) using T7 DNA polymerase in a total volume of 50 μl (Pharmacia T7 Quickprime kit), and the reaction allowed to proceed for 15 minutes at 37° C. The labelled probe is then heated to 95° C. for 2 minutes, to denature the double stranded DNA, immediately added to 10 ml of 6×SSC at 60° C., and this solution used to replace the pre-hybridisation solution on the filters. Incubation with gentle agitation is continued for about 3 hours at 60° C. After this time the hybridisation solution is drained off, and the filters washed twice at 60° C. in 2×SSC for 15 minutes each time. Filters were then gently blotted dry, covered with cling film (Saran™ wrap or similar), and exposed against X-ray film (for example Kodak Xomat-AR5™) over-night at room temperature. Following development of the film, colonies containing inserts of interest were identified as those which gave the strongest exposure (darkest spots) on the X-ray film. In this series of experiments about 15% of the colonies gave positive hybridisation. From this 12 colonies were chosen for further screening. These colonies were picked from the duplicate filter, streaked and maintained on L-agar nutrient media containing 100 μg/ml ampicillin, and grown in L-broth nutrient media containing 100 μg/ml ampicillin.

The selected isolates were checked by PCR for inserts of the correct size, using primers BPT1 and BPB1, (SEQ ID NO: 28 and SEQ ID NO: 29), and for priming with an internal primer BPT2 (SEQ ID NO: 30) and BPB1. BPT2 is designed to prime at the end of the pro-sequence, prior to the start of the mature gene and to introduce an XbaI restriction site.

For PCR screening colonies of the selected isolates were picked and dispersed into 200 μl of distilled water and heated at 100° C. for 10 minutes in a sealed Ependorph tube. The suspensions were then centrifuged for 10 minutes in a microfuge to pellet cell debris, and 1 μl of the supernatant used as the DNA template in PCR screening. Typically, 1 μl of supernatant was mixed with 2 pMols of two oligonucleotide primers, BPT1 and BPB1, or BPT2 and BPB1, dNTPs to a final concentration of 200 μM, Taq polymerase reaction buffer, and 0.5 U of Taq polymerase in a final volume of 20 μl. The PCR incubation was carried out using 25 cycles of 94° C. for 1.5 minutes, 50° C. for 2 minutes, and 72° C. for 2 minutes, followed by a single incubation of 72° C. for 9.9 minutes at the end of the reaction.

The PCR products were analysed for DNA of the correct size (about 1250 base pairs from primers BPT1 to BPB1, and about 900 base pairs from primers BPT2 to BPB1, see FIG. 1) by agarose gel electrophoresis. Ten of the twelve clones gave PCR DNA products of the correct size. Six of the ten clones were then taken for plasmid DNA preparation (using Qiagen Maxi kits, from 100 ml of over-night culture at 37° C. in L-broth with 100 μg/ml ampicillin). These plasmid DNA preparations were then sequenced over the region of PCR product insert using an USB Sequenase DNA sequencing kit, which incorporates bacteriophage T7 DNA polymerase. Each clone was sequenced using eight separate oligonucleotide primers, known as 676, 336, 337, 679, 677, 1280, 1279 and 1281 (SEQ ID NOs: 30 to 37). The positioning of the sequencing primers within the HCPB sequence is shown diagramatically in FIG. 2, primers 336, 1279, 676, 1280, 677 and 1281 being 'forward', and 337 and 679 'backwards'.

Figure 2:
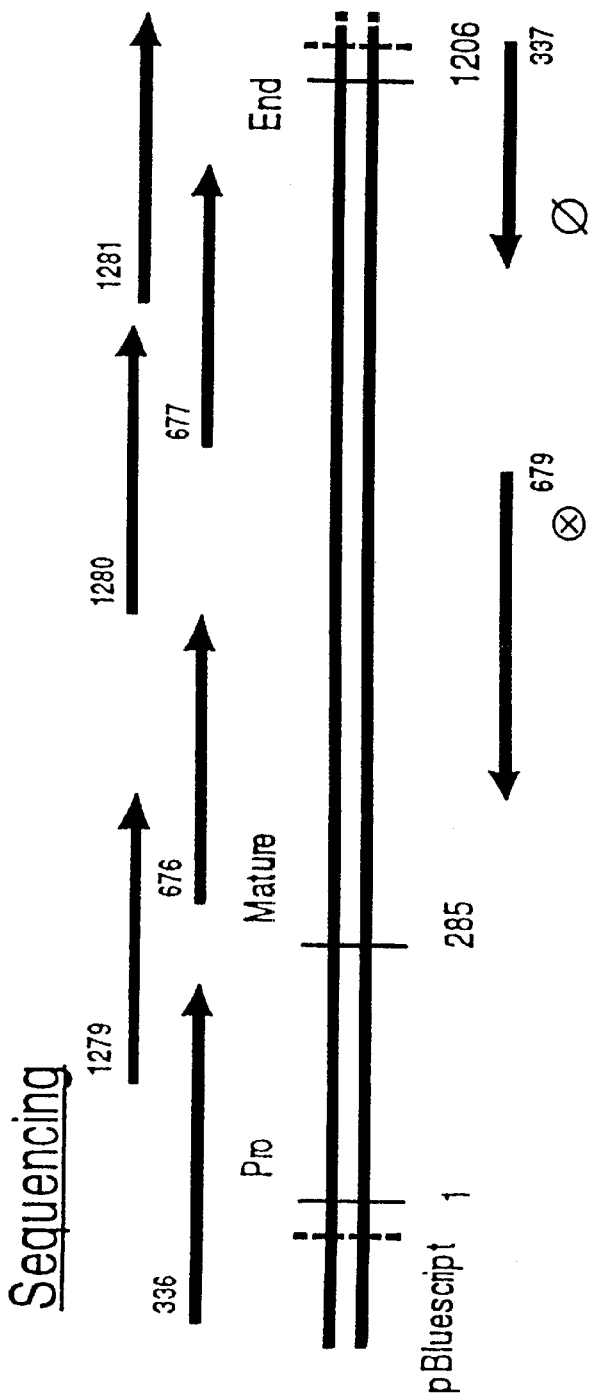
FIG. 2 Illustrates pancreatic HCPB sequencing (SEQ ID NOS: 84–85).

Five of the six clones were found to have identical sequence (SEQ ID NO: 38) of 1263 base pairs between and including the SacI and XhoI restriction sites, and this sequence was used in further experiments. The translation of the DNA sequence into its polypeptide sequence is shown in SEQ ID NO: 39. The start of the mature protein sequence is amino acid residue 109. Amino acid numbered 14 marks the start of the putative pro-enzyme sequence. Only part of the enzyme secretion leader sequence (pre-sequence) is present in the cloned PCR generated DNA. The polypeptide sequence shows an aspartate residue at position 361, which when the whole sequence is aligned with other mammalian carboxypeptidase A and B sequences indicates a B type specificity (see amino acids numbered 255 by Catasus L, et al, Biochem J., 287, 299–303, 1992, and discussion). However, the cysteine residue at position 243 in the cloned sequence is not observed in other published human pancreatic carboxypeptidase B sequences, as highlighted by Yamamoto et al, in the Journal of Biological Chemistry, v267, 2575–2581, 1992, where she shows a gap in her sequence following the position numbered 244, when aligned with other mammalian pancreatic carboxypeptidase B amino acid sequences. Also shown on FIG. 2 are the approximate sites of the aspartate amino acid residue in the enzyme recognition site, and the cysteine residue at position 135 of the mature enzyme (position 243 in SEQ ID NO: 39).

One of the clones was deposited on Nov. 23, 1994 with the National Collection of Industrial and Marine Bacteria Limited (23 St. Machar Drive, Aberdeen AB2 1RY, Scotland) and has the designation NCIMB 40694. The plasmid from this clone is known as pICI1698.

REFERENCE EXAMPLE 7
Expression of Mature HCPB-(His)$_6$-c-Myc from *E.coli*

Figure 3:
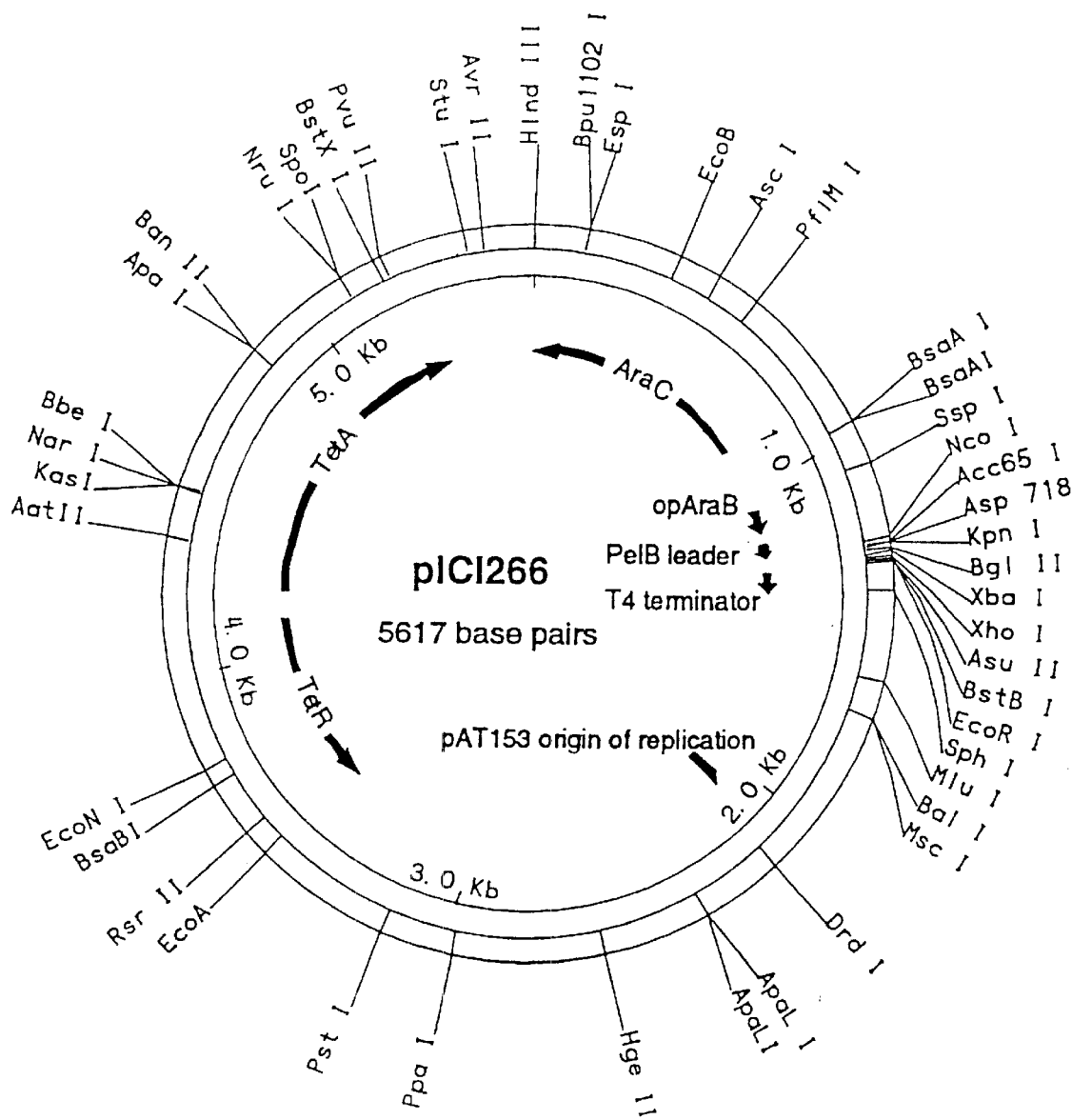
FIG. 3 illustrates vector pICI1266.

In order to achieve the expression of mature HCPB from *E.coli* the mature gene from pICI1698 was transferred into a plasmid vector which allows controlled secretion of protein products into the periplasm of the bacteria. This secretion vector, known as pICI266, in a bacterial host MSD522 suitable for controlled expression, has been deposited on Oct. 11, 1993 with the National Collection of Industrial and Marine Bacteria Limited (Aberdeen AB2 1RY, Scotland) and has the designation NCIMB 40589. A plasmid map of pICI266 is shown in FIG. 3. The plasmid has genes for tetracycline resistance and induction (TetA and TetR), an AraB operator and promoter sequence for inserted gene expression, and an AraC gene for expression control. The promoter sequence is followed by the PelB translation leader sequence which directs the polypeptide sequence following it to the periplasm. The site of gene cloning has several unique restriction sites and is followed by a phage T4 transcription terminator sequence. The DNA sequence in this region and the features for gene cloning are shown diagramatically in FIG. 4.

For the cloning of the mature HCPB sequence into pICI266 it was decided to generate HCPB DNA by PCR, and to make some alterations to the codon usage at the start of the mature gene to introduce *E.coli* preferred codons. Also, to help with detection and purification of the expression construct a C-term peptide tag, known as (His)$_6$-c-myc was added to the enzyme. The tag consists of 6 histidines, a tri-peptide linker (EPE) and a peptide sequence (EQKLISEEDL) SEQ ID NO: 86 from c-myc which is recognised by the antibody 9E10 (as published by Evan et al, Mol Cell Biol, v5, 129–136, 1985, and available from Cambridge Research Biochemicals and other antibody suppliers). The C-term is completed by the addition of an Asparagine. The 6 histidine residues should allow the purification of the expressed protein on a metal chelate column (for example Ni-NTA Agarose from Qiagen). In addition the PCR primers are used to introduce unique restriction sites at the 5' (FspI) and 3' (EcoRI) of the gene to facilitate the introduction of the PCR product into the expression vector. The sequence of the two primers, known as FSPTS1 and 6HIS9E10R1BS1, are shown in SEQ ID NOs: 40 and 41.

To generate a modified gene for cloning into pICI266, PCRs were set up using 100 pMols of primers FSPTS1 and 6HIS9E10R1BS1 in the presence of approximately 5 ng of pICI1698 DNA, dNTPs to a final concentration of 200 $\mu$M, Taq polymerase reaction buffer, and 2.5 U of Taq polymerase in a final volume of 100 $\mu$l. The mixture was heated at 94° C. for 10 minutes prior to addition to the Taq enzyme, and the PCR incubation was carried out using 30 cycles of 94° C. for 1.5 minutes, 50° C. for 2 minutes, and 72° C. for 2 minutes, followed by a single incubation of 72° C. for 9.9 minutes at the end of the reaction. An aliquot of the PCR product was analysed for DNA of the correct size (about 1000 base pairs) by agarose gel electrophoresis and found to contain predominantly a band of the correct size. The remainder of the product from the reaction mix was purified and separated from excess reagents using a Centricon 100 microconcentrator column (Amicon), followed by DNA isolation by ethanol/sodium acetate precipitation, centrifugation, vacuum drying and re-suspension in distilled water. The isolated DNA was restriction digested with enzymes FspI and EcoRI, and a band of the correct size (about 1000 base pairs) purified and isolated from agarose gel electrophoresis using excision and glass-milk (Geneclean, Stratec Scientific, or other similar product).

pICI266 double stranded DNA, prepared using standard DNA technology (Qiagen plasmid kits or similar), was restriction digested with KpnI enzyme, being very careful to ensure complete digestion. The enzyme was then inactivated by heating at 65° C. for 10 minutes, and then cooling on ice. The 3' over-hang generated by the KpnI was then enzymatically digested by the addition of T4 DNA polymerase as recommended by the supplier (New England BioLabs), in the presence of dNTPs and incubation at 16° C. for 15 minutes. The reaction was stopped by inactivating the enzyme by heating at 70° C. for 15 minutes. The DNA product was purified from enzyme reaction contaminants using glass-milk, an aliquot checked for yield by agarose gel electrophoresis, and the remainder restriction digested with EcoRI enzyme. Again care was taken to ensure complete restriction digest. DNA of the correct size (about 5600 base pairs) was purified and isolated by agarose gel electrophoresis using excision and glass-milk (Geneclean, Stratec Scientific, or other similar product).

Aliquots of both restricted and purified DNA samples were checked for purity and concentration estimation using agarose gel electrophoresis compared with known standards. From these estimates ligation mixes were prepared to clone the HCPB gene into the vector, using a molar ratio of about 1 vector to 2.5 insert (1 pICI266 to 2.5 HCPB PCR product), and a final DNA concentration of about 2.5 ng/$\mu$l, in the presence of T4 DNA ligase, 1mM ATP and enzyme buffer, using conditions suitable for the ligation of blunt ended DNA (FspI to T4 DNA polymerase treated KpnI).

Following the ligation reaction the DNA mixture was used to transform *E.coli* strain DH5$\alpha$ (Gibco-BRL, maximum efficiency competent cells). Cell aliquots were plated on L-agar nutrient media containing 10 $\mu$g/ml tetracycline as selection for plasmid vector, and incubated over-night at 37° C. Colonies containing plasmids with inserts of interest were identified by hybridisation.

About 350 colonies were picked and plated onto duplicate sterile nitro-cellulose filters (Schleicher and Schull), pre-wet on plates of L-agar nutrient media containing 10 $\mu$g/ml tetracycline as selection for plasmid vector, and incubated over-night at 37° C. One duplicate plate is stored at 4° C., and acts as a source of live cells for the colonies, the other plate is treated to denature and fix the DNA from the individual colonies to the nitro-cellulose. The nitro-cellulose filter is removed from the agar plate and placed in succession onto Whatman filter papers soaked in:

1. 10% SDS for 2 minutes
2. 0.5M NaOH, 1.5M NaCl for 7 minutes
3. 0.5M NaOH, 1.5M NaCl for 4 minutes
4. 0.5M NaOH, 1.5M NaCl for 2 minutes
5. 0.5M Tris pH7.4, 1.5M NaCl for 2 minutes
6. 2×SSC (standard saline citrate) for 2 minutes.

The filter is then placed on a Whatman filter paper soaked in 10×SSC and the denatured DNA is crossed linked to the nitro-cellulose by ultra violet light treatment (Spectrolinker XL-1500 UV crosslinker). The filters are then allowed to air dry at room temperature, and are then pre-hybridised at 60° C. for one hour in a solution of 6×SSC with gentle agitation (for example using a Techne HB-1D hybridizer). Pre-hybridization blocks non-specific DNA binding sites on the filters.

In order to determine which colonies contain DNA inserts of interest, the DNA crosslinked to the nitro-cellulose filter is hybridised with a radio-labelled 32P-DNA probe prepared from HCPB PCR product of the pancreatic cDNA library (see above). About 50 ng of DNA was labelled with 5 $\mu$Ci of $^{32}$P-dCTP (~3000 Ci/mMol) using T7 DNA polymerase in a total volume of 50 μl (Pharmacia T7 Quickprime kit), and the reaction allowed to proceed for 15 minutes at 37° C. The labelled probe is then heated to 95° C. for 2 minutes, to denature the double stranded DNA, immediately added to 10 ml of 6×SSC at 60° C., and this solution used to replace the pre-hybridisation solution on the filters. Incubation with gentle agitation is continued for about 3 hours at 60° C. After this time the hybridisation solution is drained off, and the filters washed twice at 60° C. in 2×SSC for 15 minutes each time. Filters were then gently blotted dry, covered with cling film (Saran wrap or similar), and exposed against X-ray film (for example Kodak Xomat-ARS) over-night at room temperature. Following development of the film, colonies containing inserts of interest were identified as those which gave the strongest exposure (darkest spots) on the X-ray film. In this series of experiments about 50% of the colonies gave positive hybridisation. From this 12 colonies were chosen for further screening. These colonies were picked from the duplicate filter, streaked and maintained on L-agar nutrient media containing 10 μg/ml tetracycline, and grown in L-broth nutrient media containing 10 μg/ml tetracycline.

The selected isolates were checked by PCR for inserts of the correct size, using primers FSPTS1 and 6HIS9E10R1BS1, (SEQ ID NO: 40 and SEQ ID NO: 41), and for priming with an internal primer BPB2 (SEQ ID NO: 33) and FSPT1. BPB2 is designed to prime within the mature gene and generate a fragment of about 430 base pairs.

For PCR screening colonies of the selected isolates were picked and dispersed into 200 μl of distilled water and heated at 100° C. for 10 minutes in a sealed tube. The suspensions were then centrifuged for 10 minutes in a microfuge to pellet cell debris, and 1 μl of the supernatant used as the DNA template in PCR screening. Typically, 1 μl of supernatant was mixed with 20 pMols of two oligonucleotide primers, FSPT1 and 6HIS9E10R1BS1, or FSPT1 and BPB2, dNTPs to a final concentration of 200H, Taq polymerase reaction buffer, and 0.5 U of Taq polymerase in a final volume of 20 μl. The PCR incubation was carried out using 25 cycles of 94° C. for 1.5 minutes, 50° C. for 2 minutes, and 72° C. for 2 minutes, followed by a single incubation of 72° C. for 9.9 minutes at the end of the reaction.

The PCR products were analysed for DNA of the correct size (about 1000 base pairs from primers FSPTS1 to 6HIS9E10R1BS1, and about 430 base pairs from primers FSPTS1 to BPB2) by agarose gel electrophoresis. All twelve clones gave PCR DNA products of the correct size. Six of the clones were then taken for plasmid DNA preparation (using Qiagen Maxi kits, from 100 ml of over-night culture at 37° C. in L-broth with 10 μg/ml tetracycline). These plasmid DNA preparations were then sequenced over the region of PCR product insert using an USB Sequenase DNA sequencing kit, which incorporates bacteriophage T7 DNA polymerase. Alternatively the DNA was sequenced using an automated DNA sequencing service (using ABI sequencing equipment). The clones were sequenced using several separate oligonucleotide primers. Three of the primers, known as 1504, 1590 and 1731, were used to check the cloning junctions between the expression vector and the inserted gene (SEQ ID NOs: 42, 43 and 44), as well as giving sequence data from the start and end of the inserted gene. Other primers, including those known as 679, 677, 1802, and 1280 (SEQ ID NOs: 33, 34, 45 and 35) were used to confirm the remainder of the inserted gene sequence. This plasmid containing the modified mature HCPB gene is known as pICI1712. The confirmed sequence of the cloned gene, showing amino acid translation, from the start of the PelB sequence to the end of the (His)$_6$-c-myc tag is shown as SEQ ID NO: 46 with DNA numbering starting from 1 in the first codon of PelB, and peptide numbering starting from 1 in the mature HCPB.

To obtain controlled expression of the modified HCPB the pICI1712 plasmid DNA was transformed into calcium chloride transformation competent *E.coli* expression strains. Included amongst these strains were a number which were incapable of growing with arabinose as the major carbon source, and were chromosome deleted for the arabinose (Ara) operon. A preferred strain is known as HSD213 (strain MC1000 of Casadaban et al, Journal of Molecular Biology, 138, 179–208, 1980), and has the partial genotype, F⁻ Ara Δ(Ara-Leu) ΔLacX74 GalV GalK StrR. Another preferred strain is known as MSD525 (strain MC1061) and has the genotype, AraD139 Δ(Ara Leu)7697 ΔLac74 GalU HsdR RpsL. *E.coli* strains of similar genotype, suitable for controlled expression of genes from the AraB promoter in plasmid pICI266, may be obtained from The *E.coli* Genetic Stock Centre, Department of Biology, Yale University, Conn., USA. Selection for transformation was on L-agar nutrient media containing 10 μg/ml tetracycline, over night at 37° C. Single colonies were picked from the transformation plates, purified by streaking and maintained on L-agar nutrient media containing 10 μg/ml tetracycline, and grown in L-broth nutrient media containing 10 μg/ml tetracycline.

All pICI1712 transformed expression strains were treated in the same manner to test for expression of the cloned HCPB gene.

1. A single colony was used to inoculate 10 ml of L-broth nutrient media containing 10 μg/ml tetracycline in a 25 ml Universal container, and incubated over night at 37° C. with shaking.
2. 75 ml of L-broth nutrient media containing 10 μg/ml tetracycline pre-warmed to 37° C. in a 250 ml conical flask was inoculated with 0.75 ml (1% v/v) of the over-night culture. Incubation was continued at 37° C. with shaking, and growth monitored by light absorbance at 540 nm. Induction of cloned protein expression was required during exponential growth of the culture, and this was taken as between 0.4 and 0.6 O.D. at 540 nm, and generally took 90 to 150 minutes from inoculation.
3. When the cells had reached the required optical density the cultures were allowed to cool to approximately 30° C. by placing the flasks at room temperature for 30 minutes. Arabinose was then added to a final concentration of 1% (w/v), and incubation continued at 30° C. with shaking for 4 to 6 hours.
4. After incubation a final optical density measurement is taken, and the cells were harvested by centrifugation. The final O.D. measurement is used to calculate the the volume of protein acrylamide gel (Laemmli) loading buffer that is used to resuspend the cell pellet. For O.D. less than 1 a volume of 10 μl is used for each 0.1 O.D. unit, and for an O.D. greater than 1 a volume of 15 μl is used for each 0.1 O.D. unit. The Laemmli loading buffer consists of 0.125M Tris-HCl pH 6.8, containing 2% SDS, 2% β-mercaptoethanol, 10% glycerol and 0.1% Bromophenol blue.
5. Following re-suspension the samples were denatured by heating at 100° C. for 10 minutes, and then centrifuged to separate the viscous cell debris from the supernatant. Expression samples, usually 20 μl of the supernatant, typically were loaded onto 17% SDS acrylamide gels for electrophoretic separation of the proteins. Duplicate gels were generally prepared so that one could be stained for total protein (using Coomassie or similar stain and standard conditions), and the other could be processed to indicate specific products using Western analysis.

For Western analysis proteins in the run gel were transferred to nylon membrane (Problot, Applied Biosystems for example), using a semi-dry electrophoresis blotting apparatus (Bio-rad or similar). Before and during processing care was taken to ensure that the membrane remained damp. After transfer of the proteins from the gel, further binding was blocked with a solution of 5% low fat milk powder (Marvel or similar) in phosphate buffered saline (PBS) at room temperature with gentle agitation for 5 hours. The membrane was then washed 3 times at room temperature with gentle agitation for 5 minutes each time in PBS containing 0.05% Tween 20. The washed membrane was then incubated with the primary antibody, monoclonal 9E10 mouse anti-c-myc peptide (see above), at a suitable dilution (typically 1 in 10,000 for ascites or 1 in 40 for hybridoma culture supernatant) in PBS containing 0.05% Tween 20 and 0.5% low fat milk powder, at room temperature with gentle agitation over night. The membrane was then washed 3 times at room temperature with gentle agitation for at least 5 minutes each time in PBS containing 0.05% Tween 20. The washed membrane was then incubated with the secondary antibody, horseradish peroxidase labelled anti-mouse IgG (typically raised in goat, such as A4416 from Sigma), at a suitable dilution (typically 1 in 10,000) in PBS containing 0.05% Tween 20 and 0.5% low fat milk powder, at room temperature with gentle agitation for at least three hours. The membrane was then washed 3 times at room temperature with gentle agitation for at least 10 minutes each time in PBS containing 0.05% Tween 20. The membrane was then processed using the Amersham ECL Western detection kit methodology, and exposed against Amersham Hyperfilm ECL for 30 seconds in the first instance, and then for appropriate times to give a clear image of the expressed protein bands. Other methods of similar sensitivity for the detection of peroxidase labelled proteins on membranes may be used.

Good expression of the cloned tagged HCPB in pICI266 (pICI1712) was demonstrated in *E.coli* strains MSD213 and MSD525 by the Coomassie stained gels showing an additional strong protein band at about 35,000 Daltons when compared to vector (pICI266) alone clones, and a band of the same size giving a strong signal by Western analysis detection of the c-myc peptide tag.

REFERENCE EXAMPLE 8

Expression of Mature HCPB from *E.coli*

The method of cloning and expressing the mature HCPB in *E.coli* was very similar to the method described in Reference Example 7. Again pICI266 was used as the cloning vector, but in this case the starting material for PCR of the mature HCPB gene was plasmid pICI1712, the tagged gene in the expression vector. Two oligonucleotides, known as 2264 and 2265 (SEQ ID NOs: 48 and 49) were used in the PCR reactions (instead of primers FSPTS1 and 6HIS9E10R1BS1), using similar conditions to Reference Example 7, but using pICI1712 DNA instead of pICI1698. The first, top strand, oligonucleotide, 2264, was designed to prime on pICI1712 and to include the NcoI restriction enzyme site in the PelB leader sequence, and to continue to the start of the inserted mature HCPB gene (DNA bases 36 to 66 inclusive in SEQ ID NO: 46). The second, bottom strand, oligonucleotide, 2265, was designed to prime at the end of the mature HCPB gene, prior to the start of the (His)$_6$-c-myc tag sequence (complementary to DNA bases 965 to 987 inclusive in SEQ ID NO: 46), and to introduce translation termination codons (complementary to TAA TAA) at the end of the gene followed by an EcoRI (GAATTC) restriction enzyme site and fill-in bases. This oligo primes back into the gene in the PCR to isolate the mature gene sequence.

An aliquot of the PCR product was analysed for DNA of the correct size (about 970 base pairs) by agarose gel electrophoresis and found to contain predominantly a band of the correct size. The remainder of the product from the reaction mix was purified in a similar manner to Reference Example 7. The isolated DNA was restriction digested with enzymes NcoI and EcoRI, and a band of the correct size (about 940 base pairs) purified in a similar manner to Reference Example 7.

pICI266 double stranded DNA, prepared in a similar manner to Reference Example 7, was restriction digested with NcoI and EcoRI enzymes, being very careful to ensure complete digestion. DNA of the correct size (about 5600 base pairs) was purified in a similar manner to Reference Example 7.

Aliquots of both restricted and purified DNA samples were checked for purity and concentration estimation using agarose gel electrophoresis compared with known standards. From these estimates ligation mixes were prepared to clone the HCPB gene into the pICI266 vector in a similar manner to Reference Example 7.

Following the ligation reaction the DNA mixture was used to transform *E.coli* strain DH5α, colonies were picked and tested by hybridisation, in a similar manner to Reference Example 7.

Six of the clones were then taken for plasmid DNA preparation, which were then sequenced over the region of PCR product in a similar manner to Reference Example 7. The clones were sequenced using six separate oligonucleotide primers known as 1504, 1802, 679, 1280, 677 and 1731 (SEQ ID NOs: 42, 45, 33, 35, 34 and 44). From the sequencing results a clone containing a plasmid with the required mature HCPB gene sequence was selected, and is known as pICI1736.

The confirmed sequence of the cloned gene, showing amino acid translation, from the start of the PelB sequence to the EcoRI restriction site is shown as SEQ ID NO: 50 with DNA numbering starting from 1 in the first codon of PelB, and peptide numbering starting from 1 in the mature HCPB.

To obtain controlled expression of the mature HCPB, the pICI1736 μplasmid DNA was transformed into calcium chloride transformation competent *E.coli* expression strains in a similar manner to Reference Example 7. All pICI1736 transformed expression strains were treated in a similar manner to Reference Example 7 to test for expression of the cloned HCPB gene. However, in this case the 9E10 monoclonal antibody specific for the c-myc peptide tag cannot be used in the Western analysis, as the mature HCPB has no C-terminal tag. Therefore, the primary antibody was an anti-bovine carboxypeptidase A raised in rabbit (from Biogenesis) which had previously been shown to cross-react with purified human pancreatic carboxypeptidase B. the secondary antibody was an anti-rabbit IgG antibody labelled with horseradish peroxidase and raised in goat (Sigma A9169 or similar).

Expression of the cloned mature HCPB in pICI266 (pICI1736) was demonstrated in *E.coli* strains HSD213 and MSD525 by the Coomassie stained gels showing an additional protein band at about 34,000 daltons when compared to vector (pICI266) alone clones. A band of the same size gave a signal by Western analysis detection using the anti-bovine carboxypeptidase A.

REFERENCE EXAMPLE 9
Expression of Mature HCPB from COS Cells

A gene encoding preHCPB was generated by PCR from pICI1698 (Reference example 1). The PCR was set up with template pICI1689 (10 µg) and oligos SEQ ID NO 1 and SEQ ID NO 2 (100 pMoles of each) in buffer (100 µl) containing 10 mM Tris-HCl (pH8.3), 50 mM KCL, 1.5 mM MgCl$_2$, 0.125 mM each of dATP, dCTP, dGTP and dTTP and 2.5 u Taq DNA polymerase (Amplitaq, Perkin-Elmer Cetus). The reaction was overlaid with mineral oil (100 µl) and incubated at 94° C. for 1 min, 53° C. for 1 min and 72° C. for 2.5 min for 25 cycles, plus 10 min at 72° C. The PCR product of 985 bp was isolated by electrophoresis on a 1% agarose (Agarose type I, Sigma A-6013) gel followed by excision of the band from the gel and isolation of the DNA fragment by use of Geneclean (Geneclean II kit, Stratech Scientific Ltd. or Bio 101 Inc.). The Geneclean kit contains 1) 6M sodium iodide 2) a concentrated solution of sodium chloride, Tris and EDTA for making a sodium chloride/ethanol/water wash; 3) Glassmilk (TM)—a 1.5 ml vial containing 1.25 ml of a suspension of a specially formulated silica matrix in water.

This is a technique for DNA purification based on the method of Vogelstein and Gillespie published in Proceedings of the National Academy of Sciences USA (1979) Vol 76, p 615. Alternatively any of the methods described in "Molecular Cloning—a laboratory manual" Second Edition, Sambrook, Fritsch and Maniatis (Cold Spring Harbor Laboratory, 1989) can be used. Briefly, the Geneclean procedure is as follows. To 1 volume of gel slice is added 3 volumes of sodium iodide solution from the kit. The agarose is melted by heating the mix at 55° C. for 10 min then Glassmilk (5–10 µl) is added, mixed well and left to stand for 10 min at ambient temperature. The glassmilk is spun down and washed 3 times with NEW WASH (500 µl) from the kit. The wash buffer is removed from the Glassmilk which is to dry in air. The DNA is eluted by incubating the dried Glassmilk with water (5–10 µl) at 55° C. for 5–10 min. The aqueous supernatant containing the eluted DNA is recovered by centrifugation. The elution step can be repeated and supernatants pooled.

The preHCPB gene was digested for 1 h at 37° C. with EcoRI and HindIII in a 100 µl reaction containing 100 mM Tris-HCl (pH 7.5), 10 mM magnesium chloride, 50 mM NaCl, 0.025% triton X-100, and 25 u each of HindIII and EcoRI (New England Biolabs). The digested fragment was purified by agarose gel electrophoresis and GeneClean as described above for the uncut fragment and cloned into pBluescript (Stratagene Cloning Systems).

pBluescript KS+ DNA (5 µg) was digested to completion with EcoRI and HindIII (25 u each) in a 100 µl reaction as described above. Calf-intestinal alkaline phosphatase (1 µl; New England Biolabs, 10 u/µl) was the added to the digested plasmid to remove 5' phosphate groups and incubation continued at 37° C. for a further 30 minutes. Phosphatase activity was destroyed by incubation at 70° C. for 10 minutes. The EcoRI-HindIII cut plasmid was purified from an agarose gel as described above. The EcoRI-HindIII digested preHCPB gene (50 ng) was ligated with the above cut plasmid DNA in 20 µl of a solution containing 30 mM Tris-Hcl (pH7.8), 10 mM MgCl$_2$, 10 mM DTT, 1 mM ATP, 50 µg/ml BSA and 400 u T4 DNA ligase (New England Biolabs, Inc) at 25° C. for 4 h. A 1 µl aliquot of the reaction was used to transform 20 µl of competent *E.coli* DH5α cells (MAX efficiency DH5α competent cells, Life Technologies Ltd) using the protocol provided with the cells. Transformed cells were plated onto L-agar plus 100 µg/ml Ampicillin.

Potential preHCPB clones were identified by PCR. Each clone was subjected to PCR as described above for preparation of the preHCPB gene except that the mix with the cells was incubated at 94° C. (hot start procedure) for 5 min prior to 25 cycles of PCR and oligos SEQ ID NOs 3 and 4 replace oligos SEQ ID NOs 1 and 2. A sample (10 µl) of the PCR reaction was analysed by electrophoresis on a 1% agarose gel. Clones containing the preHCPB gene were identified by the presence of a 1.2 kb PCR product. Clones producing the 1.2 kb were used for large scale plsamid DNA preparation and the sequence of the insert confirmed by DNA sequence analysis. The plasmid containing the preHCPB gene in pBluescript was named pMF15.

To generate vectors capable of expressing HCPB in eukaryotic cells the GS-System(™) system (Celltech Biologics) was used (WO 87/04462, WO 89/01036, WO 86/05807 and WO 89/10404). The procedure requires cloning the preHCPB gene into the HindIII-EcoRI region of vector pEE12 [this vector is similar to pSV2.GS described in Bebbington et al. (1992) Bio/Technology 10, 169–175, with a number of restriction sites originally present in pSV2.GS removed by site-directed mutagenesis to provide unique sites in the multi-linker region]. To construct the expression vector, plasmids pEE12 and pMF15 were digested with EcoRI and HindIII as described above. The appropriate vector (from pEE12) and insert (from pMF15) from each digest were isloated from a 1% agarose gel and ligated together and used to transform competent DH5α cells. The transformed cells were were plated onto L agar plus ampicillin (100 µg/ml). Colonies were screened by PCR as described above, with oligos which prime within the CMV promoter (SEQ ID NO 5) and in the HCPB gene (SEQ ID NO 6). Clones producing a 1.365 kb PCR product were used for large scale plasmid DNA preparation and the sequence of the insert confirmed by DNA sequence analysis. The plasmid containing the preHCPB sequence in pEE12 was named pMF48.

A second eukaryotic expression plasmid, pEE12 containing the prepro sequence of preproHCPB was prepared as described above. Oligos SEQ ID NOs 7 and 8 were used in the initial PCR to isolate a gene for the prepro sequence from pMF18 (described in Reference Example 11). In this case the PCR was performed with a hot start procedure by first incubating the mix without Taq DNA polymerase for 5 min at 94° C. Taq DNA polymerase (2.5 u) was then added and the PCR continued through the 25 cycles as described above. The 360 bp fragment was clone into pBluescript to give pMF66 and subsequently into pEE12 (screening by PCR with SEQ ID NOS 7 and 8) to give pMF67.

For expression in eukaryotic cells, vectors containing genes capable of expressing preHCPB and the prepro sequence were cotransfected into COS-7 cells. COS cells are an African green monkey kidney cell line, CV-1, transformed with an origin-defective SV40 virus and have been widely used for short-term transient expression of a variety of proteins because of their capacity to replicate circular plasmids containing an SV40 origin of replication to very high copy number. There are two widely available COS cell clones, COS-1 and COS-7. The basic methodology for transfection of COS cells is described by Bebbington in Methods: A Companion to Methods in Enzymology (1991) 2, p. 141. For expression of HCPB, the plasmid vectors pMF48 and pMF67 (4 µg of each) were used to transfect the COS-7 cells (2×10$^5$) in a six-well culture plate in 2 ml Dulbecco's Modified Eagle's Medium (DMEM) containing 10% heat inactivated foetal calf serum (FCS) by a method known as lipofection—cationic lipid-mediated delivery of polynucleotides [Felgner et al. in Methods: A Companion to Methods in Enzymology (1993) 5, 67–75]. The cells were incubated at 37° C. in a $CO_2$ incubator for 20 h. The mix of plasmid DNA in serum-free medium (20 µl; OPTI-MEM Reduced Serum Medium; GibcoBRL Cat. No. 31985) was mixed gently with LIPOFECTIN reagent (12 µl; GibcoBRL Cat. No. 18292-011) and incubated at ambient temperature for 15min. The cells were washed with serum-free medium (2 ml; OPTI-MEN). Serum-free medium (600 µl; OPTI-MEM) was added to the DNA/LIPOFECTIN and the mix overlaid onto the cells which were incubated at 37° C. for 6 h in a $C_2O$ incubator. The DNA containing medium was replaced with normal DMEM containing 10% FCS and the cells incubated as before for 72 h. Cell supernatants (250 µl) were analysed for HCPB activity against Hipp-Arg (5 h assay) as described in Reference Example 3. COS cell supernatants which had been treated with LIPOFECTIN reagent, but without plasmid DNA, hydrolysed 1.2% of the substrate, whereas the COS cell supernatants transfected with the mix of plasmids expressing preHCPB and prepro sequence hydrolysed 61% of the Hipp-Arg substrate. COS cells transfected with only the preHCPB plasmid hydrolysed Hipp-Arg at the level seen for COS cells which had been treated with LIPOFECTIN reagent alone.

LIPOFECTIN Reagent is a 1:1 (w/w) liposome formulation of the cationic lipid N-[1-(2,3-dioleyloxy)propyl]-n,n, n-trimethylammonium chloride (DOTMA) and dioleoyl phosphatidylethanolamine (DOPE) in membrane filtered water. It binds sponaneously with DNA to form a lipid-DNA complex see Felgner et al. in Proc. Natl. Acad. Sci. USA (1987) 84, 7431.

REFERENCE EXAMPLE 10

Expression of proHCPB from E.coli

The method of cloning and expressing the pro-HCPB in E.coli was very similar to the method described in Reference Example 7. Again pICI266 was used as the cloning vector, and the starting material for PCR of the pro-HCPB gene was plasmid pICI1698 (as described in Reference Example 6). Two oligonucleotides, known as 2310 and 2265 (SEQ ID NOs: 52 and 49) were used in the PCR reactions (instead of primers FSPTS1 and 6HIS9E10R1BS1), using similar conditions to Reference Example 7.

The first, top strand, oligonucleotide, 2310, was designed to prime on pICI1698, and to add the NcoI restriction enzyme site from the PelB leader sequence (DNA bases 51 to 66 inclusive in SEQ ID NO: 46) to the start of the inserted pro-HCPB gene (DNA bases 40 to 57 inclusive in SEQ ID NO: 38). The second, bottom strand, oligonucleotide, 2265, was designed to prime at the end of the mature HCPB gene, prior to the start of the $(His)_6$-c-myc tag sequence (complementary to DNA bases 965 to 987 inclusive in SEQ ID NO: 46), and to introduce translation termination codons (complementary to TAA TAA) at the end of the gene followed by an EcoRI (GAATTC) restriction enzyme site and fill-in bases. This oligo primes back into the gene in the PCR to isolate the pro-gene sequence.

An aliquot of the PCR product was analysed for DNA of the correct size (about 1240 base pairs) by agarose gel electrophoresis and found to contain predominantly a band of the correct size. The remainder of the product from the reaction mix was purified in a similar manner to Reference Example 7. The isolated DNA was a restriction digested with enzymes NcoI and EcoRI, and a band of the correct size (about 1210 base pairs) purified in a similar manner to Reference Example 7.

pICI266 double stranded DNA, prepared in a similar manner to Reference Example 7, was restriction digested with NcoI and EcoRI enzymes, being very careful to ensure complete digestion. DNA of the correct size (about 5600 base pairs) was purified in a similar manner to Reference Example 7.

Aliquots of both restricted and purified DNA samples were checked for purity and concentration estimation using agarose gel electrophoresis compared with known standards. From these estimates ligation mixes were prepared to clone the pro-HCPB gene into the pICI266 vector in a similar manner to Reference Example 7.

Following the ligation reaction the DNA mixture was used to transform E.coli strain DH5α, colonies were picked and tested by hybridisation, in a similar manner to Reference Example 7.

Four positive hybridisation isolates were checked by PCR for inserts of the correct size, using primers 2310 and 2265, (SEQ ID NOs: 52 and 49), and for priming with a pair of internal primers 1279 (SEQ ID NO: 36) and 679 (SEQ ID NO: 33) in a similar manner to Reference Example 7. The PCR products were analysed for DNA of the correct size (about 1200 base pairs from primers 2310 to 2265, and about 580 base pairs from primers 1279 to 679) by agarose gel electrophoresis. All clones gave PCR DNA products of the correct size.

All four of the clones were then taken for plasmid DNA preparation, and were then sequenced over the region of PCR product in a similar manner to Reference Example 7. The clones were sequenced using six separate oligonucleotide primers known as 1504, 1802, 679, 1281, 1590 and 1592 (SEQ ID NOs: 42, 45, 33, 37, 53 and 54). From the sequencing results a clone containing a plasmid with the required pro-HCPB gene sequence was selected, and is known as pICI1738.

The confirmed sequence of the cloned pro-HCPB gene in pICI1738, showing amino acid translation, from the start of the PelB sequence to the EcoRI restriction site is shown as SEQ ID NO: 55 with DNA numbering starting from 1 in the first codon of PelB, and peptide numbering starting from 1 in the mature HCPB.

To obtain controlled expression of the pro-HCPB the pICI1738 plasmid DNA was transformed into calcium chloride transformation competent E.coli expression strains in a similar manner to Reference Example 7. All pICI1738 transformed expression strains were treated in a similar manner to Reference Example 7 to test for expression of the cloned HCPB gene. However, in this case the 9E10 monoclonal antibody specific for the c-myc peptide tag cannot be used in the Western analysis, as the pro-HCPB has no C-terminal tag. Therefore, the primary antibody was an anti-bovine carboxypeptidase A raised in rabbit (from Biogenesis) which had previously been shown to cross-react with purified human pancreatic carboxypeptidase B. The secondary antibody was an anti-rabbit IgG antibody labelled with horseradish peroxidase and raised in goat (Sigma A0545 or similar).

Expression of the cloned pro-HCPB in pICI266 (pICI1738) was demonstrated from E.coli by the Coomassie stained gels showing an additional protein band at about 40,000 Daltons when compared to vector (pICI266) alone clones, and clones producing the tagged HCPB (Reference Example 7). A band of the same size gave a signal by Western analysis detection using the anti-bovine carboxypeptidase A.

REFERENCE EXAMPLE 11

Expression of proHCPB from COS Cells

A gene for preproHCPB was prepared by PCR as described in Reference Example 9 using as template pICI1689 and oligos SEQ ID NOS 1 and 7 to give a 1270 bp PCR product. The gene was digested with EcoRI and HindIII and cloned initially into pBluescript KS+ (to give pMF18) then into pEE12 in DH5α (to give pMF49) as described in Reference Example 9. Plasmid pMF49 was transfected into COS-7 cells by use of LIPOFECTIN reagent as described in Reference Example 9 and cell supernatants (250 μl) assayed for HCPB activity against Hipp-Arg (5 h assay), as described in Reference Example 3, following activation with trypsin (700 μg/ml) in 50 mM Tris-Hcl (pH7.6), 150 mM NaCl at 4° C. for 1 h. Under these condition, complete hydrolysis of the Hipp-Arg substrate was achieved, whereas supernatant from COS cells which had been treated with LIPOFECTIN reagent alone (without plasmid DNA) when activated with trypsin hydrolysed 30% of the Hipp-Arg substrate.

REFERENCE EXAMPLE 12
Purification of Native HCPB

A system has been determined for the initial purification of the native and the different mutant enzymes via two routes.

The preferred route is described first. Recombinant *E.coli* cell paste containing the recombinant enzyme was taken from storage at −70° C. and allowed to thaw. The weight of cell paste was measured in grams and the paste resuspended with the addition of buffer A (200 mM Tris (hydroxymethyl) aminomethane hydrochloride (TRIS-HCl), 20% sucrose, pH 8.0) to a volume equal to the initial weight of the cell paste. The cell suspension was incubated at room temperature for 20 minutes with occasional gentle mixing before an equal volume of distilled water was added and thoroughly mixed in. The cell suspension was again incubated at room temperature for 20 minutes with occasional gentle mixing. The resulting crude osmotic shockate was clarified by centrifugation at 98000×g for 90 minutes at 4° C. after which the supernatant was decanted off from the pelleted insoluble fraction. Deoxyribonuclease 1 was added to the supernatant to a final concentration of 0.1 mg/ml The mixture was incubated at room temperature, with continuous shaking, until the vicosity was reduced enough for it to be loaded on to a Carboxypeptidase Inhibitor CNBr activated Sepharose affinity column,prepared according to instructions with the CNBr activated Sepharose 4B from Pharmacia and carboxypeptidase inhibitor from potato tuber (c-0279, Sigma). The supernatant was adjusted to pH8.0 and loaded on to the affinity column, pre-equilibrated with 10 mM TRIS-HCl, 500 mM sodium chloride, pH 8.0. After loading the supernatant the column was washed until the absorbance of the flow through was back to baseline before the bound material was eluted from the column by elution buffer (100 mM sodium carbonate, 500 mM sodium chloride, pH 11.4). The eluted fractions were frozen at −20° C. whilst those containing the recombinant carboxypeptidase were determined by Western blot analysis using an anti-c-myc tag antibody (9E10), followed by an anti-mouse -horse raddish peroxidase conjugate (a-9044, sigma) that gave a colour reaction with exposure to 4-chloro-naphthol and hydrogen peroxide.

Fractions containing the recombinant carboxypeptidase B were pooled, concentrated and the pH adjusted to pH 7.5 before being snap-frozen and stored at −20° C. Further purification of the pooled sample, utilising known methods such as ion exchange and gel permeation chromatography may performed if required.

The second route involves the total lysis of the *E.coli* cells as opposed to a periplasmic shock, as used in the preferred route.

Recombinant *E.coli* cell paste containing the recombinant enzyme was taken and resuspended in lysis buffer (50 mM TRIS-HCl, 15% Sucrose, pH 8.0). Lysozyme was added to a concentration of 1 mg/ml and at the same time lithium dodecyl sulphate (LDS) was added (80 μl of a 25% solution per 25 ml of suspension). The suspension was incubated on ice for 30 minutes with occasional shaking, followed by the addition deoxyribonuclease 1 to a concentration of 1 mg/ml and again the suspension was incubated on ice for 30 minutes with occasion shaking. The suspension was subsequently divided in to 200 ml volumes and sonicated to complete the disruption of the cells for 10×30 sec bursts with 30 sec intervals between bursts. Sonicated suspensions were centrifuged at 98,000×g for 90 minutes at 4° C. after which the supernatant was decanted off from the pelleted insoluble fraction. The supernatant was adjusted to pH 8.0 and loaded on to the affinity column, pre-equilibrated with 10 mM TRIS-HCl, 500 nm sodium chloride, pH 8.0. After loading the supernatant the column was washed until the absorbance of the flow through was back to baseline before the bound material was eluted from the column by elution buffer (100 mM sodium carbonate, 500 mM sodium chloride, pH 11.4). The eluted fractions were frozen at −2° C. whilst those containing the recombinant carboxypeptidase were determined by western blot analysis using an anti-c-myc tag antibody (9E10), followed by an anti-mouse -horse raddish peroxidase conjugate (a-9044, sigma) that gave a colour reaction with exposure to 4-chloronaphthol and hydrogen peroxide. Fractions containing the recombinant carboxypeptidase B were pooled, concentrated and the pH adjusted to pH 7.5 before being snap-frozen and stored at −20° C. Further purification of the pooled sample, utilising known methods such as ion exchange and gel permeation chromatography may performed if required.

Samples of the pooled material from both routes, analysed by SDS-PAGE and Coomassie stained nitrocellulose blot provided Coomassie stained bands at the correct molecular weight for the recombinant carboxypeptidase B's. These bands sequenced by an automated protein/peptide sequencer using the Edman degradation technique gave positive matches for the particular recombinant carboxypeptidase B being purified.

REFERENCE EXAMPLE 13
Expression of Murine A5B7 F(ab')$_2$-HCPB Fusion Protein from COS Cells A particular antibody capable of binding with a tumour associated antigen is mouse monoclonal antibody A5B7. Antibody A5B7 binds to human carcinoembryonic antigen (CEA) and is particularly suitable for targeting colorectal carcinoma. A5B7 is available from DAKO Ltd., 16 Manor Courtyard, Hughenden Avenue, High Wycombe, Bucks HP13 5RE, England, United Kingdom. Antibody fragments can be prepared from whole IgG antibody by conventional means such as for example F(ab')$_2$ fragments as described by Mariani, M. et al (1991), Molecular Immunology 28, 69–77. In general the antibody (or antibody fragment)—enzyme conjugate should be at least divalent, that is to say capable of binding to at least 2 tumour associated antigens (which may be the same or different). Antibody molecules may be humanised by known methods such as for example by "CDR grafting" as disclosed in EP239400 or by grafting complete variable regions onto human constant regions as disclosed in U.S. Pat. No. 4,816,567. Humanised antibodies may be useful for reducing immunogenicity of an antibody (or antibody fragment). A humanised version of antibody A5B7 has been disclosed in PCT WO92/01059.

The hybridoma which produces monoclonal antibody A5B7 was deposited with the European Collection of Animal Cell Cultures, Division of Biologics, PHLS Centre for Applied Microbiology and Research, Porton Down, Salisbury, Wiltshire SP4 OJG, United Kingdom. The date of deposit was Jul. 14th 1993 and the accession number is No. 93071411. Antibody A5B7 may be obtained from the deposited hybridoma using standard techniques known in the art such as documented in Fenge C, Fraune E & Schuegerl K in "Production of Biologicals from Animal Cells in Culture" (Spier R E, Griffiths J R & Meignier B, eds) Butterworth-Heinemann, 1991, 262–265 and Anderson B L & Gruenberg M L in "Commercial Production of Monoclonal Antibodies" (Seaver S, ed), Marcel Dekker, 1987, 175–195. The cells may require re-cloning from time to time by limiting dilution in order to maintain good levels of antibody production.

This example describes the preparation of cDNA from the A5B7 hybridoma, the isolation of specific Fd and light chain fragments by PCR, determination of the complete DNA sequence of these fragments, the subsequent preparation of an Fd-HCPB fusion gene and a co-expression vector capable of producing both light chain and Fd-HCPB fusion protein in eukaryotic cells, expression of the F(ab')$_2$-HCPB from COS cells by co-transfection with a prepro sequence from HCPB.

a) Preparation of mRNA from Hybridoma Cells

There are several procedures for the isolation of polyA+ mRNA from eukaryotic cells (Sambrook J., Fritsch E. F., Maniatis T., Molecular Cloning: A Laboratory Manual, Cold Spring Harbor Laboratory Press, Second Edition, 1989, Chapter 8 p3 hereinafter referred to as Maniatis). One such method is provided in kit form by Pharmacia and relies on the lysis of a relatively small number of cells ($10^7$ or less) followed by binding of polyA+ mRNA to an oligo dT column. Unwanted cell components are removed by washing with a low salt concentration before eluting the mRNA in high salt solution at elevated temperature. mRNA was prepared from $10^7$ A5B7 hybridoma cells using the Quickprep mRNA kit (Pharmacia Biotechnology Ltd.). The concentration of the mRNA was estimated by scanning a sample from 300–220 nm in a Uvikon 930 spectrophotometer (Kontron Instruments) and using an extinction coefficient of 40 µg/ml at 260 nm. The mRNA was stored as 2.5 µg aliquots precipitated in ethanol.

b) cDNA Synthesis

The method used for cDNA synthesis was based on that of Gubler and Hofman which relies on reverse transcription from primed mRNA followed by RNAse H treatment to provide priming and synthesis of the second strand by DNA polymerase I. Other methods for the synthesis of cDNA are reviewed in Maniatis (Chapter 8).

A 5 µg sample of mRNA was primed with oligo dT (12–18 mer mixture, Pharmacia Biotechnology Ltd., 0.5 µg) in a 10 µl solution containing 2.5 u placental RNAse inhibitor (Life Technologies Ltd.) made up with RNAse-free water by incubating at 70° C. followed by cooling on ice. First strand cDNA synthesis was then performed by adding 4 µl 5×H-RT buffer (250 mM Tris, pH8.3, 200 mM KCl, 30 mM MgCl$_2$ and 0.5 mg/ml BSA), 2 µl 0.1M DTT (dithiothreitol), 1 µl dNTP mix (dATP,dCTP,dGTP and dTTP at 20 mm), 4 µl Superscript Reverse transcriptase (Life Technologies Ltd.) and incubating at 42° C. for 1 hour. For the second strand reaction, 1.5 µl dNTP mix (as above), 92.5 µl RNAse-free water, 30 µl 5×reaction buffer (125 mM Tris, pH7.5, 500 mM KCl, 25 mM MgCl2 50 mM (NH$_4$)$_2$S$_4$ and 0.5 mg/ml β-NAD), 1 µl T4 DNA ligase (10 u, Life Technologies Ltd.), 4 µl DNA polymerase I (40 u, Life Technologies Ltd.) and 1 µl RNAse H (2.7 u, Life Technologies Ltd.) were added and incubation continued at 16° C. for a further 2 hours. To ensure that blunt-ended cDNA was prepared a final incubation at 16° C. for 5 minutes after adding 2 µl T4 DNA polymerase (10 u, Life Technologies Ltd.) was performed. Enzyme activity was then stopped by incubation at 70° C. for 10 minutes.

c) Isolation of Antibody Gene Fragments by PCR

Isolation of A5B7 Fd and L chain fragments was performed using the cDNA as template. The Fd fragment was terminated immediately after the hinge sequence (c-terminal threonine) hereinafter referred to as proteolytic type Fd.

Material from the first-strand cDNA reaction or after completion of the second strand reaction is suitable as template. The material could be used neat from the completed reaction or as a dilution (up to 1 in 100) in double-distilled water. Oligonucleotides (SEQ ID numbers 13–19) were used in the generation of the Fd and L chain fragments. For each antibody fragment, the 5' region oligonucleotide (SEQ ID 13 for Fd fragment and SEQ ID 14 for the L chain) encoded a restriction enzyme site (HindIII for Fd and EcoRI for L chain) a consensus Kozak sequence (GCCGCCACC) to maximise translation initiation and a portion of the natural murine signal sequence. The 3' region oligonucleotide for the proteolytic type Fd fragment (SEQ ID 15 was complementary to the 3' end of the antibody hinge region, encoded mutations to introduce tandem translation termination codons (TAG and TAA) immediately after the hinge and contained an EcoRI restriction enzyme site beyond this sequence. The 3' region of the L chain was determined by an oligonucleotide (SEQ ID 16) complementary to the end of the coding region, introduced an additional translation termination codon (TAA) and an EcoRI restriction site. In addition pairs of partially overlapping and complementary oligonucleotides for each fragment (SEQ IDS 17 and 18 for the Fd and SEQ IDS 19 and 65 for the L chain) were used to introduce silent mutations into each DNA strand resulting in the removal of a BamHI from the CH1 of the Fd fragment and the VL of the L chain without altering the encoded amino-acid sequence. Each 5' and 3' oligonucleotide was used with the appropriate mutagenic oligonucleotide to generate 2 mutated fragments of each antibody chain. After purification the two fragments were mixed in equal proportions and used as the templates for a second PCR reaction using the relevant 5' and 3' region oligonucleotides. The products of these reactions were the full-length Fd and L chain fragments without internal BamHI sites.

In general, 5 µl of cDNA was added to a 100 µl reaction containing 10 mM Tris-HCl, pH 8.3, 50 mM KCl, 0.1% gelatin, 1.5 mM MgCl2, 1.25 mM each of dATP, dCTP, dGTP and dTTP, 1 µM each of an appropriate oligo pair and 2.5 u Taq DNA polymerase (Amplitaq, Perkin-Elmer Cetus). Each reaction was overlaid with 100 µl mineral oil and incubated at 94° C. for 1.5 minutes, 50 or 55° C. for 1.0 minute and 72° C. for 2.0 minutes for 25 cycles plus 10 minutes at 72° C. Control reactions with no DNA were also set up.

The PCR reactions were analysed by running a 5 µl sample of each on a 0.8% agarose (Sigma Chemical Company Ltd.) gel which was subsequently stained in 1 µg/ml Ethidium Bromide (BDH Laboratory Supplies) solution and the DNA visualised on a UV transilluminator. Bands of the appropriate size were visible in all PCRs with A5B7 cDNA present indicating successful amplification of the fragments of the Fd and L chains. The absence of a DNA band in the control reactions indicated that the reagents used did not contain contaminating DNA.

Each PCR product was purified by use of a Centricon 100 filtration microconcentrator (Amicon Ltd.). Each reaction was added to a concentrator and the volume increased to 2 ml by addition of double distilled water. The unit was then centrifuged at 500×g (Sorval RT6000B benchtop centrifuge with H1000B rotor) for 5 minutes and the "flow-through" discarded. The retentate was diluted to 2 ml again and the unit re-centrifuged. The process was repeated for a third time. This procedure results in the removal of excess oligos and buffer components from the amplified DNA. These purified DNAs were then used directly in subsequent PCR reactions. The appropriate pairs of fragments were mixed in equal proportions and aliquots used in the second PCRs with the respective 5' and 3' oligonucleotides.

d) Subcloning the PCR Generated Fragments Into pBluescript

The products of the second PCR reactions showed bands of approximately 775 bp and 730 bp consistent with the full-length Fd and L chains respectively. These products were also purified using Centricon 100 microconcentrators as above. Each DNA product was then precipitated in a 1.5 ml solution containing 50 µl 3M sodium acetate, distilled water to 500 µl and 1 ml of absolute ethanol. The solution was incubated on ice for at least 10 minutes before centrifugation at 11,600×g for 10 minutes (MSE MicroCentaur). The supernatant was discarded and the pellet washed in 1 ml 70% ethanol (v/v in distilled water) by centrifugation for a further 5 minutes. The supernatant was discarded and the DNA pellet dried under vacuum. Each DNA pellet was resuspended in distilled water. The Fd PCR product was then digested with EcoRI and HindIII in a 200 µl reaction containing 20 mM Tris-acetate, pH 7.9, 10 mM magnesium acetate, 50 mM potassium acetate, 1 mM dithiothreitol (DTT), and 25 u each of HindIII and EcoRI (Promega Corporation). The L chain product was digested with EcoRI in a 30 µl reaction containing 90 mM Tris-HCl, pH7.5, 10 mM magnesium chloride, 50 mM sodium chloride and 10 u EcoRI. Digests were incubated at 37° C. for 1 hr.

The digested fragments were then purified by electrophoresis on a 0.75% SeaPlaque GTG agarose gel (FMC BioProducts Ltd) followed by excision of the appropriate bands from the gel. The agarose gel slice was redissolved by incubation at 65° C. for 2 minutes, diluted to a final volume of 450 µl with distilled water and 50 µl 3M sodium acetate added. This solution was extracted with an equal volume of liquified phenol, equilibrated with Tris buffer pH7.6 (Fisons Scientific Equipment) using centrifugation at 11,600×g for 2 minutes (MSE MicroCentaur) to separate the aqueous and phenolic phases. The subsequent aqueous phase was re-extracted with a phenol:chloroform mixture (50:50 v:v) and again with chloroform prior to ethanol precipitation as described above. Each purified pellet was resuspended in 10 µl distilled water and a 1 µl sample visualised by electrophoresis on a 0.8% agarose gel to estimate quality and concentration.

pBluescript (Stratagene Cloning Systems) was used for initial cloning of Fd and L chain cDNAs. This phagemid vector has unique EcoRI and HindIII cloning sites, Ampicillin resistance gene, and both ColEI and fI replication origins for isolation of either double- or single stranded DNA. 5 µg pBluescript KS-DNA was digested to completion with 30 u EcoRI (Promega Corporation) in a 100 µl reaction containing 90 mM Tris-HCl, pH7.5, 10 mM MgCl2, 50 mM NaCl or with EcoRI and HindIII in a 100 µl reaction containing 20 mM Tris-acetate, pH 7.9, 10 mM magnesium acetate, 50 mM potassium acetate, 1 mM dithiothreitol (DTT), and 25 u each of EcoRI and HindIII (Promega Corporation) at 37° C. for 1 hour. 2 µl calf-intestinal alkaline phosphatase (2 u, Bohringer Mannheim) was the added to the EcoRI digested plasmid to remove 5' phosphate groups and incubation continued at 37° C. for a further 30 minutes. Phosphatase activity was destroyed by incubation at 70° C. for 10 minutes. The EcoRI-HindIII cut plasmid was purified from a SeaPlaque GTG agarose gel as described above.

25–50 ng of digested Fd or L chain PCR product was ligated with 50 ng of EcoRI-HindII or EcoRI/CIP treated pBluescript respectively in 10 µl of a solution containing 30 mM Tris-HCl, pH7.8, 10 mM MgCl$_2$, 10 mM DTT, 1 mM ATP and 1.5 u T4 DNA ligase (Promega Corporation) at 16° C. for 2.5 hours. A 1 µl aliquot of each reaction was used to transform 20 µl of competent E.coli DH5α cells (Life Technologies Ltd.) using the protocol provided with the cells. Transformed cells were plated onto L-agar plus 100 µg/ml Ampicillin, 1 mM IPTG and 0.2% X-gal and incubated overnight at 37° C. Clones containing cloned inserts were selected on the basis of producing white colonies on the above medium-compared to the blue colour generated by cells containing the parental plasmid.

e) DNA Sequence Analysis of cDNA Clones

The potential Fd and L chain cDNA clones identified by colour selection were picked from the agar plates and used for large scale plasmid DNA preparation. Each clone was used to inoculate 200 ml of L-broth plus 100 µg/ml ampicillin in a 500 ml conical flask. The cultures were incubated, shaking at 37° C. overnight. After growth the cells from each culture were pelleted by centrifugation at 5000×g for 10 minutes in a Sorvall RC5 C centrifuge and GS3 rotor at 4° C. The cell pellet from each culture was resuspended in 20 ml TE buffer and re-centrifuged at 2000×g for 10 minutes in a Sorvall RC5C centrifuge and SS-34 rotor in an oak-ridge tube at 4° C. Each washed cell pellet was resuspended in 3 ml ice cold 25% sucrose, 50 mM Tris, pH8.0, and left on ice. Fresh lysozyme solution (1.0 ml at 10 mg/ml) was added, the contents mixed by rolling the tube and incubation on ice continued for 5 minutes. Sodium ethylene diamine tractetate (EDTA) solution (1.0 ml at 0.5 mM, pH8.5) was added and the contents gently mixed. Finally, 5.0 ml of iced Triton X solution (0.1% Triton X-100, 62.5 mM EDTA, 50 mM Tris, pH8.0) was added, the contents gently mixed and incubation on ice continued for a further 10 minutes. The cell debris was then pelleted by centrifugation at 39,000×g for 30 minutes in a Sorvall RC5C centrifuge and SS-34 rotor at 4° C. The supernatant containing plasmid DNA was added to 16 g caesium chloride (Boehringer Mannheim) and 150 µl ethidium bromide solution (10 mg/ml) and the volume increased to 18.5 ml by addition of TE buffer. This solution was transferred to an 18.5 ml crimp top, polypropylene centrifuge tube (Sorvall Instruments). The tube was sealed and centrifuged at 180,000×g for 16 hours in a Sorvall TV865B (titanium, vertical) rotor and OTD65B centrifuge at 18° C.

After centrifugation, plasmid DNA was visible as a distinct orange band in the CsCl/EtBR density gradient which had formed. The plasmid DNA was removed from the gradient using a hypodermic syringe to pierce the tube wall. The sample taken from the gradient was diluted 3–4 fold with TE buffer and the DNA precipitated by addition of an equal volume of isopropyl alcohol and incubation on ice for 10 minutes. The precipitated DNA was pelleted by centrifugation at 17,000×g in a Sorvall RC5C centrifuge and SS-34 rotor at 4° C. and the supernatant discarded. The resulting pellet was washed in 70% ethanol (v/v) and re-centrifuged for 5 minutes. The pellet was then dried under vacuum, resuspended in 1.8 ml TE buffer and 200 µl 3H sodium acetate solution and extracted with an equal volume of phenol using centrifugation at 17,000×g for 2 minutes to separate the phases. The aqueous phase was re-extracted against an equal volume of chloroform before precipitating the DNA by addition of an equal volume of ethanol at −20° C. and incubating on ice for 10 minutes. The purified DNA was pelleted as above, washed in 5 ml 70% ethanol and the pellet vacuum dried. The dried pellet was resuspended in 500 µl double-distilled water and DNA concentration estimated by scanning a diluted sample from 300 to 220 nm in a UV spectrophotometer using and extinction coefficient of 50 µg/ml/OD260. A number of proprietary kits, e.g. Qiagen (Hybaid Ltd), are also available for plasmid DNA purification.

This purified plasmid DNA was then used for DNA sequence analysis. Double stranded DNA can be used for DNA sequence analysis by the dideoxy chain termination method of Sanger (Proc.Nat.Acad.Sci. USA 74, 1977, p5463) using a proprietary sequencing kit such as the Sequenase kit supplied by United States Biochemical Company and used in accordance with the protocols provided.

Aliquots (2–4 µg) of Fd and L chain cDNA clone plasmid DNA were used for DNA sequence analysis. Each aliquot was initially denatured by incubation with 0.2M NaOH, 0.2 mM EDTA in a final volume of 100 µl at room temperature for 10 minutes. The denatured DNA was then precipitated by addition of 10 µl 3M sodium acetate (pH5.0) and 275 µl ethanol and incubation on ice for 10 minutes. The precipitated DNA was recovered as described for plasmid DNA above. The denatured DNA was then primed for sequencing by incubation of each with 0.5 pmoles of an appropriate primer in 10 µl of Sequenase reaction buffer (40 mM Tris, pH7.5, 25 mM $MgCl_2$, 50 mM NaCl) containing 10% di-methyl sulphoxide (DMSO) at 65° C. for 2 minutes followed by gradual cooling to below 30° C. These primed templates were then used in sequencing reactions according to the protocols provided with 10% DMSO added to labelling and termination mixtures.

The sequencing reactions were analysed by autoradiography after high resolution electrophoresis on a 6% polyacrylamide: 8M urea denaturing gel (Sanger and Coulson, 1978, FEBS lett.87, p107).

The complete Fd and L chain sequences of the cloned cDNAs are given below (SEQ ID NO 20 for the proteolytic type Fd chain and SEQ ID NO 22 for L chain). The plasmid containing the proteolytic type Fd was named pAF1 and the L chain pAF3. The presence of the silent mutation in each fragment for removal of the BamHI site was also confirmed. The DNA sequence indicates that the antibody is an $IgG1_K$ isotype when compared to published constant region DNA sequence data (in Kabat, E. A., Wu, T. T., Bilofsky, H., Reid-Milner, M., Perry, H., 1987, Sequences of Proteins of Immunological Interest, Fourth Edition, Public Health Service N.I.H. Washington DC).

f) Preparation of Fd-HCPB Fusion DNA Sequence

A gene encoding the C-terminal region of the Fd sequence, from the NcoI site in SEQ ID NO 20 (position 497) was joined to the HCPB sequence by PCR. In this process DNA for an 8 amino-acid linker sequence (VPEVSSVF; SEQ ID NO: 67) was introduced. Plasmid pAF1 was subjected to PCR (hot start procedure) as described in Reference Example 9 with oligos SEQ ID NOS 9 and 10 to give a 338 bp product. Similarly, pICI1698 was subjected to PCR with oligos SEQ ID NOS 11 and 1 to give a 998 bp product. Both products were isolated by agarose gel electrophoresis and Geneclean as described in Reference Example 9 and used (0.2 ng each in 50 µl total volume) in a second hot start PCR with 10 cycles for 1 min at 94° C. and 4 min at 63° C. followed by 2 min at 94° C. Flanking oligos (SEQ ID NOS 9 and 1; 100 pM each) were added in 50 µl buffer with Amplitaq (2.5 u). After heating to 94° C. for 3 min, the mix was subjected to 25 cycles of 1.5 min at 94° C., 2 min at 55° C. and 2 min at 72° C. followed by 10 min at 72° C. The product was a band at 1336 bp, isolated as described previously, then cut with EcoRI and HindIII and cloned into pBluescript in DH5α (clones were screened by PCR with oligos SEQ ID NOS 3 and 4) to give pMF35. To make the complete Fd-HCPB fusion sequence, plasmids pAF1 and pMF35 were cut (10 µg of each) with NcoI and EcoRI for 2 h in buffer (100 µl) containing 50 mM potassium acetate, 20 mM Tris-acetate (pH 7.9), 10 mM $MgCl_2$, 1 mm DTT, EcoRI (40 u) and NcoI (20 u). The vector fragment (3.4 kb) from pAF1 was isolated and treated with calf intestinal alkaline phosphatase as described in Reference Example 9 and ligated to the purified 1.2 kb fragment from pMF35. The resulting vector was cloned in DH5α (screened by PCR with oligos SEQ ID NOS 3 and 4 for a 1,922 bp insert) and named pMF39. The EcoRI-HindIII fragment from pMF39 was cloned into pEE6 [this is a derivative of pEE6.hCMV—Stephens and Cockett (1989) Nucleic Acids Research 17, 7110—in which a HindIII site upstream of the hCMV promoter has been converted to a BglII site] in DH5α (screened by PCR with oligos SEQ ID NOS 5 and 6 for a 2,200 bp, approximately, insert) to give pMF43.

Plasmid pAF3 (described above in e) and pEE12 [this vector is similar to pSV2.GS described in Bebbington et al. (1992) Bio/Technology 10, 169–175, with a number of restriction sites originally present in pSV2.GS removed by site-directed mutagenesis to provide unique sites in the multi-linker region]. The appropriate vector and insert fragments from each digest were then isolated from Seaplaque GTG agarose and ligated together and used to transform competent DH5α cells also as described earlier. The transformed cells were plated onto L agar plus 100 µg/ml ampicillin. Screening of colonies from the transformation was by a PCR method. Colonies were transfered into 200 µl distilled water and mixed by vortexing. The suspended cells were then heated to 100° C. for 1 minute and centrifuged at 11,600×g for 2 minutes prior to using the supernatant in a PCR reaction. In each PCR reaction, an oligo which primes within the CMV promoter (SEQ ID 5) was used with the oligo complementary to the 3' region of the light chain (SEQ ID 16) as appropriate. Only clones with the antibody fragment gene inserted in expressing orientation downstream from the CMV promoter will produce specific PCR products of approximately 2.0 kb. The resulting plasmid was named pAF6. To make the co-expression vector, pMF43 (10 µg) was cut with BglII (20 u) and SalI (40 U) in buffer (100 µl) containing 10 mM Tris-HCl (pH 7.9), 150 mM NaCl, 10 mM $MgCl_2$, 1 mM DTT and BSA (100 µg/ml) and the 4348 bp fragment isolated by agarose gel electrophoresis and purified with Geneclean as described previously. Similarly, pAF6 was cut with BamHI (40 u) and SalI (40 u) and the 7.8 kb vector fragment isolated and ligated to the BglII-SalI fragment from pMF43 and cloned into DH5α. Colonies were screened by PCR with 2 sets of oligos (SEQ ID NOS 14 and 12, and SEQ ID NOS 13 and 6). Clones giving PCR products of 360 bp and 1.3 kp respectively were characterised by DNA sequencing. A clone with correct sequence was named pMF53—light chain/Fd-HCPB co-expression vector in DH5α.

g) Expression of A5B7 F(ab')$_2$-HCPB in COS cells

The procedure described in Reference Example 9 for co-transfection of COS-7 cells with the plasmid encoding the prepro sequence (pMF67) was repeated with pMF48 replaced by pMF53. COS cell supernatants were examined for HCPB activity as described in Reference Examples 3 and 9. COS cell supernatants which had been treated with LIPOFECTIN reagent, but without plasmid DNA, hydrolysed 1.2% of the substrate, whereas the COS cell supernatants transfected with the mix of plasmids expressing light chain/Fd-HCPB and prepro sequence hydrolysed 34% of the Hipp-Arg substrate. COS cells transfected with only pMF53 plasmid hydrolysed Hipp-Arg at the level seen for COS cells which had been treated with LIPOFECTIN reagent alone. By Western analysis (see h below) bands of approximatey 80 kDa and 160 kDa were visible, corresponding to Fab'-HCPB and $F(ab')_2$-$(HCPB)_2$ respectively. In a CEA ELISA assay (see i and j below) cell supernatants (see above) were used to detect the presence of CEA binding material according to the protocol given in j.

h) Western Blot Analysis

Western blot analysis was performed as described as follows:

Aliquots (20 μl) of each supernatant sample were mixed with an equal volume of sample buffer (62.5 mM Tris, pH6.8, 1% SDS, 10% sucrose and 0.05% bromophenol blue) with and without reductant. The samples were incubated at 65° C. for 10 minutes before electrophoresis on a 8–18% acrylamide gradient gel (Excel gel system from Pharmacia Biotechnology Products) in a Multiphor II apparatus (LKB Produkter AB) according to the manufacturer's instructions. After electrophoresis, the separated proteins were transferred to a Hybond C-Super membrane (Amersham International) using a Novablot apparatus (LKB Produkter AB) according to protocols provided by the manufacturer. After blotting, the membrane was air dried.

The presence of antibody fragments was detected by the use of an anti-murine $F(ab')_2$ antibody-peroxidase conjugate (ICN Biomedicals, product no. 67-430-1). The presence of murine A5B7 antibody fragments was visualised using the ECL detection system (Amersham International) according to the protocol provided.

i) ELISA Analysis

Standard procedures for ELISA assay are available in "Laboratory Techniques in Biochemistry and Molecular Biology" eds. Burdon, R. H. and van Kippenberg, P. H., volume 15, "Practice and Theory of Enzyme Immunoassays", Tijssen, P., 1985, Elsevier Science Publishers B. V. Another source of information is "Antibodies—A Laboratory Manual" Harlow, E. and Lane, D. P. 1988, published by Cold Spring Harbor Laboratory.

j) ANTI-CEA ELISA

1. Prepare coating buffer (1 capsule of Carbonate-Bicarbonate buffer—Sigma C-3041—in 100 ml double distilled water).
2. Add 5 μl of CEA stock solution (1 mg/ml, Dako) to 10 ml of coating buffer for each 96 well plate required.
3. Add 100 μl of diluted CEA to each well of a Nunc "Maxisorp" microtitre plate—50 ng/well/100 μl.
4. Incubate plates at 4° C. overnight (or room temp. for 2 hours).
5. Wash plates 4 times for 5 minutes each with Phosphate buffered saline+0.01% Sodium azide (PBSA)+0.05% Tween 20.
6. Block plates (after banging dry) with 1% BSA (Sigma A-7888) in PBSA containing 0.05% Tween 20 at 200 μl per well. Incubate at room temp. for 2 hours.
7. Wash plates 4 times for 5 minutes each with PBSA containing 0.05% Tween 20.
8. Load samples (culture supernatants) and standards (doubling dilutions of proteolytic A5B7 $F(ab')_2$) as appropriate. Dilute samples in growth medium (or PBS). Include PBSA+1% BSA and diluent as blanks.
9. Incubate at ambient temperature for 3 h.
10. Wash plates 6 times for 5 minutes each with PBSA+0.5% Tween 20.
11. Prepare secondary antibody solution (anti-mouse IgG $F(ab')_2$, from goat, peroxidase conjugated—ICN 67-430-1—at 20 μl in 40 ml PBSA+1% BSA+0.5% Tween 20) and add 100 μl per well.
12. Incubate at room temp. for 1 h.
13. Wash plates 6 times for 5 minutes each with PBSA+0.5% Tween 20.
14. Prepare developing solution by dissolving 1 capsule of Phosphate-Citrate Perborate buffer (Sigma P-4922) in 100 ml double distilled water. Add 30 mg o-Phenylenediamine Dihydrochloride (OPD, Sigma P-8287) per 100 ml buffer. Add 150 μl per well.
15. Incubate at room temp. in darkness for 15 minutes.
16. Stop reaction by addition of 50 μl per well of 2M Sulphuric acid.
17. Read OD 490 nm in plate reader.

Example 1

Cloning and Expression of D253K HCPB-$(His)_6$-c-Myc from E.coli

The method of cloning and expressing the D253K-HCPB in E.coli was very similar to the method described in Reference Example 7. Again pICI266 was used as the cloning vector, and the starting material for PCR of the pro-HCPB gene was plasmid pICI1698 (as described in Reference Example 6). However, in this case site directed mutagenesis was used during the PCR amplification of the gene to change the codon at amino acid position 253 in the mature gene from Aspartate to Lysine (GAC to AAA), the D253K change. Two PCR mixtures were prepared, in a manner similar to that described in Reference Example 7. In the first reaction primers were FSPTS1 (SEQ ID NO: 40) and 1398 (SEQ ID NO: 57). In the second reaction primers were 6HIS9E10R1BS1 (SEQ ID NO: 41) and 1397 (SEQ ID NO: 58). In both reactions the starting DNA was pICI1698. Primers 1398 and 1397 (SEQ ID NOs: 57 and 58) are designed to anneal around amino acid codon 253, introduce the GAC to AAA change in the DNA sequence, and produce complementary sequence at the ends of the two PCR products. The other two primers, FSPTS1 and 6HIS9E10R1BS1 (SEQ ID NOs: 40 and 41) are described in Reference Example 7. Aliquots of the two PCR reactions were analysed for DNA of the correct size (about 750 and 250 base pairs) and estimation of concentration by Agarose gel electrophoresis, and found to contain predominantly bands of the correct size. Another PCR was then set up using approximately 4 ng of each of the first two PCR products, in the presence of dNTPs to a final concentration of 200 μM, Taq polymerase reaction buffer, 2 U of Taq polymerase in a final volume of 80 μl. The mixture was heated at 94° C. for 10 minutes prior to the addition of the Taq enzyme; and PCR incubation was carried out using 10 cycles of 94° C. for 1 minute and 63° C. for 4 minutes. On completion of these cycles the reaction mix was made up to 120 μl by the addition of 120 pmols of each end primer, FSPTS1 and 6HIS9E10R1BS1 (SEQ ID NOs: 40 and 41), additional dNTPs (approximately an extra OOpM), Taq polymerase reaction buffer, and 4 U of Taq polymerase. The mixture was heated at 94° C. for 10 minutes prior to addition of Taq enzyme, and the PCR incubation was carried out using 30 cycles of 94° C. for 1.5 minutes, 50° C. for 2 minutes, and 72° C. for 2 minutes, followed by a single incubation of 72° C. for 9.9 minutes at the end of the reaction.

An aliquot of the PCR product was analysed for DNA of the correct size (about 1000 base pairs) by agarose gel electrophoresis and found to contain predominantly a band of the correct size. The remainder of the product from the reaction mix was purified in a similar manner to Reference Example 7. The isolated DNA was restriction digested with enzymes FspI and EcoRI, and a band of the correct size (about 1000 base pairs) purified in a similar manner to Reference Example 7.

pICI266 double stranded DNA, prepared in a similar manner to Reference Example 7, was restriction digested with KpnI enzyme, and blunt-end treated with T4 DNA polymerase being very careful to ensure complete digestion. The purified DNA was then digested with restriction enzyme EcoRI. DNA of the correct size (about 5600 base pairs) was purified in a similar manner to Reference Example 7.

Aliquots of both restricted and purified DNA samples were checked for purity and concentration estimation using agarose gel electrophoresis compared with known standards. From these estimates ligation mixes were prepared to clone the HCPB gene into the pICI266 vector in a similar manner to Reference Example 7.

Following the ligation reaction the DNA mixture was used to transform *E.coli* strain DH5α, colonies were picked and tested by hybridisation, in a similar manner to Reference Example 7.

Six positive hybridisation isolates were checked by PCR for inserts of the correct size, using primers FSP1TS1 and 6HIS9E10R1BS1 (SEQ ID NOs: 40 and 41), and for priming with an internal primer FSPTS1 (SEQ ID NO: 40) and 679 (SEQ ID NO: 33) in a similar manner to Reference Example 7. The PCR products were analysed for DNA of the correct size (about 1000 base pairs from primers FSPTS1 to 6HIS9E10R1BS1, and about 430 base pairs from primers FSPTS1 to 679) by agarose gel electrophoresis. All clones gave PCR DNA products of the correct size.

All six of the clones were then taken for plasmid DNA preparation, and two were sequenced over the region of PCR product in a similar manner to Reference Example 7. The clones were sequenced using eight separate oligonucleotide primers known as 1281, 677, 1504, 679, 1802, 1590, 1280 and 1731 (SEQ ID NOs: 37, 34, 42, 33, 45, 43, 35 and 44). From the sequencing results a clone containing a plasmid with the required D253K-HCPB gene sequence was selected, and is known as pICI1713.

The confirmed sequence of the cloned D253K-HCPB gene in pICI1713, showing amino acid translation, from the start of the PelB sequence to the EcoRI restriction site is shown as SEQ ID NO: 59 with DNA numbering starting from 1 in the first codon of PelB, and peptide numbering starting from 1 in the mature HCPB.

To obtain controlled expression of the D253K-HCPB, the pICI1713 plasmid DNA was transformed into calcium chloride transformation competent *E.coli* expression strains in a similar manner to Reference Example 7. All pICI1713 transformed expression strains were treated in a similar manner to Reference Example 7 to test for expression of the cloned D253K-HCPB gene. In this case the 9E10 monoclonal antibody specific for the C-myc peptide tag was used in the Western analysis, as the D253K-HCPB has the C-terminal $(His)_6$-c-myc tag in a similar manner to Reference Example 7.

Expression of the cloned tagged D253K-HCPB in pICI266 (pICI1713) was demonstrated from *E.coli* by the Coomassie stained gels showing a strong protein band at about 35,000 Daltons when compared to vector (pICI266) alone clones, and clones producing the tagged HCPB (Reference Example 7). A band of the same size gave a strong signal by Western analysis detection of the c-myc tag.

Example 2

Cloning and Expression of D253R HCPB-$(His)_6$-c-Myc from *E.coli*

The method of cloning and expressing the D253R-HCPB in *E.coli* was very similar to the method described in Reference Example 8. Again pICI266 was used as the cloning vector, and the starting material for PCR of the pro-HCPB gene was plasmid pICI1712 (as described in Reference Example 7. However, in this case site directed mutagenesis was used during the PCR amplification of the gene to change the codon at amino acid position 253 in the mature gene from Aspartate to Arginine (GAC to CGC), the D253R change. Two PCR mixtures were prepared, in a manner similar to that described in Reference Examples 7 and 8. In the first reaction primers were 2264 (SEQ ID NO: 48) and 2058 (SEQ ID NO: 61). In the second reaction primers were 6HIS9E10R1BS1 (SEQ ID NO: 41) and 2054 (SEQ ID NO: 62). In both reactions the starting DNA was pICI1712.

Primers 2058 and 2054 (SEQ ID NOs: 61 and 62) are designed to anneal around amino acid codon 253, introduce the GAC to CGC change in the DNA sequence, and produce complementary sequence at the ends of the two PCR products. The other two primers, 2264 and 6HIS9E10R1BS1 (SEQ ID NOs: 48 and 41) are described in Reference Examples 7 and 8. Aliquots of the two PCR reactions were analysed for DNA of the correct size (about 750 and 250 base pairs) and estimation of concentration by Agarose gel electrophoresis, and found to contain predominantly bands of the correct size. Another PCR was then set up using approximately 4 ng of each of the first two PCR products, in the presence of dNTPs to a final concentration of 200 $\mu$M, Taq polymerase reaction buffer, 2 U of Taq polymerase in a final volume of 80 $\mu$l. The mixture was heated at 94° C. for 10 minutes prior to the addition of the Taq enzyme, and PCR incubation was carried out using 10 cycles of 94° C. for 1 minute and 63° C. for 4 minutes. On completion of these cycles the reaction mix was made up to 120$\mu$l by the addition of 120 pmols of each end primer, 2264 and 6HIS9E10R1BS1 (SEQ ID NOs: 48 and 41), additional dNTPs (approximately an extra 100 $\mu$m), Taq polymerase reaction buffer, and 4 U of Taq polymerase. The mixture was heated at 94° C. for 10 minutes prior to addition of Taq enzyme, and the PCR incubation was carried out using 30 cycles of 94° C. for 1.5 min, 50° C. for 2 min, and 72° C. for 2 min, followed by a single incubation of 72° C. for 9.9min at the end of the reaction.

An aliquot of the PCR product was analysed for DNA of the correct size (about 1000 base pairs) by agarose gel electrophoresis and found to contain predominantly a band of the correct size. The remainder of the product from the reaction mix was purified in a similar manner to Reference Example 7. The isolated DNA was restriction digested with enzymes NcoI and EcoRI, and a band of the correct size (about 1000 base pairs) purified in a similar manner to Reference Example 7.

pICI266 double stranded DNA, prepared in a similar manner to Reference Example 7, was restriction digested with NcoI and EcoRI enzymes, being very careful to ensure complete digestion. DNA of the correct size (about 5600 base pairs) was purified in a similar manner to Reference Example 7.

Aliquots of both restricted and purified DNA samples were checked for purity and concentration estimation using agarose gel electrophoresis compared with known standards. From these estimates ligation mixes were prepared to clone the HCPB gene into the pICI266 vector in a similar manner to Reference Example 7.

Following the ligation reaction the DNA mixture was used to transform E.coli strain DH5α, colonies were picked and tested by hybridisation, in a similar manner to Reference Example 7.

Three of the clones were then taken for plasmid DNA preparation, and were sequenced over the region of PCR product in a similar manner to Reference Example 7. The clones were sequenced using nine separate oligonucleotide primers known as 1281, 677, 1504, 679, 1802, 1590, 1280, 1731 and 1592 (SEQ ID NOs: 37, 34, 42, 33, 45, 43, 35, 44 and 54). From the sequencing results a clone containing a plasmid with the required D253R-HCPB gene sequence was selected, and is known as pICI1746.

The confirmed sequence of the cloned D253R-HCPB gene cloned in pICI1746, showing amino acid translation, from the start of the PelB sequence to the EcoRI restriction site is shown as SEQ ID NO: 63 with DNA numbering starting from 1 in the first codon of PelB, and peptide numbering starting from 1 in the mature HCPB.

To obtain controlled expression of the D253R-HCPB the pICI1746 plasmid DNA was transformed into transformation competent E.coli expression strains in a similar manner to Reference Example 7. All pICI1746 transformed expression strains were treated in a similar manner to Reference Example 7 to test for expression of the cloned D253R-HCPB gene. In this case the 9E10 monoclonal antibody specific for the C-myc peptide tag was used in the Western analysis, as the D253R-HCPB has the C-terminal $(His)_6$-c-myc tag in a similar manner to Reference Example 7.

Expression of the cloned tagged D253R-HCPB in pICI266 (pICI1746) was demonstrated from E.coli by the Coomassie stained gels showing a strong protein band at about 35,000 Daltons when compared to vector (pICI266) alone clones, and clones producing the tagged HCPB (Reference Example 7). A band of the same size gave a strong signal by Western analysis detection of the c-myc tag.

Purification is achieved using methodology analogous to that set out below in Example 3.

Example 3
Purification of Mutant D253K HCPB-$(His)_6$-c-Myc Proteins from E.coli First a 20 liter fermentation process for carboxypeptidase B analogue D253K in a cell paste is described. E.coli K12 strain MSD 1924 was transformed with plasmid pZen 1713 (pICI 1713; see Example 1 above) and the resultant strain MSD 2230 (MSD 1924 pZen 1713) was stored in glycerol freezing mix at −80° C.

MSD 2230 was streaked onto agar plates containing L-tetracycline (10 $\mu gml^{-1}$) medium to separate single colonies after overnight growth at 37° C. Six single colonies of MSD 2230 were removed from the surface of the L-tetracycline (10 $\mu gml^{-1}$) agar, re suspended in a 10 ml L-tetracycline (10 $\mu gml^{-1}$) broth and 100 $\mu l$ of this culture was immediately inoculated into each of six 250 ml Erlenmeyer flasks containing 75 ml of L-tetracycline (10 $\mu gml^{-1}$) broth. After growth for 15–16 hours at 37° C. on a reciprocating shaker (300 rpm) the contents of the flasks were pooled and used to inoculate a single fermenter (U30D vessel, B. Braun, Melsungen, Germany) containing 15 liters of the growth medium described in FIG. 6.

The fermentation was performed at a temperature of 37° C. and pH of 6.7 and pH of 6.7 which was automatically controlled to the set point by the addition of 6M sodium hydroxide or 2M sulphuric acid. The dissolved oxygen tension (dOT) set point was 50% air saturation and it was maintained by the automatic adjustment of the fermenter stirrer speed between 200 and 1000 rpm. The air flow to the fermenter was maintained at 20 standard liters per minute which corresponds to 1.3 vessel volumes per minute (vvm) by a Tylan mass flow controller.

4.5 hours following inoculation, a solution of yeast extract (225 $gl^{-1}$) was fed into the fermenter at a rate of 190–210 $mlh^{-1}$ for 28.5 hours. 1.5 hours after the yeast extract feed was started, the fermentation temperature set point was reduced to 25° C. When this temperature was attained, approximately 1 hour later, expression of the carboxypeptidase analogue D253K was induced with a single shot addition of 50% arabinose to give a final concentration in the fermenter vessel of 0.5%. 1–2 hours following induction, a mixture of glycerol (714 $gl^{-1}$) and ammonium sulphate (143 $gl^{-1}$) was fed into the fermenter at 45–55 $mlh^{-1}$ until harvest. The fermentation was continued under these conditions until ca. 75 hours post fermenter inoculation when the culture was harvested by transferring aliquots of the fermenter contents into 1 liter centrifuge bottles. The spent medium was separated from the bacterial cells by centrifugation in a Sorvall RC-3B centrifuge (7,000×g, 4° C., 30min.). This process typically yields a final dry weight of ca.20 $gl^{-1}$.

The cell paste was purified as follows. Recombinant E.coli cell paste containing the recombinant enzyme, D253K HCPB, was taken from storage at −70° C. and allowed to thaw. The weight of cell paste was measured and found to be 309 grams. The paste was resuspended with the addition of buffer A [200 mM Tris (hydroxymethyl)aminomethane hydrochloride (TRIS-HCl), 20% sucrose, pH 8.0] to give a resuspended volume of 320 ml. The cell suspension was incubated at room temperature for 20 minutes with occasional gentle mixing before an equal volume of distilled water, at room temperature, was added and thoroughly mixed in. The cell suspension was again incubated at room temperature for 20 minutes with occasional gentle mixing.

The resulting crude osmotic shockate was clarified by centrifugation at 98000 ×g for 90 minutes at 4° C. after which the supernatant was decanted off from the pelleted insoluble fraction, giving a clarified volume of 240 ml. Deoxyribonuclease 1 (24 mg) was dissolved in distilled water (5 ml) and added to the supernatant. The mixture was incubated at room temperature, with continuous shaking for 30 minutes to reduce the vicosity of the supernatant enough for it to be loaded on to a Carboxypeptidase Inhibitor CNBr activated Sepharose affinity column, prepared according to instructions with the CNBr activated Sepharose 4B from Pharmacia and carboxypeptidase inhibitor from potato tuber (c-0279,Sigma). The supernatant was diluted 1:1 with 10 mM TRIS-HCl, 500 mM sodium chloride, pH 8.0 (Buffer B), adjusted to pH8.0 and loaded, over night, on to the Carboxypeptidase inhibitor affinity column at 0.5 ml/min. The column was pre-equilibrated with buffer B at 4° C. After loading the supernatant, the column was washed until the absorbance of the flow through was back to baseline before the bound material was eluted from the column by elution buffer (100 mM sodium carbonate, 500 mM sodium chloride, pH 11.4) at 40° C., with 1 ml fractions being collected. The eluted fractions were frozen at −20° C. after samples were taken to determine those containing the recombinant carboxypeptidase. This was accomplished by Western blot analysis using an anti-c-myc tag antibody (9E10), followed by an anti-mouse -horseradish peroxidase conjugate (a-9044, sigma) that gave a colour reaction with exposure to 4-chloro-naphthol and hydrogen peroxide. Fractions 11 to 44 were determined to contain the recombinant carboxypeptidase B. These were pooled, the pH adjusted to pH7.5 and concentrated using a Millipore Centifugal Ultrafree –20 (10,000 molecular weight cut off) before being snap-frozen and stored at –20° C. The purification detailed here provided 4.7 mg of D253K mutant carboxypeptidase at a purity of 80%, in a volume of 0.95 ml.

Example 4
Synthesis of an Aspartic Acid Phenol Mustard Prodrug (Compound 5a, FIG. 7)

(2S),2-(3-{4-[bis-(2-chloroethyl)-amino)-phenoxycarbonyl}-propionyl-amino)-succinic acid Analogous methodology to that set out in Reference Example 4 was used.

(2S),2-(3-{4-[bis-(2-chloroethyl)-amino)-phenoxycarbonyl}-propionylamino)-succinic acid dibenzyl ester (4a) was hydrogenated for 2 h at 80 psi to give the desired end product 5a (yield: 86%).

5a: $^1$HNMR (CD3OD): 2.65–2.75 (t, 2H); 2.8–2.9 (m, 4H); 3.7–3.75 (m, 4H); 3.8–3.85 (m, 4H); 4.75 (t, 1H); 6.7–6.8 (m, 2H); 7.0–7.1 (m, 2H).

MS (ESI): 471–473 (MNa)$^+$

Anal. ($C_{18}H_{22}N_2O_7Cl_2$ 1.4 $H_2O$)

Calc. %C, 45.56; H, 5.27; N, 5.90.

Found %C, 45.79; H, 5.60; N, 5.91.

Starting material compound 4a was prepared as follows.

(2S),2-amino-succinic acid dibenzyl ester (Compound 2a) was reacted to give (2S),2-(3-carboxypropionylamino)-succinic acid dibenzyl ester (compound 3a) after recrystallisation with diethyl ether/hexane: (Yield: 80%).

3a: 1HNMR (CDCl$_3$): 2.42–2.6 (m, 2H); 2.6–2.75 (m, 2H); 2.85 (dd, 2H); 3.1 (dd, 1H); 4.9 (dd, 1H); 5.05 (dd, 2H); 5.15 (s, 2H); 6.7 (d, 1H); 7.25–7.5 (m, 10 H).

MS (ESI): 436 [MNa]$^+$

Anal. ($C_{22}H_{23}NO_7$ 0.4$H_2O$):

Calculated %C, 62.82; H, 5.70; N, 3.33.

Found %C, 63.2; H, 5.75; N, 2.9.

3a was reacted to give the desired starting material 4a (yield: 78%) (stirring was maintained for 3 h at room temperature and purification was achieved by flash chromatography using diethyl ether/hexane (70/30 V/V as eluent).

4a: 1HNMR (CDCl$_3$): 2.55–2.65 (m, 2H); 2.8–2.9 (m, 2H); 2.9 (dd, 1H); 3.1 (dd, 1H); 3.6 (dd, 4H); 3.7 (dd, 4H); 4.9 (dd, 1H); 5.05 (dd, 2H); 5.15 (s, 2H); 6.58 (d, 1H); 6.65 (d, 2H); 6.95 (d, 2H); 7.25–7.4 (m, 10 H).

MS (ESI): 651–653 (MNa)$^+$

Example 5
Synthesis of a Glutamic Acid Phenol Mustard Prodrug (5b; FIG. 7)

(2S), 2-(3-{4-[bis-(2-chloroethyl)-amino)-phenoxycarbonyl}-propionyl-amino)-pentanedioic acid Analogous methodology to that set out in Reference Example 4 was used.

(2S),2-(3-{4-[bis-(2-chloroethyl)-amino)-phenoxycarbonyl}-propionylamino)-pentanedioic acid dibenzyl ester (4b) was hydrogenated for 3 h at 60 psi to give the desired end product 5b (yield: 93%).

5b: 1HNMR (CD$_3$OD): 1.9–2.0 (m, 1H); 2.1–2.2 (m, 1H); 2.35–2.45 (m, 2H); 2.55–2.7 (m, 2H); 2.8–2.9 (m, 2H); 3.65–3.7 (m, 4H); 3.72–3.8 (m, 4H); 4.4–4.5 (m, 1H); 6.75 (d, 2H); 6.95 (d, 2H).

MS (ESI): 485–487 (MNa)$^+$

Starting material compound 4b was prepared as follows.

(2S),2-amino-pentanedioic acid dibenzyl ester (2b) was reacted to give (2S),2-(3-carboxypropionylamino)-pentanedioic acid dibenzyl ester (3b) (Yield: quantitative)

3b: 1HNMR (CDCl$_3$): 2.0–2.1 (m, 1H); 2.2–2.3 (m, 1H); 2.3–2.5 (m, 4H); 2.6–2.7 (m, 2H); 4.65 (dd, 1H); 5.05 (s, 2H); 5.15 (s, 2H); 6.5 (d, 1H); 7.3–7.4 (m, 10 H).

MS (ESI): 450 [MNa]+

3b was reacted to give the desired starting material 4b (yield: 82%).

4b: 1HNMR (CDCl$_3$): 1.95–2.05 (m, 1H); 2.2–2.3 (m, 1H); 2.3–2.5 (m, 2H); 2.6 (dt, 2H); 2.8–3.0 (m, 2H); 3.6 (dd, 4H); 3.7 (dd, 4H); 4.7 (dd, 1H); 5.1 (s, 2H); 5.2 (s, 2H); 6.3 (d, 1H); 6.6 (d, 2H); 6.95 (d, 2H); 7.3–7.4 (m, 10 H).

MS (ESI): 665–667 (MNa)$^+$

Example 6
Assay of Activity of Mutant Human CPB and Native Human CPB Against Hipp-Asp and Hipp-Glu Prodrug Analogues Purified mutants of human CPB (D253K and D253R; Examples 1–3) and native human CPB, produced as described in Reference Example 12, were assayed for their ability to convert either hippuryl-L-aspartic acid (Hipp-Asp—Reference Example 2), hippuryl-L-glutamic acid (Hipp-Glu—Reference Example 1) or hippuryl-L-arginine (Sigma Chemical Company—cat no. H6625) to hippuric acid using a HPLC based assay.

The reaction mixture (250 μl) contained 4 μg human CPB (native or mutant) and 0.5 mM Hipp-Asp or Hipp-Glu in 0.025 M Tris-HCL, pH 7.5. Samples were incubated for 5 hr at 37° C. The reactions were terminated by the addition of 250 μl of 80% methanol, 20% distilled water, 0.2% trifluoro acetic acid and the amount of hippuric acid generated was quantified by HPLC.

HPLC analysis was carried out using a Hewlett Packard 1090 Series 11 (with diode array) HPLC system. Samples (50 μl) were injected onto a Hichrom Hi-RPB column (25 cm) and separated using a mobile phase of 40% methanol, 60% distilled water, 0.1% trifluoro acetic acid at a flow rate of 1 ml/min. The amount of product (hippuric acid) produced was determined from calibration curves generated with known amounts of hippuric acid (Sigma-H6375). The results are shown in Table 1 and are expressed as the percentage conversion of substrate into product in 5 hr at 37° C. with 4 μg enzyme.

TABLE 1

| Conversion of Hipp-Asp and Hipp-Glu by mutant and native human CPB | | | |
|---|---|---|---|
| | Hipp-Asp | Hipp-Glu | Hipp-Arg |
| | (% conversion to Hippuric acid) | | |
| Native CPB | 0 | 0 | 100 |
| D253K mutant CPB | 78 | 91 | <2 |
| D253R mutant CPB | 72 | 52 | 3 |

The data show that introduction of either a lysine or arginine residue at position 253 in human CPB instead of the aspartate residue present in the native enzyme changes the substrate specificity of the enzyme so that it is capable of conversion of either Hipp-Asp or Hipp-Glu. In contrast, the native enzyme is unable to convert either of these compounds into Hippuric acid but does convert Hipp-Arg to hippuric acid. The best activity was seen with the D253K mutant and the Hipp-Glu substrate.

Example 7
Determination of Km and kcat of HCPB Mutants with Hipp-Asp and Hipp-Glu Purified D253K HCPB, [Q54R,D145A,D253K]HCPB, [G251N,D253K]HCPB and [G251T,D253K]HCPB were produced as described in Example 3, Reference Example 12, Example 27 and Example 28 respectively were assayed against Hipp-Asp (Reference Example 2),and/or Hipp-Glu (Reference Example 1) to determine Km and kcat for these substrates. Hipp-Glu and Hipp-Asp were diluted in range 0.25–8.0 mM and 0.25–5.0 mM respectively in 0.025 M Tris-HCL buffer, pH 7.5. Where necessary substrate samples were adjusted to pH 7.5 with 1M NaOH.

D253K HCPB (4 µg/ml for Hipp-Asp and 0.5 µg/ml for Hipp-Glu), [Q54R,D145A,D253K]HCPB (1.5 µg/ml for Hipp-Glu), [G251N,D253K]HCPB (0.14 µg/ml for Hipp-Glu) and [G251T,D253K]HCPB (0.02 µg/ml for Hipp-Glu) were added to these substrates (500 µl reaction volume) to start the reaction. Samples were incubated for 5 h at 37° C. Reactions were terminated by the addition of 500 µl methanol/distilled water (80/20) containing 0.2% TFA. The amount of hippuric acid produced was quantified by HPLC as described in Example 6.

Km and Vmax values were calculated using the ENZFITTER software programme (Biosoft, Perkin Elmer). Kcat was calculated from Vmax by dividing by the enzyme concentration in the reaction mixture (using a molecular weight for HCPB of 34 KDa). The results are shown in Tables 2a and 2b.

TABLE 2a km and kcat data for Hipp-Asp and Hipp-Glu with D253K mutant HCPB

| | Km (mM) | kcat ($s^{-1}$) | kcat/Km ($mM^{-1}s^{-1}$) |
|---|---|---|---|
| Hipp-Asp | 2.7 | 0.26 | 0.1 |
| Hipp-Glu | 5.3 | 3.8 | 0.7 |

TABLE 2b

Km and kcat data for Hipp-Glu with HCPB mutants

| Mutant | Km (mM) | kcat ($s^{-1}$) | kcat/Km ($mM^{-1}s^{-1}$) |
|---|---|---|---|
| [Q54R,D145A,D253K] | 10.6 | 15 | 1.4 |
| [G251N,D253K] | 2.3 | 24 | 10 |
| [G251T,D253K] | 1.1 | 75 | 68 |

The data confirm that replacing aspartate with a lysine residue at position 253 in human CPB results in an enzyme which can convert both Hipp-Asp and Hipp-Glu into hippuric acid with reasonable enzyme kinetics. The kcat/Km is approximately 7 fold greater with the Hipp-Glu compared to the Hipp-Asp substrate with D253K HCPB. Introduction of additional mutations increases the activity of D253K HCPB versus Hipp-Glu by up to 100 fold.

Example 8
Assay of Activity of Mutant HCPB and Native HCPB Against Glutamic Acid Prodrug Purified D253K HCPB and native human CPB, produced as described in Example 3 and Reference Example 12 respectively, were assayed for their ability to enzymatically cleave glutamic acid from a glutamic acid prodrug (Example 5). Cleavage liberates an intermediate (Reference Example 5) which self collapses non-enzymatically to release the active phenol mustard drug. Conversion of the glutamic acid prodrug to intermediate was measured using a HPLC based assay.

Prodrug was diluted in the range 0.25–5.0 mM in 0.025 M Tris-HCL buffer, pH 7.5. Where necessary prodrug samples were adjusted to pH 7.5 with 1M NaOH. D253K mutant HCPB or native HCPB, both at a final concentration of 0.25 mg/ml, were added to the these substrates (250 µl reaction volume prewarmed to 37° C. for 2 min) to start the reaction. Samples were incubated for 4 minutes at 37° C. The reaction was terminated by the addition of 250 µl 98.8% MeCN, 0.2% TFA and the samples placed on ice. The amount of intermediate produced was then quantified by HPLC.

HPLC separation was carried out as described in Example 6 except that a mobile phase of MeCN/distilled water (55/45 V/V) containing 0.1% TFA was used to achieve separation of the prodrug (retention time 4.9 minutes) and intermediate (retention time 8.4 minutes). The amount of intermediate produced was quantified from calibration curves generated with known amounts of the intermediate.

The amount of intermediate formed at 5.0 mM and 0.25 mM prodrug with native and mutant (D253K) HCPB in replicate samples is shown in Table 3.

TABLE 3

Conversion of prodrug to intermediate by native and mutant (D253K) HCPB.

| Prodrug concentration | Intermediate concentration (mM) | |
|---|---|---|
| (mM) | Native HCPB | Mutant HCPB |
| 5.0 | 0, 0 | 0.023, 0.022 |
| 0.25 | 0, 0 | 0.005, 0.005 |

Km, Vmax and kcat values for the mutant human enzyme (D253K) and the prodrug were calculated from the amount of intermediate produced over a range of substrate concentrations (0.25–5.0 mM) using the ENZFITTER software described in Example 7. The results for the D253K mutant HCPB were:

Km=1.25 mM

Vmax=1.17×$10^{-4}$ mMsec$^{-1}$ kcat=0.016 sec$^{-1}$

The data show that introduction of a lysine residue at position 253 in human CPB instead of the aspartate residue present in the native enzyme changes the substrate specificity of the enzyme so that it is capable of conversion of the glutamic acid prodrug into its self-collapsing intermediate. In contrast, the native enzyme is unable to convert the prodrug to its intermediate. Since the prodrug is relatively non-cytotoxic (Example 9) and the intermediate is non-enzymatically broken down to release free phenol mustard drug which kills tumour cells (Example 9) these results demonstrate that mutation of active site residues of CPB can yield a mutant human enzyme capable of converting a relatively non-cytotoxic prodrug into a potent cytotoxic drug capable of killing tumour cells.

Example 9
Cytotoxicity of Glutamic Acid Prodrug and Phenol Mustard Drug in LoVo Human Colorectal Tumour Cells The differential cytotoxicity to tumour cells of the glutamic acid prodrug (Example 5) and corresponding phenol mustard drug (FIG. 7, Compound 6) has been demonstrated by the following means.

LoVo colorectal tumour cells were incubated with prodrug or drug over a final concentration range of $5 \times 10^{-4}$ to $5 \times 10^{-8}$M in 96-well (2,500 cells/well) microtitre plates for 1 h at 37° C. The cells were then washed and incubated for a further three days at 37° C. After washing to remove dead cells, TCA was then added and the amount of cellular protein adhering to the plates was assessed by addition of SRB dye as described by P. Skehan et al, J. Natl. Cancer Inst. 82, 1107 (1990). Potency of the compounds was assessed by the concentration required to inhibit cell growth by 50% ($IC_{50}$).

Figure 5:
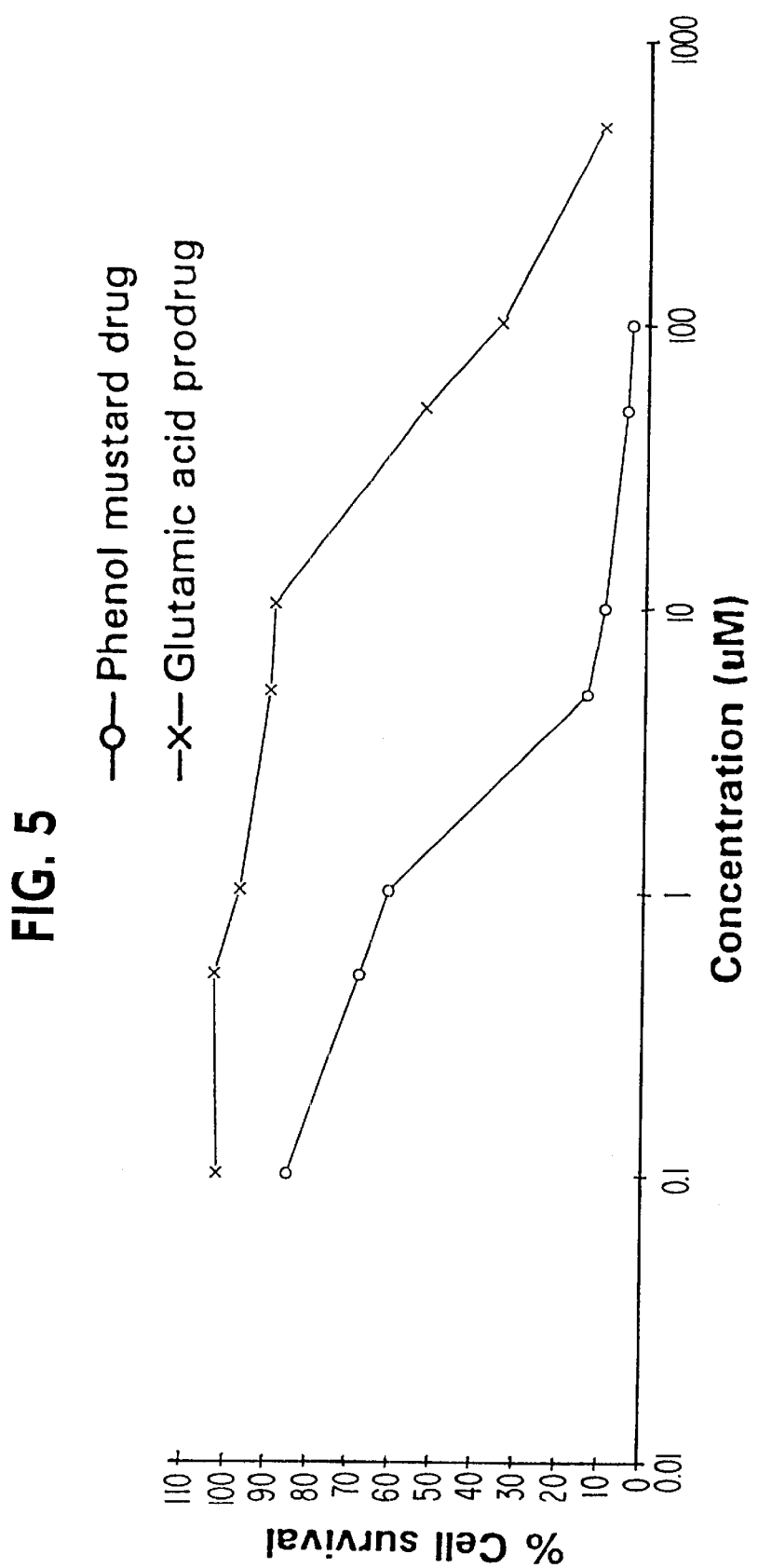
FIG. 5 illustrates cytotoxicity of a prodrug and corresponding drug.

Upon treatment of LoVo cells with the phenol mustard drug an $IC_{50}$ of approximately 1 μM was seen. In contrast the glutamic acid prodrug was much less cytotoxic with an $IC_{50}$ of approximately 5 μM (FIG. 5). Thus the mutant CPB glutamic acid prodrug is approximately 50 fold less cytotoxic to tumour cells than the phenol mustard drug.

If 100 μg of mutant HCPB (D253K) produced as described in Example 3 is added to the assay wells containing the glutamic acid prodrug cytotoxicity can be seen which is comparable to that of the active drug thus demonstrating conversion of the prodrug by the mutant enzyme to release the more potent drug. Addition of 100 μg of native human CPB to each well does not significantly enhance the cytotoxicity of the glutamic acid prodrug. These studies demonstrate the potential of the mutant human CPB enzyme (D253K) to selectively convert a relatively inactive prodrug into a potent cytotoxic drug capable of killing tumour cells.

Example 10
Preparation of Humanised A5B7 F(ab')$_2$-D253K HCPB Fusion Protein

The procedure described in Reference Example 13 is repeated but with murine A5B7 light chain and Fd sequences replace by sequences for humanised A5B7, and with the HCPB sequence replaced by D253K sequence. The 8 amino acid linker sequence described in Reference Example 13f) is replaced by the equivalent human sequence, APPVAGPS (SEQ ID NO: 66). The fusion protein is expressed from COS cells by co-transfection with the HCPB prepro sequence as described in Reference Example 13. Large-scale expression of the fusion protein is performed by transiently introducing the plasmid vectors (750 μg of each) into COS-7 cells (11) essentially as described in Reference Example 13. The product is purified either by passing the supernatant containing the fusion protein over immobilised protein A and elution of the bound fusion protein with high pH buffer or by passing the supernatant containing the fusion protein over immobilised carboxypeptidase inhibitor, following the route used for the purification of the recombinant carboxypeptidase enzyme, and elution with the same high pH as used with the enzyme in Example 3. Both these routes may involve further purification of the fusion protein by either gel permeation chromatography, ion exchange chromatography, hydrophobic interaction chromatography singly, or a combination of them.

The procedure described in Reference Example 13 is repeated but the murine sequences for Fd and light chain, as shown in SEQ ID NOS 20 and 22 respectively, are replaced by the humanised sequences shown in SEQ ID NOs 24 and 26 respectively. The HCPB sequence in Reference Example 13 is replaced by the D253K sequence [described in Example 1, but without the (His)$_6$-c-Myc tags]. The template for PCR in Reference Example 13 (pICI1698) is replaced by pICI1713 (described in Example 1).

The humanised sequences shown in SEQ ID NOs 24 and 26 are prepared by a variety of methods including those described by Edwards (1987) Am. Biotech. Lab. 5, 38–44, Jayaraman et al. (1991) Proc. Natl. Acad. Sci. USA 88, 4084–4088, Foguet and Lubbert (1992) Biotechniques 13, 674–675 and Pierce (1994) Biotechniques 16, 708.

Example 11
Shake Flask Fermentation for Preparation of D253K HCPB

*E.coli* strain MSD 213 was transformed with plasmid pICI 1713 (see Example 1) and the resultant strain MSD 213 pZen 1713 stored as a glycerol stock at −80° C. An aliquot of MSD 213 pZen 1713 was streaked onto agar plates of L-tetracycline to separate single colonies after overnight growth at 37° C. A single colony of MSD 213 pZen 1713 was removed and inoculated into a 250 ml Erlenmeyer flask containing 75 ml of L-tetracycline broth. After growth for 16 h at 37° C. on a reciprocating shaker the contents of the flask were used to inoculate to OD550=0.1 each of nine 2 L Erlenmeyer flasks containing 600 ml of L-tetracycline broth. The flasks were then incubated at 20° C. on a reciprocal shaker until growth, estimated by measuring the optical density of the culture, reached OD550=0.5. At this point heterologous protein production was induced by adding L-arabinose to the cultures to a final concentration of 0.01% w/v and the incubation continued at 20° C. as described above for a further 42 h. The spent medium was separated from the bacterial cells by centrifugation in a Sorvall RC-3B centrifuge (7000×g, 40° C., 30 min) and the cell paste stored at −70° C.

Example 12
Cloning and Expression of [G251N,D253R]HCPB-(His)$_6$-c-Myc from *E.coli*

The method of cloning and expressing the [G251N, D253R]HCPB in *E.coli* was very similar to the method described in Reference Example 8. The gene for [G251N, D253R]HCPB was prepared as described in Example 2 but the starting material for PCR site directed mutagenesis was the D253R HCPB gene in plasmid pICI1764 (described in Example 2) in place of pICI1712. However, in this case site directed mutagenesis was used during the PCR amplification of the gene to change the codon at amino acid position 251 in the mature gene from Glycine to Asparagine (GGC to AAC), the G251N change.

Two PCR mixtures were prepared, in a manner similar to that described in Reference Examples 7 and 8. In the first reaction primers were 2264 (SEQ ID NO: 48) and 1038 (SEQ ID NO: 68, replacing SEQ ID NO: 61). In the second reaction primers were 6HIS9E10R1BS1 (SEQ ID NO: 41) and 1043 (SEQ ID NO: 69, replacing SEQ ID NO: 62). In both reactions the starting DNA was pICI1764.

Primers 1038 and 1043 (SEQ ID NOs: 68 and 69) are designed to anneal around amino acid codon 251, introduce the GGC to MAC change in the DNA sequence, and produce complementary sequence at the ends of the two PCR products.

The confirmed sequence of the cloned [G251N,D253R] HCPB gene cloned in pMC12.5.4, showing amino acid translation, from the start of the PelB sequence to the EcoRI restriction site is similar to that shown as SEQ ID NO: 63 with DNA numbering starting from 1 in the first codon of PelB, and peptide numbering starting from 1 in the mature HCPB with the exception that amino acid number 251 is changed to an Asparagine (Asn) and the associated codon changed to AAC.

To obtain controlled expression of the [G251N,D253R] HCPB the pMC12.5.4 plasmid DNA was transformed into transformation competent *E.coli* expression strain MSD213 in a similar manner to Reference Example 7. The pMC12.5.4 transformed expression strain has been treated in a similar manner to Reference Example 7 to test for expression of the cloned [G251N,D253R]HCPB gene. In this case the 9E10 monoclonal antibody specific for the C-myc peptide tag was used in the Western analysis, as the [G251N, D253R]HCPB has the C-terminal (His)$_6$-c-myc tag in a similar manner to Reference Example 7.

Expression of the cloned tagged [G251N,D253R]HCPB in pICI266 (pMC12.5.4) was demonstrated from *E.coli* by the Coomassie stained gels showing a strong protein band at about 35,000 Daltons when compared to vector (pICI266) alone clones, and clones producing the tagged HCPB (Reference Example 7). A band of the same size has given a strong signal by Western analysis detection of the c-myc tag.

Example 13

Cloning and Expression of [G251N,D253K]HCPB-(His)$_6$-c-Myc from *E.coli*

The method of cloning and expressing the [G251N, D253K]HCPB in *E.coli* was very similar to the method described in Reference Example 8. The gene for [G251N, D253K]HCPB was prepared as described in Example 2 but the starting material for PCR site directed mutagenesis was the D253K HCPB gene in plasmid pICI1713 (described in Example 1) in place of pICI1712. However, in this case site directed mutagenesis was used during the PCR amplification of the gene to change the codon at amino acid position 251 in the mature gene from Glycine to Asparagine (GGC to AAC), the G251N change. Two PCR mixtures were prepared, in a manner similar to that described in Reference Examples 7 and 8. In the first reaction primers were 2264 (SEQ ID NO: 48) and 2261 (SEQ ID NO: 70, replacing SEQ ID NO: 61). In the second reaction primers were 6HIS9E10R1BS1 (SEQ ID NO: 41) and 2260 (SEQ ID NO: 71, replacing SEQ ID NO: 62). In both reactions the starting DNA was pICI1713. Primers 2261 and 2260 (SEQ ID NOs: 70 and 71) are designed to anneal around amino acid codon 251, introduce the GGC to AAC change in the DNA sequence, and produce complementary sequence at the ends of the two PCR products.

The confirmed sequence of the cloned [G251N,D253K] HCPB gene cloned in pMC43.1, showing amino acid translation, from the start of the PelB sequence to the EcoRI restriction site is similar to that shown as SEQ ID NO: 59 with DNA numbering starting from 1 in the first codon of PelB, and peptide numbering starting from 1 in the mature HCPB with the exception that amino acid number 251 is changed to an Asparagine (Asn) and the associated codon changed to AAC.

To obtain controlled expression of the [G251N,D253K] HCPB the pMC43.1 plasmid DNA was transformed into transformation competent *E.coli* expression strain MSD213 in a similar manner to Reference Example 7. The pMC43.1 transformed expression strain has been treated in a similar manner to Reference Example 7 to test for expression of the cloned [G251N,D253K]HCPB gene. In this case the 9E10 monoclonal antibody specific for the C-myc peptide tag was used in the Western analysis, as the [G251N,D253K]HCPB has the C-terminal (His)$_6$-c-myc tag in a similar manner to Reference Example 7.

Expression of the cloned tagged [G251N,D253K]HCPB in pICI266 (pMC43.1) Was demonstrated from *E.coli* by the Coomassie stained gels showing a strong protein band at about 35,000 Daltons when compared to vector (pICI266) alone clones, and clones producing the tagged HCPB (Reference Example 7). A band of the same size has given a strong signal by Western analysis detection of the c-myc tag.

Example 14

Cloning and Expression of [G251T,D253K]HCPB-(His)$_6$-c-Nyc from *E.coli*

The method of cloning and expressing the [G251T, D253K]HCPB in *E.coli* was very similar to the method described in Reference Example 8. The gene for [G251T, D253K]HCPB was prepared as described in Example 2 but the starting material for PCR site directed mutagenesis was the D253K HCPB gene in plasmid pICI1713 (described in Example 1) in place of pICI1712. However, in this case site directed mutagenesis was used during the PCR amplification of the gene to change the codon at amino acid position 251 in the mature gene from Glycine to Threonine (GGC to ACT), the G251T change. Two PCR mixtures were prepared, in a manner similar to that described in Reference Examples 7 and 8. In the first reaction primers were 2264 (SEQ ID NO: 48) and 1038 (SEQ ID NO: 68, replacing SEQ ID NO: 61). In the second reaction primers were 6HIS9E10R1BS1 (SEQ ID NO: 41) and 2659 (SEQ ID NO: 72, replacing SEQ ID NO: 62). In both reactions the starting DNA was pICI1713. Primers 1038 and 2659 (SEQ ID NOs: 68 and 72) are designed to anneal around amino acid codon 251, introduce the GGC to ACT change in the DNA sequence, and produce complementary sequence at the ends of the two PCR products.

The confirmed sequence of the cloned [G251T,D253K] HCPB gene cloned in pMC46.4.1, showing amino acid translation, from the start of the PelB sequence to the EcoRI restriction site is similar to that shown as SEQ ID NO: 59 with DNA numbering starting from 1 in the first codon of PelB, and peptide numbering starting from 1 in the mature HCPB with the exception that amino acid number 251 is changed to an Threonine (Thr) and the associated codon changed to ACT.

To obtain controlled expression of the [G251T,D253K] HCPB the pMC46.4.1 plasmid DNA was transformed into transformation competent *E.coli* expression strain MSD213 in a similar manner to Reference Example 7. The pMC46.4.1 transformed expression strain has been treated in a similar manner to Reference Example 7 to test for expression of the cloned [G251T,D253K]HCPB gene. In this case the 9E10 monoclonal antibody specific for the C-myc peptide tag was used in the western analysis, as the [G251T, D253K]HCPB has the C-terminal (His)$_6$-c-myc tag in a similar manner to Reference Example 7.

Expression of the cloned tagged [G251T,D253K]HCPB in pICI266 (pMC46.4.1) was demonstrated from *E.coli* by the Coomassie stained gels showing a strong protein band at about 35,000 Daltons when compared to vector (pICI266) alone clones, and clones producing the tagged HCPB (Reference Example 7). A band of the same size has given a strong signal by Western analysis detection of the c-myc tag.

Example 15

Cloning and Expression of [G251N,D253K,T266G]HCPB-(His)$_6$-c-Nyc from *E. coli*

The method of cloning and expressing the [G251N, D253K,T266G]HCPB in *E.coli* was very similar to the method described in Reference Example 8. The gene for [G251N,D253K,T266G]HCPB was prepared as described in Example 2 but the starting material for PCR site directed mutagenesis was the [G251N,D253K]HCPB gene in plasmid pMC43.1 (described in Example 13) in place of pICI1712. However, in this case site directed mutagenesis was used during the PCR amplification of the gene to change the codon at amino acid position 266 in the mature gene from Threonine to Glycine(ACC to GGC), the T266G change. Two PCR mixtures were prepared, in a manner similar to that described in Reference Examples 7 and 8. In the first reaction primers were 2264 (SEQ ID NO: 48) and 1045 (SEQ ID NO: 73, replacing SEQ ID NO: 61). In the second reaction primers were 6HIS9E10R1BS1 (SEQ ID NO: 42) and 55 (SEQ ID NO: 74, replacing SEQ ID NO: 62). In both reactions the starting DNA was pMC43.1.

Methods of PCR, cloning, expression and identification were the same as for Example 14. From the sequencing results a clone containing a plasmid with the required [G251N,D253K,T266G]HCPB gene sequence was selected, and is known as pMC47.1.

Example 16
Expression of Other Mutant HCPBs with Peptide Tag Using *E.coli*

A number of other mutant HCPBs have been constructed in a similar manner to the methods described in Reference Examples 7 and 8, and Examples 12, 13, 14 and 15. In each case oligos were constructed to introduce specific changes in the gene sequence by methods similar to those described above. In some cases additional mutations were identified upon complete sequencing of the mutated gene, and these were presumably introduced during the PCR reactions. Mutants with enzyme activity against substrate analogues (see Example 18 below) have been identified, and examples of these are given in Table 4 below. Enzyme activity is shown relative to that found from pICI1713 (D253K HCPB) or pICI1746 (D253R HCPB) in *E.coli* MSD213 by release of the periplasmic protein fraction by osmotic shock. This material is subsequently referred to as periplasmic shockate or shockate and is prepared by the following procedure.

1. A single colony was used to inoculate 75 ml of L-broth nutrient media containing 10 μg/ml tetracycline and arabinose to a final concentration of 0.01% (w/v). Incubation was performed at 20° C. with shaking (250 rpm) for about 60 hours.
2. The cells were then harvested by centrifugation at 4° C.
3. The cell pellet was re-suspended in 300 micro-liters of 20% sucrose (w/v) containing 1 mM EDTA in 200 mM Tris-HCl at pH7.5, and incubated at room-temperature for 15 minutes.
4. Periplasmic shockate was generated by the addition of 450 micro-liters of distilled water, and a further incubation at room-temperature for 15 minutes.
5. Cellular remains were removed by centrifugation, and the supernatant assayed for enzyme activity as soon as possible after preparation and kept at 4° C. prior to assay.

TABLE 4

Activity relative to D253K HCPB or D253R HCPB in crude *E. coli* periplasmic shockate

| Mutation | Hipp-Glu | Hipp-Asp | Hipp-Arg |
|---|---|---|---|
| [Q54R, D145A, D253K] | a | a | |
| [I245S, D253K] | a | a | |
| [I245A, D253K] | a | a | |
| [I245H, D253K] | a | NAD | |
| [A248H, D253K] | a | NAD | |
| C288S | | | c |
| C288A | | | d |
| [G251K, D253R] | a | NAD | |
| [I201S, D253K] | NAD | b | |
| [G251Q, D253K] | a | NAD | |
| [G251S, D253K] | e | a | |
| [G251V, D253K] | a | NAD | |
| [A248N, G251S, D253K] | a | a | |

TABLE 4-continued

Activity relative to D253K HCPB or D253R HCPB in crude *E. coli* periplasmic shockate

| Mutation | Hipp-Glu | Hipp-Asp | Hipp-Arg |
|---|---|---|---|
| [A248S, G251S, D253K] | a | NAD | |
| [I201T, D253R] | b | b | | a = activity equivalent to D253K HCPB
b = activity equivalent to D253R HCPB
c = activity 75% of mature HCPB (described in Reference Examples 7 and 8)
d = activity 25% of mature HCPB (described in Reference Examples 7 and 8)
e = >10 times the activity of D253K HCPB
NAD = No activity detected

Example 17
Assay of Activity of a Range of Human CPB Mutants Against Hipp-Glu, Hipp-Asp and Hipp-Arg Prodrug Analogues This example builds on a range of mutants described in Example 6.

Purified mutants of human CPB (D253K; [G251K, D253R]; [G251N,D253R]; [I201S,D253K]; [G251N, D253K]; [Q54R,D145A,D253K]; [G251T,D253K]; [G251S,D253K]; [A248N,G251N,D253K]; [A248S, G251N,D253K] and [S205N,G251N,D253K]—described in Examples 3, 12, 13, 16, 28, 30, 31, 32 and 33) were assayed for their ability to convert hippuryl-L-glutamic acid (Hipp-Glu—Reference Example 1), hippuryl-L-aspartic acid (Hipp-Asp—Reference Example 2) and hippuryl-L-arginine (Sigma Chemical Company—cat no. H6625) to hippuric acid using a HPLC based assay similar to that described in Example 6.

The reaction mixture (500 μl) contained mutant human CPB (0.01–12.5 μg depending on mutant) and 0.5 mM Hipp-Glu or Hipp-Asp or Hipp-Arg in 0.025M Tris-HCL, pH7.5. Samples were incubated for 30 minutes at 37° C. The reactions were terminated by the addition of 500 μl of 40% methanol, 60% distilled water, 0.2% trifluoro acetic acid and the amount of hippuric acid generated was quantitated by HPLC as described in Example 6 but using a mobile phase of 20% methanol, 80% 50 mM phosphate buffer, pH 6.5. Hippuric acid was detected at 230 nm. The results are shown in Table 5 and are expressed as the percentage conversion of substrate into product in 30 minutes at 37° C.

TABLE 5

Conversion of Hipp-Glu, Hipp-Asp or Hipp-Arg by HCPB mutants.

| Mutant | Concentration (μg/ml) | Hipp-Glu | Substrates Hipp-Asp (% conversion) | Hipp-Arg |
|---|---|---|---|---|
| D253K | 25 | 79 | 22 | 0 |
|  | 2.5 | 14.6 | 2.9 | 0 |
| [G251K, D253R] | 25 | 5.5 | 0.2 | 0 |
|  | 2.5 | 3.2 | 0.2 | 0 |
| [G251N, D253R] | 25 | 57 | 9.4 | 0 |
|  | 2.5 | 8.8 | 1.4 | 0 |
| [I201S, D253K] | 25 | 27.8 | 33.1 | 0 |
|  | 2.5 | 4.6 | 5.8 | 0 |
| [G251N, D253K] | 25 | 100 | 8.3 | 1.8 |
|  | 2.5 | 62.4 | 1.9 | 0.4 |
| [G251R, D145A, D253K] | 25 | 90 | 30 | 0 |
|  | 2.5 | 26 | 5.2 | 0 |
| [G251T, D253K] | 25 | 100 | 14 | 5.2 |
|  | 0.02 | 8.2 | 0 | 0 |

TABLE 5-continued

Conversion of Hipp-Glu, Hipp-Asp or Hipp-Arg by HCPB mutants.

| Mutant | Concen-tration (μg/ml) | Hipp-Glu | Substrates Hipp-Asp (% conversion) | Hipp-Arg |
|---|---|---|---|---|
| [G251S, D253K] | 25 | 100 | 2.8 | 0.8 |
|  | 0.25 | 14.5 | 0 | 0 |
| [A248N, G251N, D253K] | 25 | 100 | 2.5 | 1.4 |
|  | 0.25 | 25.3 | 0.6 | 0 |
| [A248S, G251N, D253K] | 25 | 86 | 1.3 | 0 |
|  | 0.5 | 10.7 | 0 | 0 |
| [S205N, G251N, D253K] | 25 | 85 | 0.48 | 0.2 |
|  | 0.5 | 7.9 | 0 | 0 |

The data demonstrate that all 11 mutants have the ability to turn over Hipp-Glu and Hipp-Asp substrates and all show minimal or no ability to convert Hipp-Arg (substrate for native human CPB, Example 6). The best mutants in this assay were [G251T,D253K] for Hipp-Glu and [I201S, D253K] for Hipp-Asp.

Example 18
Assay of Activity of IG251T,D253K]HCPB and Other HCPB Mutants

The activity of [G251T,D253K]HCPB was measured using the assay conditions described in Example 17 but using either 50 μl of a neat or 1 in 10 or 1 in 100 dilution of [G251T,D253K]HCPB crude E.coli periplasmic shockate (shockate) sample in place of purified enzyme. Samples were incubated for 24 h at 37° C. For comparison D253K HCPB was assayed in a similar assay except that the reaction volume was reduced to 250 μl and contained 125 μl neat D253K shockate sample. For other HCPB mutants, the reaction volume was 250 μl and contained 125 μl of neat shockate or 1 in 50 dilution of shockate. The shockate samples were prepared as described in Example 16. The amount of Hippuric acid produced in 24 h was quantified by HPLC as described in Example 17 and the results are shown in Table 6 and are expressed as the percentage conversion of substrate into product in 24 h at 37° C.

The data demonstrate that the mutant [G251T,D253K] is at least 50 fold more active than D253K at converting Hipp-Glu to hippuric acid. The [G251T,D253K] mutant is over 900 fold more active against Hipp-Glu compared to Hipp-Arg (substrate for native CPB, Example 6).

Example 19
Cytotoxicity of Prodrug of Example 21 and Corresponding Drug of Example 22 in LoVo Tumour Cells The differential cytotoxicity of the prodrug of Example 21 and the drug of Example 22 in LoVo human colorectal tumour cells was demonstrated as described in Example 9.

LoVo tumour cells treated with the prodrug had an IC50 of 905 μM while the cells treated with the drug had an IC50 of 84 μM (mean data from 3 separate studies). A representative study is shown in FIG. 15. Thus the prodrug was over 10 fold less cytotoxic to LoVo colorectal tumour cells than the drug demonstrating its utility for use with suitable mutants of HCPB described herein.

When the D253K HCPB mutant, produced as described in Example 3, was added to the assay wells containing LoVo tumour cells and the prodrug of Example 21 enhanced cell kill was seen. Addition of between 2.4 and 11.75 μg/ml D253K HCPB to the prodrug (500 μM) resulted in toxicity which matched that seen with 200 μM of the active drug of Example 22 (FIG. 16). These studies further demonstrate the potential of mutant enzymes of human CPB to selectively convert a relatively non-cytotoxic prodrug into a potent cytotoxic drug capable of killing tumour cells.

Example 20
Conversion of Prodrug of Example 24 by D253K HCPB and Other HCPB Mutants The ability of purified D253K HCPB (Example 3) to convert the prodrug of Example 24 to the drug of Example 25 was demonstrated as follows.

A reaction mixture (500 μl) containing D253K HCPB (7.5 μg), 0.5 mM prodrug in 0.025M Tris-HCl buffer, pH 7.5 was incubated for 5 minutes at 37° C. The reaction was stopped by adding MeCN (500 μl) plus 0.2% Trifluoroacetic acid. The amount of drug produced was then quantified by HPLC.

HPLC separation was carried out as described in Example 6 except that a mobile phase of 70% MeCN, 30% distilled water and 0.1% trifluoroacetic acid was used to achieve

TABLE 6

Conversion of Hipp-Glu, Hipp-Asp and Hipp-Arg by [G251T, D253K] HCPB and other HCPB mutants

| Mutant | Shockate concentration in reaction mixture (%) | Hipp-Glu | Substrates Hipp-Asp (% conversion) | Hipp-Arg |
|---|---|---|---|---|
| [D253K] | 50 | 7.4 | 2.0 | 0 |
| [G251T, D253K] | 10 | 100 | 2.6 | 0.8 |
|  | 1 | 93 | 0 | 0.1 |
|  | 0.1 | 60 | — | — |
| [G251N, D253K, T266G] | 50 | 0.95 | 3.4 | — |
| [G251S, D253K] | 50 | 93.8 | 1.6 | — |
|  | 1 | 5 | — | — |
| [A248N, G251T, D253K] | 50 | 95 | 1 | — |
|  | 1 | 53.5 | — | — |
| [A248S, G251T, D253K] | 50 | 91.3 | 0.5 | — |
|  | 1 | 20 | — | — |
| [G251T, D253R] | 50 | 65.4 | 14.6 | — |
| [A248N, G251N, D253K] | 50 | 63.9 | 0 | — |
| [A248S, G251N, D253K] | 50 | 46.1 | 1 | — |
| [S205N, G251N, D253K] | 50 | 14.1 | 0 | — | separation of prodrug (retention time 3.8 minutes) and drug (retention time 4.9 minutes) and the compounds were detected at 260 nm. The amount of drug produced was quantified from calibration curves generated with known amounts of drug.

D253K HCPB (15 µg/ml) resulted in hydrolysis of 70.4% of prodrug to drug in this assay in 5 minutes at 37° C. (drug concentration at end of reaction was 0.352 mM).

The conversion of prodrug to drug by other HCPB mutants using the same assay conditions is shown in Table 7. The amount of [Q54R,D145A,D253K]HCPB and [G251T,D253K]HCPB mutants was reduced to 0.75 µg in the reaction mixture.

TABLE 7

Conversion of prodrug of Example 24 by HCPB mutants

| Mutant | Concentration (µg/ml) | Prodrug Hydrolysis (%) |
| --- | --- | --- |
| D253K | 15 | 70.4 |
| D253R | 15 | 18.3 |
| [G251K,D253R] | 15 | 16.2 |
| [G251N,D253R] | 15 | 66.7 |
| [I201S,D253K] | 15 | 72.6 |
| [G251N,D253K] | 15 | 75.9 |
| [Q54R,D145A,D253K] | 1.5 | 26.0 |
| [G251T,D253K] | 1.5 | 36.0 |

The data demonstrate that HCPB mutants can convert prodrug to drug providing further evidence that the activity seen against the model substrates Hipp-Glu and Hipp-Asp is applicable to mustard prodrugs.

Example 21

Preparation of N-[N-(4-{4-[bis-(2-chloroethyl)-amino]-3-methyl-phenoxy}-benzoyl)-L-alanine]-L-glutamic acid (see FIG. 17 for reaction scheme)

To a solution of N-[N-(4-{4-[bis-(2-chloroethyl)-amino]-3-methyl-phenoxy}-benzoyl)-L-alanine-L-glutamic acid dibenzyl ester (compound 8; 130 mg) in ethyl acetate (5 mL) was added 30% Pd/C (50% moist; 25 mg). The mixture was stirred under an atmosphere of hydrogen for 1 hour. The catalyst was removed by filtration through CELITE (diatomaceous silica) and the filtrate evaporated to dryness to give the titled compound (compound 11) as an oil, 88 mg (88% yield).

NMR DMSOd$_6$ 7.9–6.6 (m, 7H); 4.85 (m, 1H); 4.6 (m, 1H); 3.4 (m, 8H); 2.25 (s, 3H); 2.4–1.9 (m, 4H); 1.45 (d, 3H);

MS ESI, 566 [M-H]⁻

Starting material compound 8 was made as follows.

4-hydroxybenzoic acid (13.8 g, 0.1 mole) was dissolved in methanol and to this solution was added, sodium methoxide (10.8 g, 0.2 mole). The solution was then evaporated to dryness. To the resulting solid was added DMF (500 mL) followed by 4-fluoro-2-methyl-1-nitrobenzene (available from Aldrich under 5-fluoro-2-nitro-toluene) (10.2 mL 0.1 mole). The mixture was heated at 125° C. for 2 hours, cooled and poured into 3 L of water, acidified to pH2 with 2M HCl and extracted twice with ethyl acetate. The combined organic layers were washed with water, dried and evaporated to dryness. The resulting solid was triturated with ether to give 4-(3-methyl-4-nitro-phenoxy)-benzoic acid (compound 1) as a white solid 6.1 g (22% yield; melting point= 187–190° C.).

To a solution of isobutylene (34 g) in dichloromethane (100 mL) was added compound 1 (5 g), at 5° C., followed by concentrated sulphuric acid (0.5 mL). The mixture was stirred at ambient temperature for 2 days and poured into saturated sodium bicarbonate solution (200 mL). The aqueous layer was extracted with dichloromethane and the combined organic extracts were dried and evaporated to give an an oil. The oil was chromatographed with 5% ethyl acetate in hexane to give 4-(3-methyl-4-nitro-phenoxy)-benzoic acid tert-butyl ester (compound 2), 2.5 g (42% yield; melting point=81–83° C.).

To a solution of compound 2 (2.15 g 5 mM) in ethyl acetate (35 mL) was added 30% Pd/C (50% moist) (400 mg). The mixture was stirred under an atmosphere of hydrogen for 2 hours. The mixture was filtered through CELITE and the filtrate evaporated to give 4-(4-amino-3-methyl-phenoxy)-benzoic acid tert-butyl ester (compound 3) as a solid (1.9 g, 99% yield). Melting point, 84–86° C.

To a solution of compound 3 (2 g) in 1:1 acetic acid/water (30 mL) was passed in ethylene oxide (5 g). After standing at ambient temperature for 2 days the mixture was poured into saturated sodium bicarbonate solution (200 mL) and extracted twice with ethyl acetate. The combined organic extracts were washed with water, dried and evaporated to give 4-{4-[bis(2-hydroxyethyl)-amino]-3-methyl-phenoxy)-benzoic acid tert-butyl ester (compound 4) as an oil (2.5 g, 99% yield).

NMR CDCl$_3$ 8.0 (d, 2H); 7.3–6.9 (m, 7H); 3.6 (t, 4H); 3.2 (t, 4H); 2.3 (s, 3H); 1.5 (s, 9H).

To a solution of compound 4 (2.5 g) in 1:1 acetonitrile/carbon tetrachloride (90 mL) was added imidazole (1.7 g) and triphenylphosphene (6.6 g). The mixture was stirred at ambient temperature for 3 hours and evaporated to dryness. The residue was partitioned between 1M citric acid solution and ethyl acetate. The organic layer was washed with water, dried and evaporated to dryness. The residue was chromatographed with hexane/ethyl acetate (9:1) to give 4-{4-[bis(2-chloroethyl)-amino]-3-methyl-phenoxy)-benzoic acid tert-butyl ester (compound 5) as an oil (1.2 g, 44% yield).

NMR CDCl$_3$ 7.95 (d, 2H); 7.2–6.9 (m, 7H); 3.4 (m, 8H); 2.3 (s, 3H); 1.6 (s, 9H).

A solution of compound 5 in dichloromethane (5 ml) and trifluoroacetic acid (10 mL) was allowed to stir at ambient temperature for 2 hours. The mixture was evaporated to dryness, azeotroped twice with ethyl acetate to give 4-{4-[bis(2-chloroethyl)-amino]-3-methyl-phenoxy)-benzoic acid (compound 6) as a solid trifluoroacetate salt (1.0 g, 73% yield). Melting point, 91–3° C.

To a solution of N-Boc-L-Alanine-L-Glutamic acid dibenzyl ester (Beilharz et al., 1983, 36, 751–8) (compound 7, 250 mg, 0.5 mM) in dichloromethane (2 mL) was added trifluoroacetic acid (4 mL). The solution was allowed to stand at ambient temperature for 1 hour and then evaporated to dryness. The residue was re-dissolved in ethyl acetate, washed with saturated sodium bicarbonate solution, dried and evaporated to give an oil (compound 7 with BOC group removed). This oil in DMF (2 mL) was added to compound 6 (255 mg) in DMF (3 mL), followed by hydroxybenzotriazole (70 mg), 1-(3-Dimethylaminopropyl)-3-ethylcarbodiimide hydrochloride (DECI; 115 mg) and triethylamine (0.18 mL). The mixture was stirred at ambient temperature for 1 hour, poured into saturated sodium bicarbonate solution (100 mL) and ethyl acetate (100 mL). The organic layer was separated, washed with water and then 0.5M citric acid, dried and evaporated to dryness. The residue was chromatographed with ethyl acetate/hexane (1:1) to give the desired starting material as an oil (150 mg, 40% yield).

NMR CDCl₃ 7.8 (d, 2H); 7.4–6.7 (m, 7H); 5.2 (s, 2H); 5.0 (s, 2H); 4.7 (m, 2H); 3.4 (m, 8H); 2.3 (s, 3H); 2.45–2.0 (m, 4H); 1.4 (d, 3H).

Example 22

Preparation of N-(4-{4-[bis-(2-chloroethyl)-amino]-3-methyl-phenoxy}-benzoyl)-L-alanine (see FIG. 17 for reaction scheme)

N-(4-{4-[bis-(2-chloroethyl)-amino]-3-methyl-phenoxy}-benzoyl)-L-alanine-tert-butyl ester (400 mg; compound 9) was dissolved in dichloromethane (4 ml) and trifluoroacetic acid (8 ml) was added. The mixture was allowed to stand at ambient temperature for 1 hour, evaporated to dryness and azeotroped twice with ethyl acetate to give the titled compound (compound 10; the drug corresponding with the prodrug of Example 21) as an oil (0.43 g, 52% yield).

NMR DMSOd₆ 8.5 (d, 1H); 7.8–6.5 (m, 7H); 4.4 (m, 1H); 3.55 (t, 4H); 3.35 (t, 4H); 2.3 (s, 3H); 1.4 (d, 3H).

MS (M+H)⁺, 439

Starting material compound 9 was prepared as follows.

To a mixture of 4-{4-[bis(2-chloroethyl)-amino]-3-methyl-phenoxy)-benzoic acid (compound 6 in example 21) (586 mg, 1 mmole) in dimethylformamide (2 mL) was added hydroxybenzotriazole (135 mg), 1-(3-Dimethylaminopropyl)-3-ethylcarbodiimide hydrochloride (230 mg), then L-alanine-tert-butyl ester hydrochloride (181 mg) and triethylamine (0.54 mL). The mixture was stirred at ambient temperature for 2 hours, poured into saturated sodium bicarbonate solution (60 mL), extracted twice with ethyl acetate and the combined extracts washed with water, washed with IM citric acid solution, dried and evaporated to dryness. The residue was chromatographed with hexane/ethyl acetate (4:1) to give the desired starting material as an oil (0.4 g, 81% yield).

NMR CDCl₃ 7.8 (d, 2H); 7.3–6.7 (m, 7H); 4.6 (m, 1H); 3.4 (m, 8H); 2.3 (s, 3H); 1.5 (d, 3H); 1.5 (s, 9H).

Example 23

Anti-tumour Activity of Prodrugs and Humanised Antibody-mutant HCPB Fusion Protein in Xenografted Mice The anti-tumour efficacy of suitable prodrugs and humanised antibody-mutant HCPB fusion protein (Example 10) can be demonstrated in the following model.

LoVo colorectal tumour cells (ECACC no. 87060101) (1×10⁷) are injected s.c. into athymic nude mice. When the tumours are 4–5 mm in diameter the conjugate is administered i.v. at doses between 10–100 mg/kg. Following localisation of the fusion protein to the tumours and allowing a suitable time interval for residual conjugate to clear from the bloodstream and normal tissues (1–4 days) the prodrug is administered either i.v or i.p. to the mice in doses ranging between 10–1000 mg/kg either as a single or multiple doses. The combination of antibody-enzyme fusion protein and prodrug cause the tumours to grow significantly slower than untreated control tumours or tumours treated with either the same dose of conjugate or prodrug alone. These studies demonstrate that the combination of the humanised antibody-mutant CPB fusion protein and the mutant CPB prodrugs result in significant anti-tumour activity.

Example 24

Preparation of N-[N-(4-{4-[bis-(2-chloroethyl)-amino]-phenoxy}-benzoyl)-L-alanine]-L-glutamic acid The titled compound was prepared in an analogous manner to that set out in Example 21 but substituting 4-(4-nitrophenoxy)-benzoic acid (Ravick et al. (1933), JACS, 55, 1289–1290) for 4-(3-methyl-4-nitrophenoxy)-benzoic acid (compound 1 in Example 21).

NMR DHSOd₆, 8.4 (d, 1H); 8.3 (d, 1H); 7.8 (d, 1H); 7.05–6.75 (m, 6H); 4.5 (m, 1H); 4.25 (m, 1H); 3.7 (s, 8H); 2.4–1.6 (m, 4H); 1.4 (d, 3H).

MS ESP, 551[M-H]⁻

Example 25

Preparation of N-(4-{4-[bis-(2-chloroethyl)-amino]-phenoxy}-benzoyl)-L-alanine

The titled compound (which is the drug corresponding with the prodrug of Example 24) was prepared in an analogous manner to that set out in Example 22 but substituting 4-{4-[bis(2-chloroethyl)-amino]-phenoxy)-benzoic acid (which is prepared as an intermediate in Example 24) for 4-{4-[bis(2-chloroethyl)-amino]-3-methyl-phenoxy)-benzoic acid.

NMR CDCl₃, 7.75 (d, 2H); 7.0–6.4 (m, 6H); 4.6 (m, 1H); 3.6–3.4 (m, 8H); 1.6 (d, 2H).

MS ESP, 423 [H-H]⁻

Example 26

Purification of D253R HCPB-His₆-cMyc from *E.coli*

The procedure described in Example 11 was repeated with plasmid pICI1713 replaced by pICI1746 (described in Example 2). Twelve 2 L Erlenmeyer flasks containing 600 ml of L-tetracycline were used for the fermentation in place of the nine flasks used in Example 11.

Recombinant *E.coli* cell paste was taken from storage at −70° C. and allowed to thaw. The weight of cell paste was measured and found to be 82.4 g. The paste was resuspended with the addition of buffer A [200 mM Tris-HCl (pH 8.0), 20% sucrose) to give a resuspended volume of 130 ml. The cell suspension was incubated at room temperature for 20 minutes with occasional gentle mixing before an equal volume of distilled water, at room temperature, was added and thoroughly mixed in. The cell suspension was again incubated at room temperature for 20 minutes with occassional gentle mixing. The resulting crude osmotic shockate was clarified by centrifugation at 98000×g for 90 minutes at 4° C. after which the supernatant was decanted off from the pelleted insoluble fraction. The supernatant was diluted 1:1 with 10 mM Tris-HCl, 500 mM sodium chloride, pH 8.0 (Buffer B), adjusted to pH 8.0 to a total volume of 500 ml and loaded, over night, at 0.5 ml/min, onto a Carboxypeptidase inhibitor affinity column. The column having been prepared according to instructions with the CNBr-activated Sepharose 4B (a preactivated 4% agarose gel for immobilisation of ligands containing primary amines; Pharmacia Cat. No. 17-0430-01) and carboxypeptidase inhibitor from potato tuber (c-0279, Sigma). The amount of matrix used for this size of carboxypeptidase purification was 15 ml packed in a Pharmacia XK 16 column. To produce a 15 ml quantity of matrix, 5 g of dry matrix and 80 mg of Carboxypeptidase inhibitor were used. The procedure for preparing the affinity column was as follows:

Freeze dried matrix (5 g) was suspended in 1 mM HCl. The swollen gel was washed on a sintered glass filter with 1 mM HCl (11) added in several aliquots. The carboxypeptidase inhibitor (80 mg) was dissolved in 0.1M sodium bicarbonate (pH 8.3) containing 0.5M NaCl (coupling buffer; 25 ml) then mixed with the gel in a stoppered vessel. The mixture was rotated end-over-end for 1 h at room temperature or 4° C. for 18 h then excess ligand was washed away with at least 5 gel volumes of coupling buffer. The gel was transferred to 0.1M Tris-HCl (pH 8.0) and left to stand for 2 h at room temperature, then washed with at least 5 gel volumes of 0.1M acetate buffer (pH 4.0) containing 0.5 h NaCl followed by at least 5 gel volumes of 0.1M Tris-HCl (pH 8.0) containing 0.5M NaCl.

The column was pre-equilibrated with buffer B at 4° C. After loading the supernatant, the column was washed until the absorbance of the flow through was back to baseline before the bound material was eluted from the column by elution buffer (100 mM sodium carbonate, 500 mM sodium chloride, pH 11.4) at 4° C., with 1 ml fractions being collected. The eluted fractions were frozen at −20° C. after samples were taken to determine those containing the recombinant carboxypeptidase B. This was accomplished by Western blot analysis using an anti-c-myc tag antibody (9E10), followed by an anti-mouse horse radish peroxidase conjugate (a-9044, Sigma) that gave a colour reaction with exposure to 4-chloronaphthol and hydrogen peroxide, or by silver-stained polyacrylamide gel electrophoresis. Fractions 20 to 66 were determined to contain the recombinant carboxypeptidase B. The diluted supernatant collected from the column during the initial loading was re-passaged over the column, after the column had been re equilibrated. Elution conditions and analysis of the fractions collected were identical to those from the first elution. Fractions 25 to 60 were determined to contain the recombinant carboxypeptidase B. These were pooled with the fractions from the first passage, the pH adjusted to pH7.5 and concentrated using a Millipore Centrifugal Ultrafree −20 (a 10,000 molecular weight cut off filtration device) before being snap-frozen and stored at −80° C. The purification detailed here provided 3.5 mg/ml of D253R mutant HCPB at a purity of 87% in a volume of 550 microliters.

Example 27

Purification of [G251N,D253K]HCPB-$His_6$-cMyc from *E.coli*

The procedure described in Example 26 was repeated with plasmid pICI1746 replaced by pMC43.1 (described in Example 13). The weight of cell paste was 94 g which was resuspended in 110 ml of buffer A. The volume of osmotic shockate, after dilution with buffer B, loaded onto the potator inhibitor column was 500 ml. In the first elution, fractions 10 to 27 were collected. In the second passage fractions 10 to 39 were collected on elution. The purification provided 1.24 mg/ml of [G251N,D253K]HCPB at a purity of 95% in a volume of 900 microliters.

Example 28

Purification of [G251T,D253K]HCPB-$His_6$-cMyc from *E.coli*

The procedure described in Example 26 was repeated with plasmid pICI1746 replaced by pMC46.4.1 (described in Example 14). The weight of cell paste was 46 g which was resuspended in 65 ml of buffer A. The volume of osmotic shockate, after dilution with buffer B, loaded onto the potator inhibitor column was 260 ml. In the first elution, fractions A to 28 were collected. In the second passage fractions 41 to 79 were collected on elution. The purification provided 0.67 mg/ml of [G251T,D253K]HCPB at a purity of 95% in a volume of 500 microliters.

Example 29

Pharmaceutical Composition

The following illustrates a representative pharmaceutical dosage form of the present invention which may be used for therapeutic purpose in humans.

Injectable Solutions i) A sterile aqueous solution, for injection, containing per ml of solution:

Antibody-enzyme of Example 10 1.0 mg

Sodium acetate trihydrate 6.8 mg

Sodium chloride 7.2 mg

Tween 20 0.05 mg

A typical dose of conjugate is 30 mg followed 3 days later by prodrug.

ii) Assemble the following for final prodrug dosage form preparation: glass vials (3×20 ml) each containing 600 mg of prodrug of Example 21; 3 ampoules containing 11 ml of 2.15% (w/v) sodium hydrogen carbonate; needles (3×18 G); hydrophobic filters for venting the vials; and 3×single use sterile 0.22 micron filters for aqueous solutions. All materials must be stored at 2–8° C.

These operations are preferably to be performed under sterile conditions. No more than 1 hour prior to dosing, one vial of prodrug is vented with a needle and hydrophobic filter. Sterile 2.15% w/v sodium hydrogen carbonate (10 ml) is then added directly through the bung via a syringe and needle. With the vent still in place the vial is swirled gently to obtain a clear solution (this will be 50 mg/ml as free base). The required-dose volume is withdrawn into a sterile syringe through a sterile filter. The filter is then replaced by a sheathed sterile needle and the syringe unit kept cool prior to administration. Each remaining vial is prepared in an identical manner at intervals of one hour to allow for example three separate doses to be given 1 hour apart.

Example 30

Cloning, Expression and Purification of [G251S,D253K]HCPB-(His )$_6$-c-myc from *E.coli*

The method of cloning and expressing the [G251S,D253K]HCPB in *E.coli* was very similar to the method described in Reference Example 8. The gene for [G251S,D253K]HCPB was prepared as described in Example 2 but the starting material for PCR site directed mutagenesis was the [D253K]HCPB gene in plasmid pICI1713 (described in Example 1) in place of pICI1712. However, in this case site directed mutagenesis was used during the PCR amplification of the gene to change the codon at amino acid position 251 in the mature gene from Glycine to Serine(GGC to TCT), the G251S change. Two PCR mixtures were prepared, in a manner similar to that described in Reference Examples 7 and 8. In the first reaction primers were 2264 (SEQ ID NO: 48) and 1038 (SEQ ID NO: 68, replacing SEQ ID NO: 61). In the second reaction primers were 6HIS9EIOR$^1$BS1 (SEQ ID NO: 42) and 54 (SEQ ID NO: 75, replacing SEQ ID NO: 62). In both reactions the starting DNA was pICI1713.

Methods of PCR, cloning, expression and identification were the same as for Example 14. From the sequencing results a clone containing a plasmid with the required [G251S,D253K]HCPB gene sequence was selected, and is known as pMC49.2.

For purification of [G251S,D253K]HCPB, the procedure described in Example 26 was repeated with plasmid pICI1746 replaced by pMC49.2. The weight of cell paste was 77 g which was resuspended in 100 ml of buffer A. The volume of osmotic shockate, after dilution with buffer B, loaded onto the potator inhibitor column was 395 ml. In the first elution, fractions 11 to 40 were collected. In the second passage fractions 12 to 33 were collected on elution. The purification provided 1.7 mg/ml of [G251S,D253K]HCPB at a purity of 86% in a volume of 500 microliters.

Example 31
Cloning, Expression and Purification of [A248N,G251N, D253K]HCPB-((His)$_6$-c-myc from *E.coli*

The method of cloning and expressing the [A248N, G251N,D253K]HCPB in *E.coli* was very similar to the method described in Reference Example 8. The gene for [A248N,G251N,D253K]HCPB was prepared as described in Example 2 but the starting material for PCR site directed mutagenesis was the [G251N,D253K]HCPB gene in plasmid pMC43.1 (described in Example 13) in place of pICI1712. However, in this case site directed mutagenesis was used during the PCR amplification of the gene to change the codon at amino acid position 248 in the mature gene from Alanine to Asparagine (GCT to AAC), the G248N change. Two PCR mixtures were prepared, in a manner similar to that described in Reference Examples 7 and 8. In the first reaction primers were 2264 (SEQ ID NO: 48) and 1024 (SEQ ID NO: 76, replacing SEQ ID NO: 61). In the second reaction primers were 6HIS9E10R1BS1 (SEQ ID NO: 42) and 1028 (SEQ ID NO: 77, replacing SEQ ID NO: 62). In both reactions the starting DNA was pMC43.1.

Methods of PCR, cloning, expression and identification were the same as for Example 14. From the sequencing results a clone containing a plasmid with the required [A248N,G251N,D253K]HCPB gene sequence was selected, and is known as pMC50.2.

For purification of [A248N,G251N,D253K]HCPB, the procedure described in Example 26 was repeated with plasmid pICI1746 replaced by pMC50.2. The weight of cell paste was 83 g which was resuspended in 100 ml of buffer A. The volume of osmotic shockate, after dilution with buffer B, loaded onto the potator inhibitor column was 560 ml. In the first elution, fractions 23 to 40 were collected. In the second passage fractions 18 to 40 were collected on elution. The purification provided 1.0 mg/ml of [A248N, G251N,D253K]HCPB at a purity of 90% in a volume of 1000 microliters.

Example 32
Cloning, Expression and Purification of [A248S,G251N, D253K]HCPB-(His)$_6$-c-Myc from *E.coli*

The method of cloning and expressing the [A248S, G251N,D253K]HCPB in *E.coli* was very similar to the method described in Reference Example 8. The gene for [A248S,G251N,D253K]HCPB was prepared as described in Example 2 but the starting material for PCR site directed mutagenesis was the [G251N,D253K]HCPB gene in plasmid pMC43.1 (described in Example 13) in place of pICI1712. However, in this case site directed mutagenesis was used during the PCR amplification of the gene to change the codon at amino acid position 248 in the mature gene from Alanine to Serine (GCT to TTC), the G248S change. Two PCR mixtures were prepared, in a manner similar to that described in Reference Examples 7 and 8. In the first reaction primers were 2264 (SEQ ID NO: 48) and 1024 (SEQ ID NO: 76, replacing SEQ ID NO: 61). In the second reaction primers were 6HIS9E10R1BS1 (SEQ ID NO: 42) and 1030 (SEQ ID NO: 78, replacing SEQ ID NO: 62). In both reactions the starting DNA was pMC43.1.

Methods of PCR, cloning, expression and identification were the same as for Example 14. From the sequencing results a clone containing a plasmid with the required [A248S,G251N,D253K]HCPB gene sequence was selected, and is known as pMC51.2.

For purification of [A248S,G251N,D253K]HCPB, the procedure described in Example 26 was repeated with plasmid pICI1746 replaced by pMC51.2. The weight of cell paste was 71.5 g which was resuspended in 100 ml of buffer A. The volume of osmotic shockate, after dilution with buffer B, loaded onto the potator inhibitor column was 520 ml. In the first elution, fractions 10 to 40 were collected. In the second passage fractions 10 to 32 were collected on elution. In a third passage fractions 15 to 40 were collected on elution. The purification provided 0.8 mg/ml of [A248S, G251N,D253K]HCPB at a purity of 80.5% in a volume of 1500 microliters.

Example 33
Cloning, Expression and Purification of [S205N,G251N, D253K]HCPB-(His)$_6$-c-Myc from *E.coli*

The method of cloning and expressing the [S205N, G251N,D253K]HCPB in *E.coli* was very similar to the method described in Reference Example 8. The gene for [S205N,G251N,D253K]HCPB was prepared as described in Example 2 but the starting material for PCR site directed mutagenesis was the [G251N,D253K]HCPB gene in plasmid pMC43.1 (described in Example 13) in place of pICI1712. However, in this case site directed mutagenesis was used during the PCR amplification of the gene to change the codon at amino acid position 205 in the mature gene from Serine to Asparagine (TCA to AAC), the S205N change. Two PCR mixtures were prepared, in a manner similar to that described in Reference Examples 7 and 8. In the first reaction primers were 2264 (SEQ ID NO: 48) and 1010 (SEQ ID NO: 79, replacing SEQ ID NO: 61). In the second reaction primers were 6HIS9E10R1BS1 (SEQ ID NO: 42) and 1016 (SEQ ID NO: 80, replacing SEQ ID NO: 62). In both reactions the starting DNA was pMC43.1.

Methods of PCR, cloning, expression and identification were the same as for Example 14. From the sequencing results a clone containing a plasmid with the required [S205N,G251N,D253K]HCPB gene sequence was selected, and is known as pMC52.1.

For purification of [S205N,G251N,D253K]HCPB, the procedure described in Example 26 was repeated with plasmid pICI1746 replaced by pMC52.1. The weight of cell paste was 77 g which was resuspended in 100 ml of buffer A. The volume of osmotic shockate, after dilution with buffer B, loaded onto the potator inhibitor column was 420 ml. In the first elution, fractions 10 to 40 were collected. In the second passage fractions 12 to 29 were collected on elution. The purification provided 0.8 mg/ml of [S205N, G251N,D253K]HCPB at a purity of 85% in a volume of 650 microliters.

Example 34
Cloning and Expression of [G251T,D253R]HCPB-(His)$_6$-c-Myc from *E.coli*

The method of cloning and expressing the [G251T, D253R]HCPB in *E.coli* was very similar to the method described in Reference Example 8. The gene for [G251T, D253R]HCPB was prepared as described in Example 2 but the starting material for PCR site directed mutagenesis was the [D253R]HCPB gene in plasmid pICI1746 (described in Example 2) in place of pICI1712. However, in this case site directed mutagenesis was used during the PCR amplification of the gene to change the codon at amino acid position 251 in the mature gene from Glycine to Threonine (GGC to ACT), the G251T change. Two PCR mixtures were prepared, in a manner similar to that described in Reference Examples 7 and 8. In the first reaction primers were 2264 (SEQ ID NO: 48) and 1038 (SEQ ID NO: 68, replacing SEQ ID NO: 61). In the second reaction primers were 6HIS9E10R1BS1 (SEQ ID NO: 42) and 794 (SEQ ID NO: 81, replacing SEQ ID NO: 62). In both reactions the starting DNA was pICI1746.

Methods of PCR, cloning, expression and identification were the same as for Example 14. From the sequencing results a clone containing a plasmid with the required [G251T,D253R]HCPB gene sequence was selected, and is known as pMC55.2.

Example 35

Cloning and Expression of [I201T,D253R]HCPB-(His)$_6$-c-Myc from E.coli

The method of cloning and expressing the [I201T,D253R] HCPB in E.coli was very similar to the method described in Reference Example 8. The gene for [I201T,D253R]HCPB was prepared as described in Example 2 but the starting material for PCR site directed mutagenesis was the [D253R] HCPB gene in plasmid pICI1746 (described in Example 2) in place of pICI1712. However, in this case site directed mutagenesis was used during the PCR amplification of the gene to change the codon at amino acid position 201 in the mature gene from Isoleucine to Threonine (ATC to ACT), the I201T change. Two PCR mixtures were prepared, in a manner similar to that described in Reference Examples 7 and 8. In the first reaction primers were 2264 (SEQ ID NO: 48) and 1003 (SEQ ID NO: 82, replacing SEQ ID NO: 61). In the second reaction primers were 6HIS9E10R1BS1 (SEQ ID NO: 42) and 795 (SEQ ID NO: 83, replacing SEQ ID NO: 62). In both reactions the starting DNA was pICI1746.

Methods of PCR, cloning, expression and identification were the same as for Example 14. From the sequencing results a clone containing a plasmid with the required [I201T,D253R]HCPB gene sequence was selected, and is known as pMC57.2.

Example 36

Cloning and Expression of [A248N,G251T,D253K]HCPB-(His)$_6$-c-Myc from E.coli

The method of cloning and expressing the [A248N, G251T,D253K]HCPB in E.coli was very similar to the method described in Reference Example 8. The gene for [A248N,G251T,D253K]HCPB was prepared as described in Example 2 but the starting material for PCR site directed mutagenesis was the [G251T,D253K]HCPB gene in plasmid pMC46.4 (described in Example 14) in place of pICI1712. However, in this case site directed mutagenesis was used during the PCR amplification of the gene to change the codon at amino acid position 248 in the mature gene from Alanine to Asparagine (GCT to AAC), the G248N change. Two PCR mixtures were prepared, in a manner similar to that described in Reference Examples 7 and 8. In the first reaction primers were 2264 (SEQ ID NO: 48) and 1024 (SEQ ID NO: 76, replacing SEQ ID NO: 61). In the second reaction primers were 6HIS9E10R1BS1 (SEQ ID NO: 42) and 1028 (SEQ ID NO: 77, replacing SEQ ID NO: 62). In both reactions the starting DNA was pMC46.4.

Methods of PCR, cloning, expression and identification were the same as for Example 14. From the sequencing results a clone containing a plasmid with the required [A248N,G251T,D253K]HCPB gene sequence was selected, and is known as pNC59.3.

Example 37

Cloning and Expression of [A248S,G251T,D253K]HCPB-(His)$_6$-c-Myc from E. coli

The method of cloning and expressing the [A248S, G251T,D253K]HCPB in E.coli was very similar to the method described in Reference Example 8. The gene for [A248S,G251T,D253K]HCPB was prepared as described in Example 2 but the starting material for PCR site directed mutagenesis was the [G251T,D253K]HCPB gene in plasmid pMC46.4 (described in Example 14) in place of pICI1712. However, in this case site directed mutagenesis was used during the PCR amplification of the gene to change the codon at amino acid position 248 in the mature gene from Alanine to Serine (GCT to TTC), the G248S change. Two PCR mixtures were prepared, in a manner similar to that described in Reference Examples 7 and 8. In the first reaction primers were 2264 (SEQ ID NO: 48) and 1024 (SEQ ID NO: 76, replacing SEQ ID NO: 61). In the second reaction primers were 6HIS9E10R1BS1 (SEQ ID NO: 42) and 1030 (SEQ ID NO: 78, replacing SEQ ID NO: 62). In both reactions the starting DNA was pMC46.4.

Methods of PCR, cloning, expression and identification were the same as for Example 14. From the sequencing results a clone containing a plasmid with the required [A248S,G251T,D253K]HCPB gene sequence was selected, and is known as pMC60.3.

Example 38

Preparation of Humanised A5B7 F(ab')$_2$-[G251T,D253K] HCPB Fusion Protein

The procedure described in Example 10 is repeated but with the sequence for D253K HCPB replaced by the sequence for [G251T,D253K]HCPB. The sequence for [G251T,D253K]HCPB is described in Example 14.

Example 39

Purification and Enzyme Activity of [A248S,G251T, D253K]HCPB-$(His)_6$-c-Myc

The procedure described in Example 3 was repeated with MSD 2230 replaced by MSD 2812 (HSD 1924 pZEN1921). Plasmid pZEN1921 is also known as pMC60.3. Preparation of plasmid pMC60.3 is described in Example 37. Two samples of cell paste were processed. separately. The weight of cell paste taken from storage was 593 g in the first sample and 558 g in the second sample. These were suspended in buffer A (750 ml and 710 ml respectively) to prepare an osmotic shockate. The volume of osmotic shockate, after dilution with buffer B, loaded onto two potator inhibitor columns in series was 31 for each sample. In the first purification, the fractions pooled from the two columns were 18 to 80 (column 1) and 30 to 63 (column 2). In the second purification, the fractions pooled from the two columns were 21 to 73 (column 1) and 23 to 68 (column 2). The combined purification provided 2.6 mg/ml of [A248S,G251T,D253K] HCPB at a purity of 83% in a volume of 4.4 ml.

Enzyme activity against Hipp-Glu, Hipp-Asp and Hipp-Arg substrates was determined as described in Example 17.

| Concentration ($\mu$g/ml) | Hipp-Glu | Hipp-Asp (% conversion) | Hipp-Arg |
|---|---|---|---|
| 25 | 93 | 5.5 | 0 |
| 0.25 | 14.5 | 0 | 0 |

Determination of Km and kcat against Hipp-Glu was as described in Example 7.

Km (mM) 1.1 kcat ($s^{-1}$)19 kcat/Km($mM^{-1}s^{-1}$)17.3

Example 40

Purification and Enzyme activity of [G251T,D253R]HCPB-(His)$_6$-c-Myc

The procedure described in Example 3 was repeated with MSD 2230 replaced by MSD 2803 (MSD 1924 pZEN1907). Plasmid pZEN1907 is also known as pMC55.2. Preparation of plasmid pMC55.2 is described in Example 34. Two samples of cell paste were processed separately. The weight of cell paste taken from storage was 660 g in the first sample and 484 g in the second sample. These were suspended in buffer A (800 ml and 700 ml respectively) to prepare an osmotic shockate. The volume of osmotic shockate, after dilution with buffer B, loaded onto two potator inhibitor columns in series was 1.61 and 1.41 respectively. In the first purification, the fractions pooled from the two columns were 20 to 70 (column 1) and 20 to 65 (column 2). In the second purification, a single fraction was collected from both columns corresponding to the elution peak profile given on the chart recorder. The combined purification provided 3.6 mg/ml of [G251T,D253R]HCPB at a purity of 50% in a volume of 1.4 ml.

Enzyme activity against Hipp-Glu, Hipp-Asp and Hipp-Arg substrates was determined as described in Example 17.

| Concentration (μg/ml) | Hipp-Glu | Hipp-Asp (% conversion) | Hipp-Arg |
|---|---|---|---|
| 25 | 96 | 29 | 0 |
| 1 | 16.2 | 1.2 | 0 |

Determination of Km and kcat against Hipp-Glu and Hipp-Asp was as described in Example 7.

|  | Hipp-Glu | Hipp-Asp |
|---|---|---|
| Km (mM) | 1.6 | 1.7 |
| kcat (s$^{-1}$) | 7.8 | 0.7 |
| kcat/Km (mM$^{-1}$s$^{-1}$) | 4.9 | 0.4 |

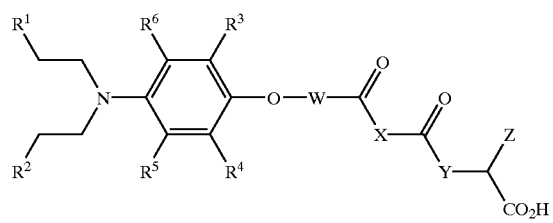

Formula 1

Formula 2

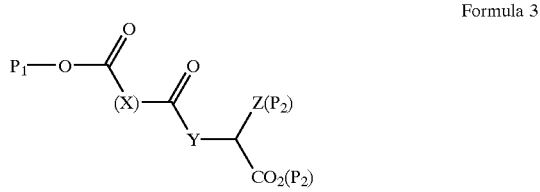

Formula 3

Formula 4

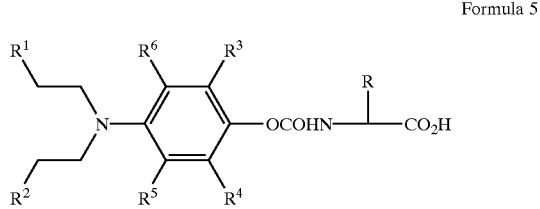

Formula 5

---

What is claimed is:

1. A conjugate which is substantially non-immunogenic in humans comprising a targeting moiety capable of binding with a tumour associated antigen, the targeting moiety being linked to a mutated form of a carboxypeptidase B (CPB) enzyme capable of converting a prodrug into an antineoplastic drug wherein the prodrug is not significantly convertible into the antineoplastic drug in humans by the natural unmutated enzyme, wherein the mutated form is a pancreatic human CPB enzyme having at least one amino acid substitution at an amino acid position selected from the group consisting of 54, 145, 201, 205, 245, 248, 251, 253 and 288 wherein said amino acid positions correspond to the amino acid sequence set forth in SEQ ID NO:39 from position 109 through position 415 inclusive, renumbered as 1 to 307.

2. A conjugate according to claim 1 in which the targeting moiety is an antibody.

3. A conjugate according to claim 2 in which the antibody is a F(ab')₂ antibody fragment.

4. A conjugate according to any one of claims 1–3 in which the enzyme is mutated to comprise a polarity change in its active site such that it can turn over a prodrug with a complementary polarity.

5. A conjugate according to claim 4 in which the enzyme is any one of the following pancreatic human CPB mutants: D253K; D253R; [G251N,D253K]; [G251T,D253K]; [G251S,D253K]; [G251T,D253R,]; [A248S,G251T,D253K]; [A248N,G251N,D253K]; [A248S,G251N,D253K]; and [S205N,G251N,D253K].

6. A conjugate according to any one of claims 1–3 in which the pancreatic human CPB enzyme has natural amino acid Asp 253 substituted by Arg, Asn, Gln or Lys.

7. A conjugate according to any one of claims 1–3 in which the pancreatic human CPB enzyme has natural amino acid Asp 253 substituted by Arg or Lys and natural amino acid Gly 251 substituted by Thr, Asn, Ser, Gln, Lys or Val.

8. A conjugate according to any one of claims 1–3 in which the pancreatic human CPB enzyme has natural amino acid Asp 253 substituted by Arg or Lys and natural amino acid Gly 251 substituted by Thr, Asn or Ser.

9. A conjugate according to any one of claims 1–3 in which the enzyme is any one of the following pancreatic human CPB mutants:
pancreatic human CPB having natural amino acid Asp 253 substituted by Asn, Gln or Lys; in combination with any one or more amino acid substitutions selected from:
natural amino acid Gln 54 substituted by Arg, Lys or Asn;
natural amino acid Asp 145 substituted by Val, Leu, Ile or Ala;
natural amino acid Ile 201 substituted by Ser or Thr;
natural amino acid Ser 205 substituted by Asn, Gln, His, Lys or Arg;
natural amino acid Ile 245 substituted by Ser, Thr, Ala, Val, Leu, Asn, Gln, Lys, Arg or His;
natural amino acid Ala 248 substituted by Gln, Lys, Arg, His, Ser or Thr;
natural amino acid Gly 251 substituted by Thr, Asn, Ser, Gln, His, Lys, Arg, Val, Ile, Leu, Met, Phe, Ala or Norleucine; and
natural amino acid Cys 288 substituted by Ser, Thr, Ala, Val, Leu or Ile.

10. A conjugate according to any one of claims 1–3 in which the enzyme is any one of the following pancreatic human CPB mutants:
pancreatic human CPB having natural amino acid Asp 253 substituted by Arg or Lys and natural amino acid Gly 251 substituted by Thr, Asn, Ser, Gln, Lys or Val; in combination with any one or more amino acid substitutions selected from:
natural amino acid Gln 54 substituted by Arg;
natural amino acid Asp 145 substituted by Ala;
natural amino acid Ile 201 substituted by Ser;
natural amino acid Ser 205 substituted by Asn;
natural amino acid Ile 245 substituted by Ser, Ala or His;
natural amino acid Ala 248 substituted by His, Ser or Asn; and
natural amino acid Cys 288 substituted by Ser or Ala.

11. A conjugate according to any one of claims 1–3 in which the enzyme is any one of the following pancreatic human CPB mutants:
pancreatic human CPB having natural amino acid Asp 253 substituted by any one of Arg or Lys and natural amino acid Gly 251 substituted by any one of Thr, Asn or Ser; in combination with any one or more amino acid substitutions selected from:
natural amino acid Gln 54 substituted by Arg;
natural amino acid Asp 145 substituted by Ala;
natural amino acid Ile 201 substituted by Ser;
natural amino acid Ser 205 substituted by Asn;
natural amino acid Ile 245 substituted by Ala;
natural amino acid Ala 248 substituted by any one of Ser or Asn; and
natural amino acid Cys 288 substituted by Ser.

12. A mutant CPB enzyme as defined in claim 1.

13. A polynucleotide sequence capable of encoding a mutant CPB enzyme defined in claim 12.

14. A vector comprising a polynucleotide sequence defined in claim 13.

15. A host cell comprising a polynucleotide sequence defined in claim 13.

16. A method of making a mutant CPB enzyme which comprises expressing the enzyme from a host cell as defined in claim 15 and at least partially purifying the enzyme.

17. A pharmaceutical composition comprising a targeting moiety capable of binding with a tumour associated antigen, the targeting moiety being linked to a mutated form of a pancreatic human carboxypeptidase B (CPB) enzyme having at least one amino acid substitution at an amino acid position selected from the group consisting of 54, 145, 201, 205, 245, 248, 251, 253 and 288 wherein said positions correspond to the amino acid sequence set forth in SEQ ID NO:39 from position 109 through position 415 inclusive, renumbered as 1 to 307; and a pharmaceutically acceptable carrier or diluent.

18. A method of making a conjugate which comprises linking a targeting moiety capable of binding with a tumour associated antigen and a mutated form of a pancreatic human carboxypeptidase B (CPB) enzyme having at least one amino acid substitution at an amino acid position selected from the group consisting of 54, 145, 201, 205, 245, 248, 251, 253 and 288 wherein said positions correspond to the amino acid sequence set forth in SEQ ID NO:39 from position 109 through position 415 inclusive, renumbered as 1 to 307.

* * * * *

SEQUENCE LISTING (1) GENERAL INFORMATION:

(iii) NUMBER OF SEQUENCES: 87

(2) INFORMATION FOR SEQ ID NO: 1:

(i) SEQUENCE CHARACTERISTICS:
      (A) LENGTH: 41 base pairs
      (B) TYPE: nucleic acid
      (C) STRANDEDNESS: single
      (D) TOPOLOGY: linear (ii) MOLECULE TYPE: other nucleic acid (xi) SEQUENCE DESCRIPTION: SEQ ID NO: 1:

```
CTCTAGGAAT TCTTATTAGT ACAGGTGTTC CAGGACGTAG C                      41
```

(2) INFORMATION FOR SEQ ID NO: 2:

(i) SEQUENCE CHARACTERISTICS:
        (A) LENGTH: 108 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 2:

```
CCCAAGCTTG CCGCCACCAT GTTGGCAGTC TTGGTTCTGG TGACTGTGGC CCTGGCATCT   60

GCTGCAACAG GACACAGTTA TGAGAAGTAC AACAAGTGGG AAACGATA              108
```

(2) INFORMATION FOR SEQ ID NO: 3:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 3:

```
AACAGCTATG ACCATG                                                  16
```

(2) INFORMATION FOR SEQ ID NO: 4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 4:

```
GTAAAACGAC GGCCAGT                                                 17
```

(2) INFORMATION FOR SEQ ID NO: 5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 5:

```
TCGCTATTAC CATGGTGATG CGGTTTTGGC                                   30
```

(2) INFORMATION FOR SEQ ID NO: 6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 6:

```
CAGACTCTGC AGCAGGTCCA CAG                                          23
```

(2) INFORMATION FOR SEQ ID NO: 7:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 7:

```
CCCAAGCTTG CCGCCACCAT GTTGGCACTC TTGGTTCTGG TGACTGTGGC CCTG        54
```

(2) INFORMATION FOR SEQ ID NO: 8:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 8:

```
CTCATAACTG AATTCTTATT AACGAACCCG GCTATCAAA                         39
```

(2) INFORMATION FOR SEQ ID NO: 9:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 9:

```
GGATCTGCTG CCCAAGCTTA CTCCATGGTG ACCC                              34
```

(2) INFORMATION FOR SEQ ID NO: 10:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 10:

```
CTTCTCATAA CTGTGTCCTG TTGCGAACAC GCTGCTCACC TCGGGCACTG TACATATGCA  60

AGGCTTACAA CCACAATCCC                                             80
```

(2) INFORMATION FOR SEQ ID NO: 11:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 11:

```
GGTTGTAAGC CTTGCATATG TACAGTGCCC GAGGTGAGCA GCGTGTTCGC AACAGGACAC  60

AGTTATGAGA AGTACAAC                                               78
```

(2) INFORMATION FOR SEQ ID NO: 12:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 12:

CCGTTTGATC TCGAGCTTGG TGCCTCC                             27

(2) INFORMATION FOR SEQ ID NO: 13:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 13:

ATATAAAGCT TGCCGCCACC ATGAAGTTGT GGCTGAACTG GATTTTCCTT        50

(2) INFORMATION FOR SEQ ID NO: 14:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 14:

ATCGAATTCG CCGCCACCAT GGATTTTCAA GTGCAGATTT TCAGCTTC          48

(2) INFORMATION FOR SEQ ID NO: 15:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 15:

TGAGAATTCT TACTATGTAC ATATGCAAGG CTTACAACCA CAATC             45

(2) INFORMATION FOR SEQ ID NO: 16:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 16:

GCGCCGAATT CTTATTAACA CTCATTCCTG TTGAA                       35

(2) INFORMATION FOR SEQ ID NO: 17:

(i) SEQUENCE CHARACTERISTICS:

(A) LENGTH: 30 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 17:

GACCTGGAAC TCTGGATCTC TGTCCAGCGG                                    30

(2) INFORMATION FOR SEQ ID NO: 18:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 18:

AGGTGTGCAC ACCGCTGGAC AGAGATCCAG                                    30

(2) INFORMATION FOR SEQ ID NO: 19:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 19:

TGGTACCAGC AGAAGCCAGG TTCCTCCCCC                                    30

(2) INFORMATION FOR SEQ ID NO: 20:

(i) SEQUENCE CHARACTERISTICS:
        (A) LENGTH: 777 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: CDS
        (B) LOCATION:16..765

(xi) SEQUENCE DESCRIPTION: SEQ ID NO: 20:

AAGCTTGCCG CCACC ATG AAG TTG TGG CTG AAC TGG ATT TTC CTT GTA ACA     51
                Met Lys Leu Trp Leu Asn Trp Ile Phe Leu Val Thr
                 1               5                  10

CTT TTA AAT GGT ATC CAG TGT GAG GTG AAG CTG GTG GAG TCT GGA GGA      99
Leu Leu Asn Gly Ile Gln Cys Glu Val Lys Leu Val Glu Ser Gly Gly
            15                  20                  25

GGC TTG GTA CAG CCT GGG GGT TCT CTG AGA CTC TCC TGT GCA ACT TCT     147
Gly Leu Val Gln Pro Gly Gly Ser Leu Arg Leu Ser Cys Ala Thr Ser
        30                  35                  40

GGG TTC ACC TTC ACT GAT TAC TAC ATG AAC TGG GTC CGC CAG CCT CCA     195
Gly Phe Thr Phe Thr Asp Tyr Tyr Met Asn Trp Val Arg Gln Pro Pro
45                  50                  55                  60

GGA AAG GCA CTT GAG TGG TTG GGT TTT ATT GGA AAC AAA GCT AAT GGT     243
Gly Lys Ala Leu Glu Trp Leu Gly Phe Ile Gly Asn Lys Ala Asn Gly
                65                  70                  75

TAC ACA ACA GAG TAC AGT GCA TCT GTG AAG GGT CGG TTC ACC ATC TCC     291

```
Tyr Thr Thr Glu Tyr Ser Ala Ser Val Lys Gly Arg Phe Thr Ile Ser
             80                  85                  90

AGA GAC AAA TCC CAA AGC ATC CTC TAT CTT CAA ATG AAC ACC CTG AGA      339
Arg Asp Lys Ser Gln Ser Ile Leu Tyr Leu Gln Met Asn Thr Leu Arg
         95                 100                 105

GCT GAG GAC AGT GCC ACT TAT TAC TGT ACA AGA GAT AGG GGG CTA CGG      387
Ala Glu Asp Ser Ala Thr Tyr Tyr Cys Thr Arg Asp Arg Gly Leu Arg
    110                 115                 120

TTC TAC TTT GAC TAC TGG GGC CAA GGC ACC ACT CTC ACA GTC TCC TCA      435
Phe Tyr Phe Asp Tyr Trp Gly Gln Gly Thr Thr Leu Thr Val Ser Ser
125                 130                 135                 140

GCC AAA ACG ACA CCC CCA TCT GTC TAT CCA CTG GCC CCT GGA TCT GCT      483
Ala Lys Thr Thr Pro Pro Ser Val Tyr Pro Leu Ala Pro Gly Ser Ala
                145                 150                 155

GCC CAA ACT AAC TCC ATG GTG ACC CTG GGA TGC CTG GTC AAG GGC TAT      531
Ala Gln Thr Asn Ser Met Val Thr Leu Gly Cys Leu Val Lys Gly Tyr
            160                 165                 170

TTC CCT GAG CCA GTG ACA GTG ACC TGG AAC TCT GGA TCT CTG TCC AGC      579
Phe Pro Glu Pro Val Thr Val Thr Trp Asn Ser Gly Ser Leu Ser Ser
        175                 180                 185

GGT GTG CAC ACC TTC CCA GCT GTC CTG CAG TCT GAC CTC TAC ACT CTG      627
Gly Val His Thr Phe Pro Ala Val Leu Gln Ser Asp Leu Tyr Thr Leu
    190                 195                 200

AGC AGC TCA GTG ACT GTC CCC TCC AGC ACC TGG CCC AGC GAG ACC GTC      675
Ser Ser Ser Val Thr Val Pro Ser Ser Thr Trp Pro Ser Glu Thr Val
205                 210                 215                 220

ACC TGC AAC GTT GCC CAC CCG GCC AGC AGC ACC AAG GTG GAC AAG AAA      723
Thr Cys Asn Val Ala His Pro Ala Ser Ser Thr Lys Val Asp Lys Lys
                225                 230                 235

ATT GTG CCC AGG GAT TGT GGT TGT AAG CCT TGC ATA TGT ACA              765
Ile Val Pro Arg Asp Cys Gly Cys Lys Pro Cys Ile Cys Thr
            240                 245                 250

TAGTAAGAAT TC                                                        777
```

(2) INFORMATION FOR SEQ ID NO: 21:

(i) SEQUENCE CHARACTERISTICS:
        (A) LENGTH: 250 amino acids
        (B) TYPE: amino acid
        (D) TOPOLOGY: linear (ii) MOLECULE TYPE: protein (xi) SEQUENCE DESCRIPTION: SEQ ID NO: 21:

```
Met Lys Leu Trp Leu Asn Trp Ile Phe Leu Val Thr Leu Leu Asn Gly
  1               5                  10                  15

Ile Gln Cys Glu Val Lys Leu Val Glu Ser Gly Gly Gly Leu Val Gln
             20                  25                  30

Pro Gly Gly Ser Leu Arg Leu Ser Cys Ala Thr Ser Gly Phe Thr Phe
         35                  40                  45

Thr Asp Tyr Tyr Met Asn Trp Val Arg Gln Pro Pro Gly Lys Ala Leu
     50                  55                  60

Glu Trp Leu Gly Phe Ile Gly Asn Lys Ala Asn Gly Tyr Thr Thr Glu
 65                  70                  75                  80

Tyr Ser Ala Ser Val Lys Gly Arg Phe Thr Ile Ser Arg Asp Lys Ser
             85                  90                  95

Gln Ser Ile Leu Tyr Leu Gln Met Asn Thr Leu Arg Ala Glu Asp Ser
            100                 105                 110

Ala Thr Tyr Tyr Cys Thr Arg Asp Arg Gly Leu Arg Phe Tyr Phe Asp
```

```
                115                 120                  125
Tyr Trp Gly Gln Gly Thr Thr Leu Thr Val Ser Ser Ala Lys Thr Thr
    130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Val Thr Val Thr Trp Asn Ser Gly Ser Leu Ser Ser Gly Val His Thr
                180                 185                 190

Phe Pro Ala Val Leu Gln Ser Asp Leu Tyr Thr Leu Ser Ser Ser Val
        195                 200                 205

Thr Val Pro Ser Ser Thr Trp Pro Ser Glu Thr Val Thr Cys Asn Val
    210                 215                 220

Ala His Pro Ala Ser Ser Thr Lys Val Asp Lys Lys Ile Val Pro Arg
225                 230                 235                 240

Asp Cys Gly Cys Lys Pro Cys Ile Cys Thr
                245                 250

(2) INFORMATION FOR SEQ ID NO: 22:

(i) SEQUENCE CHARACTERISTICS:
        (A) LENGTH: 732 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: CDS
        (B) LOCATION:16..720

(xi) SEQUENCE DESCRIPTION: SEQ ID NO: 22:

GAATTCGCCG CCACC ATG GAT TTT CAA GTG CAG ATT TTC AGC TTC CTG CTA        51
               Met Asp Phe Gln Val Gln Ile Phe Ser Phe Leu Leu
                 1               5                  10

ATC AGT GCT TCA GTC ATA ATG TCC AGA GGA CAA ACT GTT CTC TCC CAG         99
Ile Ser Ala Ser Val Ile Met Ser Arg Gly Gln Thr Val Leu Ser Gln
            15                  20                  25

TCT CCA GCA ATC CTG TCT GCA TCT CCA GGG GAG AAG GTC ACA ATG ACT        147
Ser Pro Ala Ile Leu Ser Ala Ser Pro Gly Glu Lys Val Thr Met Thr
    30                  35                  40

TGC AGG GCC AGC TCA AGT GTA ACT TAC ATT CAC TGG TAC CAG CAG AAG        195
Cys Arg Ala Ser Ser Ser Val Thr Tyr Ile His Trp Tyr Gln Gln Lys
45                  50                  55                  60

CCA GGT TCC TCC CCC AAA TCC TGG ATT TAT GCC ACA TCC AAC CTG GCT        243
Pro Gly Ser Ser Pro Lys Ser Trp Ile Tyr Ala Thr Ser Asn Leu Ala
                65                  70                  75

TCT GGA GTC CCT GCT CGC TTC AGT GGC AGT GGG TCT GGG ACC TCT TAC        291
Ser Gly Val Pro Ala Arg Phe Ser Gly Ser Gly Ser Gly Thr Ser Tyr
            80                  85                  90

TCT CTC ACA ATC AGC AGA GTG GAG GCT GAA GAT GCT GCC ACT TAT TAC        339
Ser Leu Thr Ile Ser Arg Val Glu Ala Glu Asp Ala Ala Thr Tyr Tyr
        95                  100                 105

TGC CAA CAT TGG AGT AGT AAA CCA CCG ACG TTC GGT GGA GGC ACC AAG        387
Cys Gln His Trp Ser Ser Lys Pro Pro Thr Phe Gly Gly Gly Thr Lys
    110                 115                 120

CTG GAA ATC AAA CGG GCT GAT GCT GCA CCA ACT GTA TCC ATC TTC CCA        435
Leu Glu Ile Lys Arg Ala Asp Ala Ala Pro Thr Val Ser Ile Phe Pro
125                 130                 135                 140
```

```
CCA TCC AGT GAG CAG TTA ACA TCT GGA GGT GCC TCA GTC GTG TGC TTC        483
Pro Ser Ser Glu Gln Leu Thr Ser Gly Gly Ala Ser Val Val Cys Phe
            145                 150                 155

TTG AAC AAC TTC TAC CCC AAA GAC ATC AAT GTC AAG TGG AAG ATT GAT        531
Leu Asn Asn Phe Tyr Pro Lys Asp Ile Asn Val Lys Trp Lys Ile Asp
                160                 165                 170

GGC AGT GAA CGA CAA AAT GGC GTC CTG AAC AGT TGG ACT GAT CAG GAC        579
Gly Ser Glu Arg Gln Asn Gly Val Leu Asn Ser Trp Thr Asp Gln Asp
                175                 180                 185

AGC AAA GAC AGC ACC TAC AGC ATG AGC AGC ACC CTC ACG TTG ACC AAG        627
Ser Lys Asp Ser Thr Tyr Ser Met Ser Ser Thr Leu Thr Leu Thr Lys
        190                 195                 200

GAC GAG TAT GAA CGA CAT AAC AGC TAT ACC TGT GAG GCC ACT CAC AAG        675
Asp Glu Tyr Glu Arg His Asn Ser Tyr Thr Cys Glu Ala Thr His Lys
205                 210                 215                 220

ACA TCA ACT TCA CCC ATT GTC AAG AGC TTC AAC AGG AAT GAG TGT            720
Thr Ser Thr Ser Pro Ile Val Lys Ser Phe Asn Arg Asn Glu Cys
                225                 230                 235

TAATAAGAAT TC                                                          732

(2) INFORMATION FOR SEQ ID NO: 23:

(i) SEQUENCE CHARACTERISTICS:
        (A) LENGTH: 235 amino acids
        (B) TYPE: amino acid
        (D) TOPOLOGY: linear (ii) MOLECULE TYPE: protein (xi) SEQUENCE DESCRIPTION: SEQ ID NO: 23:

Met Asp Phe Gln Val Gln Ile Phe Ser Phe Leu Leu Ile Ser Ala Ser
 1               5                  10                  15

Val Ile Met Ser Arg Gly Gln Thr Val Leu Ser Gln Ser Pro Ala Ile
                20                  25                  30

Leu Ser Ala Ser Pro Gly Glu Lys Val Thr Met Thr Cys Arg Ala Ser
            35                  40                  45

Ser Ser Val Thr Tyr Ile His Trp Tyr Gln Gln Lys Pro Gly Ser Ser
        50                  55                  60

Pro Lys Ser Trp Ile Tyr Ala Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln His Trp
            100                 105                 110

Ser Ser Lys Pro Pro Thr Phe Gly Gly Gly Thr Lys Leu Glu Ile Lys
        115                 120                 125

Arg Ala Asp Ala Ala Pro Thr Val Ser Ile Phe Pro Pro Ser Ser Glu
130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
        195                 200                 205

Arg His Asn Ser Tyr Thr Cys Glu Ala Thr His Lys Thr Ser Thr Ser
    210                 215                 220
```

```
Pro Ile Val Lys Ser Phe Asn Arg Asn Glu Cys
225             230             235
```

(2) INFORMATION FOR SEQ ID NO: 24:

(i) SEQUENCE CHARACTERISTICS:
        (A) LENGTH: 777 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: CDS
        (B) LOCATION:16..765

(xi) SEQUENCE DESCRIPTION: SEQ ID NO: 24:

```
AAGCTTGCCG CCACC ATG AAG TTG TGG CTG AAC TGG ATT TTC CTT GTA ACA        51
                Met Lys Leu Trp Leu Asn Trp Ile Phe Leu Val Thr
                 1               5                  10

CTT TTA AAT GGT ATC CAG TGT GAG GTG CAG CTG CTG GAG TCT GGA GGA        99
Leu Leu Asn Gly Ile Gln Cys Glu Val Gln Leu Leu Glu Ser Gly Gly
             15                  20                  25

GGA CTG GTG CAG CCT GGA GGA TCT CTG AGA CTG TCT TGT GCA ACA TCT       147
Gly Leu Val Gln Pro Gly Gly Ser Leu Arg Leu Ser Cys Ala Thr Ser
         30                  35                  40

GGA TTC ACC TTC ACA GAC TAC TAC ATG AAT TGG GTG AGA CAG GCA CCT       195
Gly Phe Thr Phe Thr Asp Tyr Tyr Met Asn Trp Val Arg Gln Ala Pro
     45                  50                  55                  60

GGA AAG GGA CTC GAG TGG CTG GGC TTC ATC GGA AAT AAG GCA AAT GGA       243
Gly Lys Gly Leu Glu Trp Leu Gly Phe Ile Gly Asn Lys Ala Asn Gly
                 65                  70                  75

TAC ACA ACA GAG TAC TCT GCA TCT GTG AAG GGA AGA TTC ACA ATT TCC       291
Tyr Thr Thr Glu Tyr Ser Ala Ser Val Lys Gly Arg Phe Thr Ile Ser
             80                  85                  90

AGA GAC AAG AGC AAG TCC ACA CTG TAC CTG CAG ATG AAT ACA CTG CAG       339
Arg Asp Lys Ser Lys Ser Thr Leu Tyr Leu Gln Met Asn Thr Leu Gln
         95                 100                 105

GCA GAG GAC TCT GCA ATT TAC TAC TGT ACA AGA GAC AGA GGA CTG AGA       387
Ala Glu Asp Ser Ala Ile Tyr Tyr Cys Thr Arg Asp Arg Gly Leu Arg
    110                 115                 120

TTC TAC TTC GAC TAC TGG GGA CAG GGA ACA CTG GTG ACA GTG TCT TCT       435
Phe Tyr Phe Asp Tyr Trp Gly Gln Gly Thr Leu Val Thr Val Ser Ser
125                 130                 135                 140

GCT AGC ACC AAG GGA CCA TCG GTC TTC CCC CTG GCC CCC TGC TCC AGG       483
Ala Ser Thr Lys Gly Pro Ser Val Phe Pro Leu Ala Pro Cys Ser Arg
                145                 150                 155

AGC ACC TCC GAG AGC ACA GCC GCC CTG GGC TGC CTG GTC AAG GAC TAT       531
Ser Thr Ser Glu Ser Thr Ala Ala Leu Gly Cys Leu Val Lys Asp Tyr
            160                 165                 170

TTC CCC GAA CCG GTG ACG GTG TCG TGG AAC TCA GGC GCT CTG ACC AGC       579
Phe Pro Glu Pro Val Thr Val Ser Trp Asn Ser Gly Ala Leu Thr Ser
        175                 180                 185

GGC GTG CAC ACC TTC CCG GCT GTC CTA CAG TCC TCA GGA CTC TAC TCC       627
Gly Val His Thr Phe Pro Ala Val Leu Gln Ser Ser Gly Leu Tyr Ser
    190                 195                 200

CTC AGC AGC GTC GTG ACG GTG CCC TCC AGC AAC TTC GGC ACC CAG ACC       675
Leu Ser Ser Val Val Thr Val Pro Ser Ser Asn Phe Gly Thr Gln Thr
205                 210                 215                 220

TAC ACC TGC AAC GTA GAT CAC AAG CCC AGC AAC ACC AAG GTG GAC AAG       723
Tyr Thr Cys Asn Val Asp His Lys Pro Ser Asn Thr Lys Val Asp Lys
```

```
                    225                 230                 235
ACA GTT GAG CGC AAA TGT TGT GTC GAG TGC CCA CCG TGC CCG                      765
Thr Val Glu Arg Lys Cys Cys Val Glu Cys Pro Pro Cys Pro
                    240                 245                 250

TAATAGGAAT TC                                                                777
```

(2) INFORMATION FOR SEQ ID NO: 25:

(i) SEQUENCE CHARACTERISTICS:
        (A) LENGTH: 250 amino acids
        (B) TYPE: amino acid
        (D) TOPOLOGY: linear (ii) MOLECULE TYPE: protein (xi) SEQUENCE DESCRIPTION: SEQ ID NO: 25:

```
Met Lys Leu Trp Leu Asn Trp Ile Phe Leu Val Thr Leu Leu Asn Gly
 1               5                  10                  15

Ile Gln Cys Glu Val Gln Leu Leu Glu Ser Gly Gly Gly Leu Val Gln
                20                  25                  30

Pro Gly Gly Ser Leu Arg Leu Ser Cys Ala Thr Ser Gly Phe Thr Phe
            35                  40                  45

Thr Asp Tyr Tyr Met Asn Trp Val Arg Gln Ala Pro Gly Lys Gly Leu
        50                  55                  60

Glu Trp Leu Gly Phe Ile Gly Asn Lys Ala Asn Gly Tyr Thr Thr Glu
65                  70                  75                  80

Tyr Ser Ala Ser Val Lys Gly Arg Phe Thr Ile Ser Arg Asp Lys Ser
                85                  90                  95

Lys Ser Thr Leu Tyr Leu Gln Met Asn Thr Leu Gln Ala Glu Asp Ser
            100                 105                 110

Ala Ile Tyr Tyr Cys Thr Arg Asp Arg Gly Leu Arg Phe Tyr Phe Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro
                245                 250
```

(2) INFORMATION FOR SEQ ID NO: 26:

(i) SEQUENCE CHARACTERISTICS:
        (A) LENGTH: 732 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: CDS
        (B) LOCATION:16..720

(xi) SEQUENCE DESCRIPTION: SEQ ID NO: 26:

```
GAATTCGCCG CCACC ATG GAT TTT CAA GTG CAG ATT TTC AGC TTC CTG CTA        51
              Met Asp Phe Gln Val Gln Ile Phe Ser Phe Leu Leu
                1               5                      10

ATC AGT GCT TCA GTC ATA ATG TCC AGA GGA CAG ACT GTA CTC ACT CAG         99
Ile Ser Ala Ser Val Ile Met Ser Arg Gly Gln Thr Val Leu Thr Gln
            15                  20                  25

AGT CCA AGT AGT CTC AGT GTA AGT GTA GGT GAT AGG GTA ACT ATG ACT        147
Ser Pro Ser Ser Leu Ser Val Ser Val Gly Asp Arg Val Thr Met Thr
        30                  35                  40

TGT AGG GCC AGT AGT AGT GTA ACT TAT ATC CAT TGG TAT CAG CAG AAA        195
Cys Arg Ala Ser Ser Ser Val Thr Tyr Ile His Trp Tyr Gln Gln Lys
45                  50                  55                  60

CCA GGT CTC GCC CCA AAA AGT TGG ATC TAT GCC ACT AGT AAC CTC GCC        243
Pro Gly Leu Ala Pro Lys Ser Trp Ile Tyr Ala Thr Ser Asn Leu Ala
                65                  70                  75

AGT GGT GTA CCA TCT AGA TTC AGT GGT AGC GGT AGT GGT ACT GAT TAT        291
Ser Gly Val Pro Ser Arg Phe Ser Gly Ser Gly Ser Gly Thr Asp Tyr
            80                  85                  90

ACT CTC ACT ATC AGT AGT CTC CAG CCA GAA GAT ATC GCC ACT TAC TAT        339
Thr Leu Thr Ile Ser Ser Leu Gln Pro Glu Asp Ile Ala Thr Tyr Tyr
        95                 100                 105

TGC CAG CAT TGG AGT AGT AAA CCA CCA ACT TTC GGT CAG GGT ACT AAA        387
Cys Gln His Trp Ser Ser Lys Pro Pro Thr Phe Gly Gln Gly Thr Lys
    110                 115                 120

GTA GAA GTA AAA CGT ACT GTG GCT GCA CCA TCT GTC TTC ATC TTC CCG        435
Val Glu Val Lys Arg Thr Val Ala Ala Pro Ser Val Phe Ile Phe Pro
125                 130                 135                 140

CCA TCT GAT GAG CAG TTG AAA TCT GGA ACT GCC TCT GTT GTG TGC CTG        483
Pro Ser Asp Glu Gln Leu Lys Ser Gly Thr Ala Ser Val Val Cys Leu
                145                 150                 155

CTG AAT AAC TTC TAT CCC AGA GAG GCC AAA GTA CAG TGG AAG GTG GAT        531
Leu Asn Asn Phe Tyr Pro Arg Glu Ala Lys Val Gln Trp Lys Val Asp
            160                 165                 170

AAC GCC CTC CAA TCG GGT AAC TCC CAG GAG AGT GTC ACA GAG CAG GAC        579
Asn Ala Leu Gln Ser Gly Asn Ser Gln Glu Ser Val Thr Glu Gln Asp
        175                 180                 185

AGC AAG GAC AGC ACC TAC AGC CTC AGC AGC ACC CTG ACG CTG AGC AAA        627
Ser Lys Asp Ser Thr Tyr Ser Leu Ser Ser Thr Leu Thr Leu Ser Lys
    190                 195                 200

GCA GAC TAC GAG AAA CAC AAA GTC TAC GCC TGC GAA GTC ACC CAT CAG        675
Ala Asp Tyr Glu Lys His Lys Val Tyr Ala Cys Glu Val Thr His Gln
205                 210                 215                 220

GGC CTG AGT TCG CCC GTC ACA AAG AGC TTC AAC AGG GGA GAG TGT            720
Gly Leu Ser Ser Pro Val Thr Lys Ser Phe Asn Arg Gly Glu Cys
                225                 230                 235

TAATAGGAAT TC                                                          732
```

(2) INFORMATION FOR SEQ ID NO: 27:

(i) SEQUENCE CHARACTERISTICS:
        (A) LENGTH: 235 amino acids
        (B) TYPE: amino acid
        (D) TOPOLOGY: linear (ii) MOLECULE TYPE: protein (xi) SEQUENCE DESCRIPTION: SEQ ID NO: 27:

```
Met Asp Phe Gln Val Gln Ile Phe Ser Phe Leu Leu Ile Ser Ala Ser
 1               5                  10                  15

Val Ile Met Ser Arg Gly Gln Thr Val Leu Thr Gln Ser Pro Ser Ser
            20                  25                  30

Leu Ser Val Ser Val Gly Asp Arg Val Thr Met Thr Cys Arg Ala Ser
        35                  40                  45

Ser Ser Val Thr Tyr Ile His Trp Tyr Gln Gln Lys Pro Gly Leu Ala
    50                  55                  60

Pro Lys Ser Trp Ile Tyr Ala Thr Ser Asn Leu Ala Ser Gly Val Pro
65                  70                  75                  80

Ser Arg Phe Ser Gly Ser Gly Ser Gly Thr Asp Tyr Thr Leu Thr Ile
                85                  90                  95

Ser Ser Leu Gln Pro Glu Asp Ile Ala Thr Tyr Tyr Cys Gln His Trp
            100                 105                 110

Ser Ser Lys Pro Pro Thr Phe Gly Gln Gly Thr Lys Val Glu Val Lys
        115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
210                 215                 220

Pro Val Thr Lys Ser Phe Asn Arg Gly Glu Cys
225                 230                 235
```

(2) INFORMATION FOR SEQ ID NO: 28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 28:

GTTGGAGCTC TTGGTTCTGG                                             20

(2) INFORMATION FOR SEQ ID NO: 29:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 29:

CAAGGCCTCG AGCTTTCTCA AC                                          22

(2) INFORMATION FOR SEQ ID NO: 30:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: other nucleic acid (xi) SEQUENCE DESCRIPTION: SEQ ID NO: 30:

GTTTGATTCT AGAGTTCGTG C                                            21

(2) INFORMATION FOR SEQ ID NO: 31:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 31:

TTGTAAAACG ACGGCCAGTG AG                                           22

(2) INFORMATION FOR SEQ ID NO: 32:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 32:

GAAACAGCTA TGACCATGAT TACG                                         24

(2) INFORMATION FOR SEQ ID NO: 33:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 33:

CAGACTCTGC AGCAGGTCCA CAG                                          23

(2) INFORMATION FOR SEQ ID NO: 34:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 34:

GGACCTGCTG CAGAGTCTG                                               19

(2) INFORMATION FOR SEQ ID NO: 35:

(i) SEQUENCE CHARACTERISTICS:
        (A) LENGTH: 21 base pairs
        (B) TYPE: nucleic acid
        (C) STRANDEDNESS: single (D) TOPOLOGY: linear (ii) MOLECULE TYPE: other nucleic acid (xi) SEQUENCE DESCRIPTION: SEQ ID NO: 35:

GCCTGTGCTC AATATTGATG G                                            21

(2) INFORMATION FOR SEQ ID NO: 36:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO: 36:

CCGTGTTAAA GCAGAAGATA CTG                                          23

(2) INFORMATION FOR SEQ ID NO: 37:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO: 37:

GCTACTGTGA AGAACTTGC CTC                                           23

(2) INFORMATION FOR SEQ ID NO: 38:

(i) SEQUENCE CHARACTERISTICS:
            (A) LENGTH: 1263 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO: 38:

GAGCTCTTGG TTCTGGTGAC TGTGGCCCTG GCATCTGCTC ATCATGGTGG TGAGCACTTT    60

GAAGGCGAGA AGGTGTTCCG TGTTAACGTT GAAGATGAAA ATCACATTAA CATAATCCGC   120

GAGTTGGCCA GCACGACCCA GATTGACTTC TGGAAGCCAG ATTCTGTCAC ACAAATCAAA   180

CCTCACAGTA CAGTTGACTT CCGTGTTAAA GCAGAAGATA CTGTCACTGT GGAGAATGTT   240

CTAAAGCAGA ATGAACTACA ATACAAGGTA CTGATAAGCA ACCTGAGAAA TGTGGTGGAG   300

GCTCAGTTTG ATAGCCGGGT TCGTGCAACA GGACACAGTT ATGAGAAGTA CAACAAGTGG   360

GAAACGATAG AGGCTTGGAC TCAACAAGTC GCCACTGAGA ATCCAGCCCT CATCTCTCGC   420

AGTGTTATCG GAACCACATT TGAGGGACGC GCTATTTACC TCCTGAAGGT TGGCAAAGCT   480

GGACAAAATA AGCCTGCCAT TTTCATGGAC TGTGGTTTCC ATGCCAGAGA GTGGATTTCT   540

CCTGCATTCT GCCAGTGGTT TGTAAGAGAG GCTGTTCGTA CCTATGGACG TGAGATCCAA   600

GTGACAGAGC TTCTCGACAA GTTAGACTTT TATGTCCTGC CTGTGCTCAA TATTGATGGC   660

TACATCTACA CCTGGACCAA GAGCCGATTT GGAGAAAGA CTCGCTCCAC CCATACTGGA   720

TCTAGCTGCA TTGGCACAGA CCCCAACAGA AATTTTGATG CTGGTTGGTG TGAAATTGGA   780

GCCTCTCGAA ACCCCTGTGA TGAAACTTAC TGTGGACCTG CCGCAGAGTC TGAAAAGGAA   840

-continued

```
ACCAAGGCCC TGGCTGATTT CATCCGCAAC AAACTCTCTT CCATCAAGGC ATATCTGACA    900

ATCCACTCGT ACTCCCAAAT GATGATCTAC CCTTACTCAT ATGCTTACAA ACTCGGTGAG    960

AACAATGCTG AGTTGAATGC CCTGGCTAAA GCTACTGTGA AGAACTTGC CTCACTGCAC     1020

GGCACCAAGT ACACATATGG CCCGGGAGCT ACAACAATCT ATCCTGCTGC TGGGGCTCT    1080

GACGACTGGG CTTATGACCA AGGAATCAGA TATTCCTTCA CCTTTGAACT TCGAGATACA    1140

GGCAGATATG GCTTTCTCCT TCCAGAATCC CAGATCCGGG CTACCTGCGA GGAGACCTTC    1200

CTGGCAATCA GTATGTTGC CAGCTACGTC CTGAACACC TGTACTAGTT GAGAAAGCTC     1260

GAG                                                                  1263
```

(2) INFORMATION FOR SEQ ID NO: 39:

(i) SEQUENCE CHARACTERISTICS:
        (A) LENGTH: 415 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 39:

```
Glu Leu Leu Val Leu Val Thr Val Ala Leu Ala Ser Ala His His Gly
 1               5                  10                  15

Gly Glu His Phe Glu Gly Glu Lys Val Phe Arg Val Asn Val Glu Asp
                20                  25                  30

Glu Asn His Ile Asn Ile Ile Arg Glu Leu Ala Ser Thr Thr Gln Ile
            35                  40                  45

Asp Phe Trp Lys Pro Asp Ser Val Thr Gln Ile Lys Pro His Ser Thr
        50                  55                  60

Val Asp Phe Arg Val Lys Ala Glu Asp Thr Val Thr Val Glu Asn Val
 65                  70                  75                  80

Leu Lys Gln Asn Glu Leu Gln Tyr Lys Val Leu Ile Ser Asn Leu Arg
                85                  90                  95

Asn Val Val Glu Ala Gln Phe Asp Ser Arg Val Arg Ala Thr Gly His
                100                 105                 110

Ser Tyr Glu Lys Tyr Asn Lys Trp Glu Thr Ile Glu Ala Trp Thr Gln
            115                 120                 125

Gln Val Ala Thr Glu Asn Pro Ala Leu Ile Ser Arg Ser Val Ile Gly
        130                 135                 140

Thr Thr Phe Glu Gly Arg Ala Ile Tyr Leu Leu Lys Val Gly Lys Ala
145                 150                 155                 160

Gly Gln Asn Lys Pro Ala Ile Phe Met Asp Cys Gly Phe His Ala Arg
                165                 170                 175

Glu Trp Ile Ser Pro Ala Phe Cys Gln Trp Phe Val Arg Glu Ala Val
            180                 185                 190

Arg Thr Tyr Gly Arg Glu Ile Gln Val Thr Glu Leu Leu Asp Lys Leu
        195                 200                 205

Asp Phe Tyr Val Leu Pro Val Leu Asn Ile Asp Gly Tyr Ile Tyr Thr
    210                 215                 220

Trp Thr Lys Ser Arg Phe Trp Arg Lys Thr Arg Ser Thr His Thr Gly
225                 230                 235                 240

Ser Ser Cys Ile Gly Thr Asp Pro Asn Arg Asn Phe Asp Ala Gly Trp
                245                 250                 255

Cys Glu Ile Gly Ala Ser Arg Asn Pro Cys Asp Glu Thr Tyr Cys Gly
            260                 265                 270
```

```
Pro Ala Ala Glu Ser Glu Lys Glu Thr Lys Ala Leu Ala Asp Phe Ile
        275                 280                 285

Arg Asn Lys Leu Ser Ser Ile Lys Ala Tyr Leu Thr Ile His Ser Tyr
    290                 295                 300

Ser Gln Met Met Ile Tyr Pro Tyr Ser Tyr Ala Tyr Lys Leu Gly Glu
305                 310                 315                 320

Asn Asn Ala Glu Leu Asn Ala Leu Ala Lys Ala Thr Val Lys Glu Leu
                325                 330                 335

Ala Ser Leu His Gly Thr Lys Tyr Thr Tyr Gly Pro Gly Ala Thr Thr
            340                 345                 350

Ile Tyr Pro Ala Ala Gly Gly Ser Asp Asp Trp Ala Tyr Asp Gln Gly
        355                 360                 365

Ile Arg Tyr Ser Phe Thr Phe Glu Leu Arg Asp Thr Gly Arg Tyr Gly
        370                 375                 380

Phe Leu Leu Pro Glu Ser Gln Ile Arg Ala Thr Cys Glu Glu Thr Phe
385                 390                 395                 400

Leu Ala Ile Lys Tyr Val Ala Ser Tyr Val Leu Glu His Leu Tyr
            405                 410                 415
```

(2) INFORMATION FOR SEQ ID NO: 40:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 40:

```
GCCGGGTTTG CGCAACTGGT CACTCTTACG AGAAG                              35
```

(2) INFORMATION FOR SEQ ID NO: 41:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 41:

```
CCGGAATTCT TATTAGTTCA GGTCCTCCTC AGAGATCAGC TTCTGCTCCT CGAACTCATG    60

GTGGTGATGG TGGTGGTACA GGTGTTCC                                      88
```

(2) INFORMATION FOR SEQ ID NO: 42:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 42:

```
TTAGCGGATC CTGCCTGACG GT                                            22
```

(2) INFORMATION FOR SEQ ID NO: 43:

(i) SEQUENCE CHARACTERISTICS:

```
        (A) LENGTH: 23 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 43:

GGCTGGATTC TCAGTGGCGA CTT                                         23

(2) INFORMATION FOR SEQ ID NO: 44:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 44:

ACCTCTAGGG TCCCCAATTA                                             20

(2) INFORMATION FOR SEQ ID NO: 45:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 45:

CAAGTCGCCA CTGAGAATCC AGC                                         23

(2) INFORMATION FOR SEQ ID NO: 46:

(i) SEQUENCE CHARACTERISTICS:
        (A) LENGTH: 1053 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: CDS
        (B) LOCATION:1..1047

(ix) FEATURE:
        (A) NAME/KEY: mat_peptide
        (B) LOCATION:67..1047

(xi) SEQUENCE DESCRIPTION: SEQ ID NO: 46:

ATG AAA TAC CTA TTG CCT ACG GCA GCC GCT GGA TTG TTA TTA CTC GCT    48
Met Lys Tyr Leu Leu Pro Thr Ala Ala Ala Gly Leu Leu Leu Leu Ala
-22     -20             -15                 -10

GCC CAA CCA GCC ATG GCG GCA ACT GGT CAC TCT TAC GAG AAG TAC AAC    96
Ala Gln Pro Ala Met Ala Ala Thr Gly His Ser Tyr Glu Lys Tyr Asn
     -5          Ala  Ala   1                5                 10

AAG TGG GAA ACG ATA GAG GCT TGG ACT CAA CAA GTC GCC ACT GAG AAT   144
Lys Trp Glu Thr Ile Glu Ala Trp Thr Gln Gln Val Ala Thr Glu Asn
                15              20                  25

CCA GCC CTC ATC TCT CGC AGT GTT ATC GGA ACC ACA TTT GAG GGA CGC   192
Pro Ala Leu Ile Ser Arg Ser Val Ile Gly Thr Thr Phe Glu Gly Arg
            30              35                  40

GCT ATT TAC CTC CTG AAG GTT GGC AAA GCT GGA CAA AAT AAG CCT GCC   240
```

```
                                                    -continued

Ala Ile Tyr Leu Leu Lys Val Gly Lys Ala Gly Gln Asn Lys Pro Ala
        45                  50                  55

ATT TTC ATG GAC TGT GGT TTC CAT GCC AGA GAG TGG ATT TCT CCT GCA       288
Ile Phe Met Asp Cys Gly Phe His Ala Arg Glu Trp Ile Ser Pro Ala
    60                  65                  70

TTC TGC CAG TGG TTT GTA AGA GAG GCT GTT CGT ACC TAT GGA CGT GAG       336
Phe Cys Gln Trp Phe Val Arg Glu Ala Val Arg Thr Tyr Gly Arg Glu
75                  80                  85                  90

ATC CAA GTG ACA GAG CTT CTC GAC AAG TTA GAC TTT TAT GTC CTG CCT       384
Ile Gln Val Thr Glu Leu Leu Asp Lys Leu Asp Phe Tyr Val Leu Pro
                95                  100                 105

GTG CTC AAT ATT GAT GGC TAC ATC TAC ACC TGG ACC AAG AGC CGA TTT       432
Val Leu Asn Ile Asp Gly Tyr Ile Tyr Thr Trp Thr Lys Ser Arg Phe
            110                 115                 120

TGG AGA AAG ACT CGC TCC ACC CAT ACT GGA TCT AGC TGC ATT GGC ACA       480
Trp Arg Lys Thr Arg Ser Thr His Thr Gly Ser Ser Cys Ile Gly Thr
        125                 130                 135

GAC CCC AAC AGA AAT TTT GAT GCT GGT TGG TGT GAA ATT GGA GCC TCT       528
Asp Pro Asn Arg Asn Phe Asp Ala Gly Trp Cys Glu Ile Gly Ala Ser
    140                 145                 150

CGA AAC CCC TGT GAT GAA ACT TAC TGT GGA CCT GCC GCA GAG TCT GAA       576
Arg Asn Pro Cys Asp Glu Thr Tyr Cys Gly Pro Ala Ala Glu Ser Glu
155                 160                 165                 170

AAG GAG ACC AAG GCC CTG GCT GAT TTC ATC CGC AAC AAA CTC TCT TCC       624
Lys Glu Thr Lys Ala Leu Ala Asp Phe Ile Arg Asn Lys Leu Ser Ser
                175                 180                 185

ATC AAG GCA TAT CTG ACA ATC CAC TCG TAC TCC CAA ATG ATG ATC TAC       672
Ile Lys Ala Tyr Leu Thr Ile His Ser Tyr Ser Gln Met Met Ile Tyr
            190                 195                 200

CCT TAC TCA TAT GCT TAC AAA CTC GGT GAG AAC AAT GCT GAG TTG AAT       720
Pro Tyr Ser Tyr Ala Tyr Lys Leu Gly Glu Asn Asn Ala Glu Leu Asn
        205                 210                 215

GCC CTG GCT AAA GCT ACT GTG AAA GAA CTT GCC TCA CTG CAC GGC ACC       768
Ala Leu Ala Lys Ala Thr Val Lys Glu Leu Ala Ser Leu His Gly Thr
    220                 225                 230

AAG TAC ACA TAT GGC CCG GGA GCT ACA ACA ATC TAT CCT GCT GCT GGG       816
Lys Tyr Thr Tyr Gly Pro Gly Ala Thr Thr Ile Tyr Pro Ala Ala Gly
235                 240                 245                 250

GGC TCT GAC GAC TGG GCT TAT GAC CAA GGA ATC AGA TAT TCC TTC ACC       864
Gly Ser Asp Asp Trp Ala Tyr Asp Gln Gly Ile Arg Tyr Ser Phe Thr
                255                 260                 265

TTT GAA CTT CGA GAT ACA GGC AGA TAT GGC TTT CTC CTT CCA GAA TCC       912
Phe Glu Leu Arg Asp Thr Gly Arg Tyr Gly Phe Leu Leu Pro Glu Ser
            270                 275                 280

CAG ATC CGG GCT ACC TGC GAG GAG ACC TTC CTG GCA ATC AAG TAT GTT       960
Gln Ile Arg Ala Thr Cys Glu Glu Thr Phe Leu Ala Ile Lys Tyr Val
        285                 290                 295

GCC AGC TAC GTC CTG GAA CAC CTG TAC CAC CAT CAC CAC CAT GAG          1008
Ala Ser Tyr Val Leu Glu His Leu Tyr His His His His His Glu
    300                 305                 310

TTC GAG GAG CAG AAG CTG ATC TCT GAG GAG GAC CTG AAC TAATAA           1053
Phe Glu Glu Gln Lys Leu Ile Ser Glu Glu Asp Leu Asn
315                 320                 325

(2) INFORMATION FOR SEQ ID NO: 47:

(i) SEQUENCE CHARACTERISTICS:
        (A) LENGTH: 349 amino acids
        (B) TYPE: amino acid
        (D) TOPOLOGY: linear
```

(ii) MOLECULE TYPE: protein (xi) SEQUENCE DESCRIPTION: SEQ ID NO: 47:

| Met | Lys | Tyr | Leu | Leu | Pro | Thr | Ala | Ala | Gly | Leu | Leu | Leu | Ala |
|---|---|---|---|---|---|---|---|---|---|---|---|---|---|
| -22 | | -20 | | | | -15 | | | | -10 | | | |

| Ala | Gln | Pro | Ala | Met | Ala | Ala | Thr | Gly | His | Ser | Tyr | Glu | Lys | Tyr | Asn |
|---|---|---|---|---|---|---|---|---|---|---|---|---|---|---|---|
| | -5 | | | | | 1 | | | | 5 | | | | | 10 |

| Lys | Trp | Glu | Thr | Ile | Glu | Ala | Trp | Thr | Gln | Gln | Val | Ala | Thr | Glu | Asn |
|---|---|---|---|---|---|---|---|---|---|---|---|---|---|---|---|
| | | | | 15 | | | | | 20 | | | | | 25 | |

| Pro | Ala | Leu | Ile | Ser | Arg | Ser | Val | Ile | Gly | Thr | Thr | Phe | Glu | Gly | Arg |
|---|---|---|---|---|---|---|---|---|---|---|---|---|---|---|---|
| | | | 30 | | | | | 35 | | | | | 40 | | |

| Ala | Ile | Tyr | Leu | Leu | Lys | Val | Gly | Lys | Ala | Gly | Gln | Asn | Lys | Pro | Ala |
|---|---|---|---|---|---|---|---|---|---|---|---|---|---|---|---|
| | | 45 | | | | | 50 | | | | | 55 | | | |

| Ile | Phe | Met | Asp | Cys | Gly | Phe | His | Ala | Arg | Glu | Trp | Ile | Ser | Pro | Ala |
|---|---|---|---|---|---|---|---|---|---|---|---|---|---|---|---|
| | 60 | | | | | 65 | | | | | 70 | | | | |

| Phe | Cys | Gln | Trp | Phe | Val | Arg | Glu | Ala | Val | Arg | Thr | Tyr | Gly | Arg | Glu |
|---|---|---|---|---|---|---|---|---|---|---|---|---|---|---|---|
| 75 | | | | | 80 | | | | | 85 | | | | | 90 |

| Ile | Gln | Val | Thr | Glu | Leu | Leu | Asp | Lys | Leu | Asp | Phe | Tyr | Val | Leu | Pro |
|---|---|---|---|---|---|---|---|---|---|---|---|---|---|---|---|
| | | | | 95 | | | | | 100 | | | | | 105 | |

| Val | Leu | Asn | Ile | Asp | Gly | Tyr | Ile | Tyr | Thr | Trp | Thr | Lys | Ser | Arg | Phe |
|---|---|---|---|---|---|---|---|---|---|---|---|---|---|---|---|
| | | | 110 | | | | | 115 | | | | | 120 | | |

| Trp | Arg | Lys | Thr | Arg | Ser | Thr | His | Thr | Gly | Ser | Ser | Cys | Ile | Gly | Thr |
|---|---|---|---|---|---|---|---|---|---|---|---|---|---|---|---|
| | | 125 | | | | | 130 | | | | | 135 | | | |

| Asp | Pro | Asn | Arg | Asn | Phe | Asp | Ala | Gly | Trp | Cys | Glu | Ile | Gly | Ala | Ser |
|---|---|---|---|---|---|---|---|---|---|---|---|---|---|---|---|
| | 140 | | | | | 145 | | | | | 150 | | | | |

| Arg | Asn | Pro | Cys | Asp | Glu | Thr | Tyr | Cys | Gly | Pro | Ala | Ala | Glu | Ser | Glu |
|---|---|---|---|---|---|---|---|---|---|---|---|---|---|---|---|
| 155 | | | | | 160 | | | | | 165 | | | | | 170 |

| Lys | Glu | Thr | Lys | Ala | Leu | Ala | Asp | Phe | Ile | Arg | Asn | Lys | Leu | Ser | Ser |
|---|---|---|---|---|---|---|---|---|---|---|---|---|---|---|---|
| | | | 175 | | | | | 180 | | | | | 185 | | |

| Ile | Lys | Ala | Tyr | Leu | Thr | Ile | His | Ser | Tyr | Ser | Gln | Met | Met | Ile | Tyr |
|---|---|---|---|---|---|---|---|---|---|---|---|---|---|---|---|
| | | | 190 | | | | | 195 | | | | | 200 | | |

| Pro | Tyr | Ser | Tyr | Ala | Tyr | Lys | Leu | Gly | Glu | Asn | Asn | Ala | Glu | Leu | Asn |
|---|---|---|---|---|---|---|---|---|---|---|---|---|---|---|---|
| | | 205 | | | | | 210 | | | | | 215 | | | |

| Ala | Leu | Ala | Lys | Ala | Thr | Val | Lys | Glu | Leu | Ala | Ser | Leu | His | Gly | Thr |
|---|---|---|---|---|---|---|---|---|---|---|---|---|---|---|---|
| 220 | | | | | 225 | | | | | 230 | | | | | |

| Lys | Tyr | Thr | Tyr | Gly | Pro | Gly | Ala | Thr | Thr | Ile | Tyr | Pro | Ala | Ala | Gly |
|---|---|---|---|---|---|---|---|---|---|---|---|---|---|---|---|
| 235 | | | | | 240 | | | | | 245 | | | | | 250 |

| Gly | Ser | Asp | Asp | Trp | Ala | Tyr | Asp | Gln | Gly | Ile | Arg | Tyr | Ser | Phe | Thr |
|---|---|---|---|---|---|---|---|---|---|---|---|---|---|---|---|
| | | | | 255 | | | | | 260 | | | | | 265 | |

| Phe | Glu | Leu | Arg | Asp | Thr | Gly | Arg | Tyr | Gly | Phe | Leu | Leu | Pro | Glu | Ser |
|---|---|---|---|---|---|---|---|---|---|---|---|---|---|---|---|
| | | | 270 | | | | | 275 | | | | | 280 | | |

| Gln | Ile | Arg | Ala | Thr | Cys | Glu | Glu | Thr | Phe | Leu | Ala | Ile | Lys | Tyr | Val |
|---|---|---|---|---|---|---|---|---|---|---|---|---|---|---|---|
| | | 285 | | | | | 290 | | | | | 295 | | | |

| Ala | Ser | Tyr | Val | Leu | Glu | His | Leu | Tyr | His | His | His | His | His | His | Glu |
|---|---|---|---|---|---|---|---|---|---|---|---|---|---|---|---|
| | 300 | | | | | 305 | | | | | 310 | | | | |

| Phe | Glu | Glu | Gln | Lys | Leu | Ile | Ser | Glu | Glu | Asp | Leu | Asn |
|---|---|---|---|---|---|---|---|---|---|---|---|---|
| 315 | | | | | 320 | | | | | 325 | | |

(2) INFORMATION FOR SEQ ID NO: 48:

(i) SEQUENCE CHARACTERISTICS:
        (A) LENGTH: 31 base pairs
        (B) TYPE: nucleic acid
        (C) STRANDEDNESS: single
        (D) TOPOLOGY: linear -continued (ii) MOLECULE TYPE: other nucleic acid (xi) SEQUENCE DESCRIPTION: SEQ ID NO: 48:

GTTATTACTC GCTGCCCAAC CAGCCATGGC G          31

(2) INFORMATION FOR SEQ ID NO: 49:

(i) SEQUENCE CHARACTERISTICS:
      (A) LENGTH: 41 base pairs
      (B) TYPE: nucleic acid
      (C) STRANDEDNESS: single
      (D) TOPOLOGY: linear (ii) MOLECULE TYPE: other nucleic acid (xi) SEQUENCE DESCRIPTION: SEQ ID NO: 49:

CTCTAGGAAT TCTTATTAGT ACAGGTGTTC CAGGACGTAG C          41

(2) INFORMATION FOR SEQ ID NO: 50:

(i) SEQUENCE CHARACTERISTICS:
      (A) LENGTH: 999 base pairs
      (B) TYPE: nucleic acid
      (C) STRANDEDNESS: single
      (D) TOPOLOGY: linear (ii) MOLECULE TYPE: other nucleic acid (ix) FEATURE:
      (A) NAME/KEY: CDS
      (B) LOCATION:1..987

(ix) FEATURE:
      (A) NAME/KEY: mat_peptide
      (B) LOCATION:67..987

(xi) SEQUENCE DESCRIPTION: SEQ ID NO: 50:

```
ATG AAA TAC CTA TTG CCT ACG GCA GCC GCT GGA TTG TTA TTA CTC GCTY      48
Met Lys Tyr Leu Leu Pro Thr Ala Ala Ala Gly Leu Leu Leu Leu Ala
-22     -20             -15                 -10

GCC CAA CCA GCC ATG GCG GCA ACT GGT CAC TCT TAC GAG AAG TAC AAC       96
Ala Gln Pro Ala Met Ala Ala Thr Gly His Ser Tyr Glu Lys Tyr Asn
         -5              1               5                      10

AAG TGG GAA ACG ATA GAG GCT TGG ACT CAA CAA GTC GCC ACT GAG AAT      144
Lys Trp Glu Thr Ile Glu Ala Trp Thr Gln Gln Val Ala Thr Glu Asn
                 15                  20                  25

CCA GCC CTC ATC TCT CGC AGT GTT ATC GGA ACC ACA TTT GAG GGA CGC      192
Pro Ala Leu Ile Ser Arg Ser Val Ile Gly Thr Thr Phe Glu Gly Arg
             30                  35                  40

GCT ATT TAC CTC CTG AAG GTT GGC AAA GCT GGA CAA AAT AAG CCT GCC      240
Ala Ile Tyr Leu Leu Lys Val Gly Lys Ala Gly Gln Asn Lys Pro Ala
         45                  50                  55

ATT TTC ATG GAC TGT GGT TTC CAT GCC AGA GAG TGG ATT TCT CCT GCA      288
Ile Phe Met Asp Cys Gly Phe His Ala Arg Glu Trp Ile Ser Pro Ala
     60                  65                  70

TTC TGC CAG TGG TTT GTA AGA GAG GCT GTT CGT ACC TAT GGA CGT GAG      336
Phe Cys Gln Trp Phe Val Arg Glu Ala Val Arg Thr Tyr Gly Arg Glu
 75                  80                  85                  90

ATC CAA GTG ACA GAG CTT CTC GAC AAG TTA GAC TTT TAT GTC CTG CCT      384
Ile Gln Val Thr Glu Leu Leu Asp Lys Leu Asp Phe Tyr Val Leu Pro
                 95                 100                 105

GTG CTC AAT ATT GAT GGC TAC ATC TAC ACC TGG ACC AAG AGC CGA TTT      432
Val Leu Asn Ile Asp Gly Tyr Ile Tyr Thr Trp Thr Lys Ser Arg Phe
             110                 115                 120

TGG AGA AAG ACT CGC TCC ACC CAT ACT GGA TCT AGC TGC ATT GGC ACA      480
```

-continued

```
Trp Arg Lys Thr Arg Ser Thr His Thr Gly Ser Ser Cys Ile Gly Thr
        125                 130                 135

GAC CCC AAC AGA AAT TTT GAT GCT GGT TGG TGT GAA ATT GGA GCC TCT        528
Asp Pro Asn Arg Asn Phe Asp Ala Gly Trp Cys Glu Ile Gly Ala Ser
        140                 145                 150

CGA AAC CCC TGT GAT GAA ACT TAC TGT GGA CCT GCC GCA GAG TCT GAA        576
Arg Asn Pro Cys Asp Glu Thr Tyr Cys Gly Pro Ala Ala Glu Ser Glu
155                 160                 165                 170

AAG GAG ACC AAG GCC CTG GCT GAT TTC ATC CGC AAC AAA CTC TCT TCC        624
Lys Glu Thr Lys Ala Leu Ala Asp Phe Ile Arg Asn Lys Leu Ser Ser
                175                 180                 185

ATC AAG GCA TAT CTG ACA ATC CAC TCG TAC TCC CAA ATG ATG ATC TAC        672
Ile Lys Ala Tyr Leu Thr Ile His Ser Tyr Ser Gln Met Met Ile Tyr
            190                 195                 200

CCT TAC TCA TAT GCT TAC AAA CTC GGT GAG AAC AAT GCT GAG TTG AAT        720
Pro Tyr Ser Tyr Ala Tyr Lys Leu Gly Glu Asn Asn Ala Glu Leu Asn
        205                 210                 215

GCC CTG GCT AAA GCT ACT GTG AAA GAA CTT GCC TCA CTG CAC GGC ACC        768
Ala Leu Ala Lys Ala Thr Val Lys Glu Leu Ala Ser Leu His Gly Thr
    220                 225                 230

AAG TAC ACA TAT GGC CCG GGA GCT ACA ACA ATC TAT CCT GCT GCT GGG        816
Lys Tyr Thr Tyr Gly Pro Gly Ala Thr Thr Ile Tyr Pro Ala Ala Gly
235                 240                 245                 250

GGC TCT GAC GAC TGG GCT TAT GAC CAA GGA ATC AGA TAT TCC TTC ACC        864
Gly Ser Asp Asp Trp Ala Tyr Asp Gln Gly Ile Arg Tyr Ser Phe Thr
                255                 260                 265

TTT GAA CTT CGA GAT ACA GGC AGA TAT GGC TTT CTC CTT CCA GAA TCC        912
Phe Glu Leu Arg Asp Thr Gly Arg Tyr Gly Phe Leu Leu Pro Glu Ser
            270                 275                 280

CAG ATC CGG GCT ACC TGC GAG GAG ACC TTC CTG GCA ATC AAG TAT GTT        960
Gln Ile Arg Ala Thr Cys Glu Glu Thr Phe Leu Ala Ile Lys Tyr Val
        285                 290                 295

GCC AGC TAC GTC CTG GAA CAC CTG TAC TAATAAGAAT TC                      999
Ala Ser Tyr Val Leu Glu His Leu Tyr
300                 305
```

(2) INFORMATION FOR SEQ ID NO: 51:

(i) SEQUENCE CHARACTERISTICS:
        (A) LENGTH: 329 amino acids
        (B) TYPE: amino acid
        (D) TOPOLOGY: linear (ii) MOLECULE TYPE: protein (xi) SEQUENCE DESCRIPTION: SEQ ID NO: 51:

```
Met Lys Tyr Leu Leu Pro Thr Ala Ala Ala Gly Leu Leu Leu Leu Ala
-22         -20                 -15                 -10

Ala Gln Pro Ala Met Ala Ala Thr Gly His Ser Tyr Glu Lys Tyr Asn
        -5                  1                   5                   10

Lys Trp Glu Thr Ile Glu Ala Trp Thr Gln Val Ala Thr Glu Asn
                15                  20                  25

Pro Ala Leu Ile Ser Arg Ser Val Ile Gly Thr Thr Phe Glu Gly Arg
            30                  35                  40

Ala Ile Tyr Leu Leu Lys Val Gly Lys Ala Gly Gln Asn Lys Pro Ala
        45                  50                  55

Ile Phe Met Asp Cys Gly Phe His Ala Arg Glu Trp Ile Ser Pro Ala
    60                  65                  70

Phe Cys Gln Trp Phe Val Arg Glu Ala Val Arg Thr Tyr Gly Arg Glu
75                  80                  85                  90
```

```
Ile Gln Val Thr Glu Leu Leu Asp Lys Leu Asp Phe Tyr Val Leu Pro
                95                 100                105
Val Leu Asn Ile Asp Gly Tyr Ile Tyr Thr Trp Thr Lys Ser Arg Phe
            110                 115                120
Trp Arg Lys Thr Arg Ser Thr His Thr Gly Ser Ser Cys Ile Gly Thr
        125                 130                135
Asp Pro Asn Arg Asn Phe Asp Ala Gly Trp Cys Glu Ile Gly Ala Ser
    140                 145                150
Arg Asn Pro Cys Asp Glu Thr Tyr Cys Gly Pro Ala Ala Glu Ser Glu
155                 160                 165                170
Lys Glu Thr Lys Ala Leu Ala Asp Phe Ile Arg Asn Lys Leu Ser Ser
            175                 180                185
Ile Lys Ala Tyr Leu Thr Ile His Ser Tyr Ser Gln Met Met Ile Tyr
        190                 195                200
Pro Tyr Ser Tyr Ala Tyr Lys Leu Gly Glu Asn Asn Ala Glu Leu Asn
    205                 210                215
Ala Leu Ala Lys Ala Thr Val Lys Glu Leu Ala Ser Leu His Gly Thr
    220                 225                230
Lys Tyr Thr Tyr Gly Pro Gly Ala Thr Thr Ile Tyr Pro Ala Ala Gly
235                 240                 245                250
Gly Ser Asp Asp Trp Ala Tyr Asp Gln Gly Ile Arg Tyr Ser Phe Thr
            255                 260                265
Phe Glu Leu Arg Asp Thr Gly Arg Tyr Gly Phe Leu Leu Pro Glu Ser
            270                 275                280
Gln Ile Arg Ala Thr Cys Glu Glu Thr Phe Leu Ala Ile Lys Tyr Val
        285                 290                295
Ala Ser Tyr Val Leu Glu His Leu Tyr
300                 305
```

(2) INFORMATION FOR SEQ ID NO: 52:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 52:

CCAACCAGCC ATGGCGCATC ATGGTGGTGA GCAC                              34

(2) INFORMATION FOR SEQ ID NO: 53:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 53:

GGCTGGATTC TCAGTGGCGA CTT                                          23

(2) INFORMATION FOR SEQ ID NO: 54:

(i) SEQUENCE CHARACTERISTICS:
        (A) LENGTH: 21 base pairs
        (B) TYPE: nucleic acid (C) STRANDEDNESS: single
            (D) TOPOLOGY: linear (ii) MOLECULE TYPE: other nucleic acid (xi) SEQUENCE DESCRIPTION: SEQ ID NO: 54:

GGAGAAAGCC ATATCTGCCT G                                                    21

(2) INFORMATION FOR SEQ ID NO: 55:

(i) SEQUENCE CHARACTERISTICS:
            (A) LENGTH: 1284 base pairs
            (B) TYPE: nucleic acid
            (C) STRANDEDNESS: single
            (D) TOPOLOGY: linear (ii) MOLECULE TYPE: other nucleic acid (ix) FEATURE:
            (A) NAME/KEY: CDS
            (B) LOCATION:1..1272

(ix) FEATURE:
            (A) NAME/KEY: mat_peptide
            (B) LOCATION:352..1272

(xi) SEQUENCE DESCRIPTION: SEQ ID NO: 55:

```
ATG AAA TAC CTA TTG CCT ACG GCA GCC GCT GGA TTG TTA TTA CTC GCT        48
Met Lys Tyr Leu Leu Pro Thr Ala Ala Ala Gly Leu Leu Leu Leu Ala
-117     -115              -110              -105

GCC CAA CCA GCC ATG GCG CAT CAT GGT GGT GAG CAC TTT GAA GGC GAG        96
Ala Gln Pro Ala Met Ala His His Gly Gly Glu His Phe Glu Gly Glu
        -100              -95               -90

AAG GTG TTC CGT GTT AAC GTT GAA GAT GAA AAT CAC ATT AAC ATA ATC       144
Lys Val Phe Arg Val Asn Val Glu Asp Glu Asn His Ile Asn Ile Ile
-85              -80               -75                       -70

CGC GAG TTG GCC AGC ACG ACC CAG ATT GAC TTC TGG AAG CCA GAT TCT       192
Arg Glu Leu Ala Ser Thr Thr Gln Ile Asp Phe Trp Lys Pro Asp Ser
                -65               -60                       -55

GTC ACA CAA ATC AAA CCT CAC AGT ACA GTT GAC TTC CGT GTT AAA GCA       240
Val Thr Gln Ile Lys Pro His Ser Thr Val Asp Phe Arg Val Lys Ala
        -50               -45                       -40

GAA GAT ACT GTC ACT GTG GAG AAT GTT CTA AAG CAG AAT GAA CTA CAA       288
Glu Asp Thr Val Thr Val Glu Asn Val Leu Lys Gln Asn Glu Leu Gln
    -35               -30                   -25

TAC AAG GTA CTG ATA AGC AAC CTG AGA AAT GTG GTG GAG GCT CAG TTT       336
Tyr Lys Val Leu Ile Ser Asn Leu Arg Asn Val Val Glu Ala Gln Phe
    -20               -15                   -10

GAT AGC CGG GTT CGT GCA ACA GGA CAC AGT TAT GAG AAG TAC AAC AAG       384
Asp Ser Arg Val Arg Ala Thr Gly His Ser Tyr Glu Lys Tyr Asn Lys
-5                       1               5                   10

TGG GAA ACG ATA GAG GCT TGG ACT CAA CAA GTC GCC ACT GAG AAT CCA       432
Trp Glu Thr Ile Glu Ala Trp Thr Gln Gln Val Ala Thr Glu Asn Pro
            15                  20                  25

GCC CTC ATC TCT CGC AGT GTT ATC GGA ACC ACA TTT GAG GGA CGC GCT       480
Ala Leu Ile Ser Arg Ser Val Ile Gly Thr Thr Phe Glu Gly Arg Ala
            30                  35                  40

ATT TAC CTC CTG AAG GTT GGC AAA GCT GGA CAA AAT AAG CCT GCC ATT       528
Ile Tyr Leu Leu Lys Val Gly Lys Ala Gly Gln Asn Lys Pro Ala Ile
            45                  50                  55

TTC ATG GAC TGT GGT TTC CAT GCC AGA GAG TGG ATT TCT CCT GCA TTC       576
Phe Met Asp Cys Gly Phe His Ala Arg Glu Trp Ile Ser Pro Ala Phe
60                  65                  70                  75

TGC CAG TGG TTT GTA AGA GAG GCT GTT CGT ACC TAT GGA CGT GAG ATC       624
```

```
Cys Gln Trp Phe Val Arg Glu Ala Val Arg Thr Tyr Gly Arg Glu Ile
            80                  85                  90

CAA GTG ACA GAG CTT CTC GAC AAG TTA GAC TTT TAT GTC CTG CCT GTG           672
Gln Val Thr Glu Leu Leu Asp Lys Leu Asp Phe Tyr Val Leu Pro Val
        95                  100                 105

CTC AAT ATT GAT GGC TAC ATC TAC ACC TGG ACC AAG AGC CGA TTT TGG           720
Leu Asn Ile Asp Gly Tyr Ile Tyr Thr Trp Thr Lys Ser Arg Phe Trp
    110                 115                 120

AGA AAG ACT CGC TCC ACC CAT ACT GGA TCT AGC TGC ATT GGC ACA GAC           768
Arg Lys Thr Arg Ser Thr His Thr Gly Ser Ser Cys Ile Gly Thr Asp
125                 130                 135

CCC AAC AGA AAT TTT GAT GCT GGT TGG TGT GAA ATT GGA GCC TCT CGA           816
Pro Asn Arg Asn Phe Asp Ala Gly Trp Cys Glu Ile Gly Ala Ser Arg
140                 145                 150                 155

AAC CCC TGT GAT GAA ACT TAC TGT GGA CCT GCC GCA GAG TCT GAA AAG           864
Asn Pro Cys Asp Glu Thr Tyr Cys Gly Pro Ala Ala Glu Ser Glu Lys
                160                 165                 170

GAG ACC AAG GCC CTG GCT GAT TTC ATC CGC AAC AAA CTC TCT TCC ATC           912
Glu Thr Lys Ala Leu Ala Asp Phe Ile Arg Asn Lys Leu Ser Ser Ile
                175                 180                 185

AAG GCA TAT CTG ACA ATC CAC TCG TAC TCC CAA ATG ATG ATC TAC CCT           960
Lys Ala Tyr Leu Thr Ile His Ser Tyr Ser Gln Met Met Ile Tyr Pro
                190                 195                 200

TAC TCA TAT GCT TAC AAA CTC GGT GAG AAC AAT GCT GAG TTG AAT GCC          1008
Tyr Ser Tyr Ala Tyr Lys Leu Gly Glu Asn Asn Ala Glu Leu Asn Ala
205                 210                 215

CTG GCT AAA GCT ACT GTG AAA GAA CTT GCC TCA CTG CAC GGC ACC AAG          1056
Leu Ala Lys Ala Thr Val Lys Glu Leu Ala Ser Leu His Gly Thr Lys
220                 225                 230                 235

TAC ACA TAT GGC CCG GGA GCT ACA ACA ATC TAT CCT GCT GCT GGG GGC          1104
Tyr Thr Tyr Gly Pro Gly Ala Thr Thr Ile Tyr Pro Ala Ala Gly Gly
                240                 245                 250

TCT GAC GAC TGG GCT TAT GAC CAA GGA ATC AGA TAT TCC TTC ACC TTT          1152
Ser Asp Asp Trp Ala Tyr Asp Gln Gly Ile Arg Tyr Ser Phe Thr Phe
                255                 260                 265

GAA CTT CGA GAT ACA GGC AGA TAT GGC TTT CTC CTT CCA GAA TCC CAG          1200
Glu Leu Arg Asp Thr Gly Arg Tyr Gly Phe Leu Leu Pro Glu Ser Gln
            270                 275                 280

ATC CGG GCT ACC TGC GAG GAG ACC TTC CTG GCA ATC AAG TAT GTT GCC          1248
Ile Arg Ala Thr Cys Glu Glu Thr Phe Leu Ala Ile Lys Tyr Val Ala
285                 290                 295

AGC TAC GTC CTG GAA CAC CTG TAC TAATAAGAAT TC                            1284
Ser Tyr Val Leu Glu His Leu Tyr
300                 305
```

(2) INFORMATION FOR SEQ ID NO: 56:

(i) SEQUENCE CHARACTERISTICS:
        (A) LENGTH: 424 amino acids
        (B) TYPE: amino acid
        (D) TOPOLOGY: linear (ii) MOLECULE TYPE: protein (xi) SEQUENCE DESCRIPTION: SEQ ID NO: 56:

```
Met Lys Tyr Leu Leu Pro Thr Ala Ala Ala Gly Leu Leu Leu Leu Ala
        -115                -110                -105

Ala Gln Pro Ala Met Ala His His Gly Gly Glu His Phe Glu Gly Glu
    -100                -95                 -90

Lys Val Phe Arg Val Asn Val Glu Asp Glu Asn His Ile Asn Ile Ile
-85                 -80                 -75                 -70
```

```
Arg Glu Leu Ala Ser Thr Thr Gln Ile Asp Phe Trp Lys Pro Asp Ser
            -65             -60              -55

Val Thr Gln Ile Lys Pro His Ser Thr Val Asp Phe Arg Val Lys Ala
            -50             -45              -40

Glu Asp Thr Val Thr Val Glu Asn Val Leu Lys Gln Asn Glu Leu Gln
            -35             -30              -25

Tyr Lys Val Leu Ile Ser Asn Leu Arg Asn Val Val Glu Ala Gln Phe
            -20             -15              -10

Asp Ser Arg Val Arg Ala Thr Gly His Ser Tyr Glu Lys Tyr Asn Lys
 -5              1               5               10

Trp Glu Thr Ile Glu Ala Trp Thr Gln Gln Val Ala Thr Glu Asn Pro
             15              20               25

Ala Leu Ile Ser Arg Ser Val Ile Gly Thr Thr Phe Glu Gly Arg Ala
             30              35               40

Ile Tyr Leu Leu Lys Val Gly Lys Ala Gly Gln Asn Lys Pro Ala Ile
             45              50               55

Phe Met Asp Cys Gly Phe His Ala Arg Glu Trp Ile Ser Pro Ala Phe
 60              65              70                75

Cys Gln Trp Phe Val Arg Glu Ala Val Arg Thr Tyr Gly Arg Glu Ile
             80              85               90

Gln Val Thr Glu Leu Leu Asp Lys Leu Asp Phe Tyr Val Leu Pro Val
             95             100              105

Leu Asn Ile Asp Gly Tyr Ile Tyr Thr Trp Thr Lys Ser Arg Phe Trp
            110             115              120

Arg Lys Thr Arg Ser Thr His Thr Gly Ser Ser Cys Ile Gly Thr Asp
            125             130              135

Pro Asn Arg Asn Phe Asp Ala Gly Trp Cys Glu Ile Gly Ala Ser Arg
140             145             150              155

Asn Pro Cys Asp Glu Thr Tyr Cys Gly Pro Ala Ala Glu Ser Glu Lys
            160             165              170

Glu Thr Lys Ala Leu Ala Asp Phe Ile Arg Asn Lys Leu Ser Ser Ile
            175             180              185

Lys Ala Tyr Leu Thr Ile His Ser Tyr Ser Gln Met Met Ile Tyr Pro
            190             195              200

Tyr Ser Tyr Ala Tyr Lys Leu Gly Glu Asn Asn Ala Glu Leu Asn Ala
205             210             215

Leu Ala Lys Ala Thr Val Lys Glu Leu Ala Ser Leu His Gly Thr Lys
220             225             230              235

Tyr Thr Tyr Gly Pro Gly Ala Thr Thr Ile Tyr Pro Ala Ala Gly Gly
            240             245              250

Ser Asp Asp Trp Ala Tyr Asp Gln Gly Ile Arg Tyr Ser Phe Thr Phe
            255             260              265

Glu Leu Arg Asp Thr Gly Arg Tyr Gly Phe Leu Leu Pro Glu Ser Gln
            270             275              280

Ile Arg Ala Thr Cys Glu Glu Thr Phe Leu Ala Ile Lys Tyr Val Ala
            285             290              295

Ser Tyr Val Leu Glu His Leu Tyr
300             305

(2) INFORMATION FOR SEQ ID NO: 57:

(i) SEQUENCE CHARACTERISTICS:
        (A) LENGTH: 25 base pairs
        (B) TYPE: nucleic acid
```

(C) STRANDEDNESS: single
            (D) TOPOLOGY: linear (ii) MOLECULE TYPE: other nucleic acid (xi) SEQUENCE DESCRIPTION: SEQ ID NO: 57:

GGTCATAAGC CCAGTCTTTA GAGCC                                              25

(2) INFORMATION FOR SEQ ID NO: 58:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO: 58:

CCTGCTGCTG GGGGCTCTAA AGACTGG                                            27

(2) INFORMATION FOR SEQ ID NO: 59:

(i) SEQUENCE CHARACTERISTICS:
            (A) LENGTH: 1059 base pairs
            (B) TYPE: nucleic acid
            (C) STRANDEDNESS: single
            (D) TOPOLOGY: linear (ii) MOLECULE TYPE: other nucleic acid (ix) FEATURE:
            (A) NAME/KEY: CDS
            (B) LOCATION:1..1047

(ix) FEATURE:
            (A) NAME/KEY: mat_peptide
            (B) LOCATION:67..1047

(xi) SEQUENCE DESCRIPTION: SEQ ID NO: 59:

```
ATG AAA TAC CTA TTG CCT ACG GCA GCC GCT GGA TTG TTA TTA CTC GCT          48
Met Lys Tyr Leu Leu Pro Thr Ala Ala Ala Gly Leu Leu Leu Leu Ala
-22     -20             -15                 -10

GCC CAA CCA GCC ATG GCG GCA ACT GGT CAC TCT TAC GAG AAG TAC AAC          96
Ala Gln Pro Ala Met Ala Ala Thr Gly His Ser Tyr Glu Lys Tyr Asn
    -5              1               5                   10

AAG TGG GAA ACG ATA GAG GCT TGG ACT CAA CAA GTC GCC ACT GAG AAT         144
Lys Trp Glu Thr Ile Glu Ala Trp Thr Gln Gln Val Ala Thr Glu Asn
            15                  20                  25

CCA GCC CTC ATC TCT CGC AGT GTT ATC GGA ACC ACA TTT GAG GGA CGC         192
Pro Ala Leu Ile Ser Arg Ser Val Ile Gly Thr Thr Phe Glu Gly Arg
                30                  35                  40

GCT ATT TAC CTC CTG AAG GTT GGC AAA GCT GGA CAA AAT AAG CCT GCC         240
Ala Ile Tyr Leu Leu Lys Val Gly Lys Ala Gly Gln Asn Lys Pro Ala
            45                  50                  55

ATT TTC ATG GAC TGT GGT TTC CAT GCC AGA GAG TGG ATT TCT CCT GCA         288
Ile Phe Met Asp Cys Gly Phe His Ala Arg Glu Trp Ile Ser Pro Ala
        60                  65                  70

TTC TGC CAG TGG TTT GTA AGA GAG GCT GTT CGT ACC TAT GGA CGT GAG         336
Phe Cys Gln Trp Phe Val Arg Glu Ala Val Arg Thr Tyr Gly Arg Glu
75                  80                  85                  90

ATC CAA GTG ACA GAG CTT CTC GAC AAG TTA GAC TTT TAT GTC CTG CCT         384
Ile Gln Val Thr Glu Leu Leu Asp Lys Leu Asp Phe Tyr Val Leu Pro
                95                  100                 105

GTG CTC AAT ATT GAT GGC TAC ATC TAC ACC TGG ACC AAG AGC CGA TTT         432
Val Leu Asn Ile Asp Gly Tyr Ile Tyr Thr Trp Thr Lys Ser Arg Phe
```

```
                110                  115                  120
TGG AGA AAG ACT CGC TCC ACC CAT ACT GGA TCT AGC TGC ATT GGC ACA         480
Trp Arg Lys Thr Arg Ser Thr His Thr Gly Ser Ser Cys Ile Gly Thr
        125                  130                  135

GAC CCC AAC AGA AAT TTT GAT GCT GGT TGG TGT GAA ATT GGA GCC TCT         528
Asp Pro Asn Arg Asn Phe Asp Ala Gly Trp Cys Glu Ile Gly Ala Ser
    140                  145                  150

CGA AAC CCC TGT GAT GAA ACT TAC TGT GGA CCT GCC GCA GAG TCT GAA         576
Arg Asn Pro Cys Asp Glu Thr Tyr Cys Gly Pro Ala Ala Glu Ser Glu
155                  160                  165                  170

AAG GAG ACC AAG GCC CTG GCT GAT TTC ATC CGC AAC AAA CTC TCT TCC         624
Lys Glu Thr Lys Ala Leu Ala Asp Phe Ile Arg Asn Lys Leu Ser Ser
                175                  180                  185

ATC AAG GCA TAT CTG ACA ATC CAC TCG TAC TCC CAA ATG ATG ATC TAC         672
Ile Lys Ala Tyr Leu Thr Ile His Ser Tyr Ser Gln Met Met Ile Tyr
            190                  195                  200

CCT TAC TCA TAT GCT TAC AAA CTC GGT GAG AAC AAT GCT GAG TTG AAT         720
Pro Tyr Ser Tyr Ala Tyr Lys Leu Gly Glu Asn Asn Ala Glu Leu Asn
        205                  210                  215

GCC CTG GCT AAA GCT ACT GTG AAA GAA CTT GCC TCA CTG CAC GGC ACC         768
Ala Leu Ala Lys Ala Thr Val Lys Glu Leu Ala Ser Leu His Gly Thr
    220                  225                  230

AAG TAC ACA TAT GGC CCG GGA GCT ACA ACA ATC TAT CCT GCT GCT GGG         816
Lys Tyr Thr Tyr Gly Pro Gly Ala Thr Thr Ile Tyr Pro Ala Ala Gly
235                  240                  245                  250

GGC TCT AAA GAC TGG GCT TAT GAC CAA GGA ATC AGA TAT TCC TTC ACC         864
Gly Ser Lys Asp Trp Ala Tyr Asp Gln Gly Ile Arg Tyr Ser Phe Thr
                255                  260                  265

TTT GAA CTT CGA GAT ACA GGC AGA TAT GGC TTT CTC CTT CCA GAA TCC         912
Phe Glu Leu Arg Asp Thr Gly Arg Tyr Gly Phe Leu Leu Pro Glu Ser
            270                  275                  280

CAG ATC CGG GCT ACC TGC GAG GAG ACC TTC CTG GCA ATC AAG TAT GTT         960
Gln Ile Arg Ala Thr Cys Glu Glu Thr Phe Leu Ala Ile Lys Tyr Val
        285                  290                  295

GCC AGC TAC GTC CTG GAA CAC CTG TAC CAC CAC CAT CAC CAC CAT GAG         1008
Ala Ser Tyr Val Leu Glu His Leu Tyr His His His His His His Glu
    300                  305                  310

TTC GAG GAG CAG AAG CTG ATC TCT GAG GAG GAC CTG AAC TAATAAGAAT         1057
Phe Glu Glu Gln Lys Leu Ile Ser Glu Glu Asp Leu Asn
315                  320                  325

TC                                                                      1059
```

(2) INFORMATION FOR SEQ ID NO: 60:

(i) SEQUENCE CHARACTERISTICS:
        (A) LENGTH: 349 amino acids
        (B) TYPE: amino acid
        (D) TOPOLOGY: linear (ii) MOLECULE TYPE: protein (xi) SEQUENCE DESCRIPTION: SEQ ID NO: 60:

```
Met Lys Tyr Leu Leu Pro Thr Ala Ala Ala Gly Leu Leu Leu Leu Ala
-22             -20                  -15                  -10

Ala Gln Pro Ala Met Ala Ala Thr Gly His Ser Tyr Glu Lys Tyr Asn
        -5                   1                   5                  10

Lys Trp Glu Thr Ile Glu Ala Trp Thr Gln Gln Val Ala Thr Glu Asn
                    15                  20                  25

Pro Ala Leu Ile Ser Arg Ser Val Ile Gly Thr Thr Phe Glu Gly Arg
                30                  35                  40
```

```
Ala Ile Tyr Leu Leu Lys Val Gly Lys Ala Gly Gln Asn Lys Pro Ala
        45                  50                  55
Ile Phe Met Asp Cys Gly Phe His Ala Arg Glu Trp Ile Ser Pro Ala
        60                  65                  70
Phe Cys Gln Trp Phe Val Arg Glu Ala Val Arg Thr Tyr Gly Arg Glu
    75                  80                  85                  90
Ile Gln Val Thr Glu Leu Leu Asp Lys Leu Asp Phe Tyr Val Leu Pro
                95                 100                 105
Val Leu Asn Ile Asp Gly Tyr Ile Tyr Thr Trp Thr Lys Ser Arg Phe
                110                 115                 120
Trp Arg Lys Thr Arg Ser Thr His Thr Gly Ser Ser Cys Ile Gly Thr
            125                 130                 135
Asp Pro Asn Arg Asn Phe Asp Ala Gly Trp Cys Glu Ile Gly Ala Ser
        140                 145                 150
Arg Asn Pro Cys Asp Glu Thr Tyr Cys Gly Pro Ala Ala Glu Ser Glu
155                 160                 165                 170
Lys Glu Thr Lys Ala Leu Ala Asp Phe Ile Arg Asn Lys Leu Ser Ser
            175                 180                 185
Ile Lys Ala Tyr Leu Thr Ile His Ser Tyr Ser Gln Met Met Ile Tyr
            190                 195                 200
Pro Tyr Ser Tyr Ala Tyr Lys Leu Gly Glu Asn Asn Ala Glu Leu Asn
        205                 210                 215
Ala Leu Ala Lys Ala Thr Val Lys Glu Leu Ala Ser Leu His Gly Thr
        220                 225                 230
Lys Tyr Thr Tyr Gly Pro Gly Ala Thr Thr Ile Tyr Pro Ala Ala Gly
235                 240                 245                 250
Gly Ser Lys Asp Trp Ala Tyr Asp Gln Gly Ile Arg Tyr Ser Phe Thr
            255                 260                 265
Phe Glu Leu Arg Asp Thr Gly Arg Tyr Gly Phe Leu Leu Pro Glu Ser
            270                 275                 280
Gln Ile Arg Ala Thr Cys Glu Glu Thr Phe Leu Ala Ile Lys Tyr Val
            285                 290                 295
Ala Ser Tyr Val Leu Glu His Leu Tyr His His His His His His Glu
300                 305                 310
Phe Glu Glu Gln Lys Leu Ile Ser Glu Glu Asp Leu Asn
315                 320                 325

(2) INFORMATION FOR SEQ ID NO: 61:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 61:

GGTCATAAGC CCAGTCGCGA GAGCC                                             25

(2) INFORMATION FOR SEQ ID NO: 62:

(i) SEQUENCE CHARACTERISTICS:
        (A) LENGTH: 27 base pairs
        (B) TYPE: nucleic acid
        (C) STRANDEDNESS: single
        (D) TOPOLOGY: linear
```

(ii) MOLECULE TYPE: other nucleic acid (xi) SEQUENCE DESCRIPTION: SEQ ID NO: 62:

CCTGCTGCTG GGGGCTCTCG CGACTGG                                          27

(2) INFORMATION FOR SEQ ID NO: 63:

(i) SEQUENCE CHARACTERISTICS:
        (A) LENGTH: 1059 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: CDS
        (B) LOCATION:1..1047

(ix) FEATURE:
        (A) NAME/KEY: mat_peptide
        (B) LOCATION:67..1047

(xi) SEQUENCE DESCRIPTION: SEQ ID NO: 63:

```
ATG AAA TAC CTA TTG CCT ACG GCA GCC GCT GGA TTG TTA TTA CTC GCT         48
Met Lys Tyr Leu Leu Pro Thr Ala Ala Ala Gly Leu Leu Leu Leu Ala
-22     -20             -15                 -10

GCC CAA CCA GCC ATG GCG GCA ACT GGT CAC TCT TAC GAG AAG TAC AAC         96
Ala Gln Pro Ala Met Ala Ala Thr Gly His Ser Tyr Glu Lys Tyr Asn
    -5              1               5                       10

AAG TGG GAA ACG ATA GAG GCT TGG ACT CAA CAA GTC GCC ACT GAG AAT        144
Lys Trp Glu Thr Ile Glu Ala Trp Thr Gln Gln Val Ala Thr Glu Asn
                15              20                  25

CCA GCC CTC ATC TCT CGC AGT GTT ATC GGA ACC ACA TTT GAG GGA CGC        192
Pro Ala Leu Ile Ser Arg Ser Val Ile Gly Thr Thr Phe Glu Gly Arg
            30              35                  40

GCT ATT TAC CTC CTG AAG GTT GGC AAA GCT GGA CAA AAT AAG CCT GCC        240
Ala Ile Tyr Leu Leu Lys Val Gly Lys Ala Gly Gln Asn Lys Pro Ala
        45              50                  55

ATT TTC ATG GAC TGT GGT TTC CAT GCC AGA GAG TGG ATT TCT CCT GCA        288
Ile Phe Met Asp Cys Gly Phe His Ala Arg Glu Trp Ile Ser Pro Ala
    60              65                  70

TTC TGC CAG TGG TTT GTA AGA GAG GCT GTT CGT ACC TAT GGA CGT GAG        336
Phe Cys Gln Trp Phe Val Arg Glu Ala Val Arg Thr Tyr Gly Arg Glu
75              80                  85                      90

ATC CAA GTG ACA GAG CTT CTC GAC AAG TTA GAC TTT TAT GTC CTG CCT        384
Ile Gln Val Thr Glu Leu Leu Asp Lys Leu Asp Phe Tyr Val Leu Pro
                95                  100                 105

GTG CTC AAT ATT GAT GGC TAC ATC TAC ACC TGG ACC AAG AGC CGA TTT        432
Val Leu Asn Ile Asp Gly Tyr Ile Tyr Thr Trp Thr Lys Ser Arg Phe
            110                 115                 120

TGG AGA AAG ACT CGC TCC ACC CAT ACT GGA TCT AGC TGC ATT GGC ACA        480
Trp Arg Lys Thr Arg Ser Thr His Thr Gly Ser Ser Cys Ile Gly Thr
        125                 130                 135

GAC CCC AAC AGA AAT TTT GAT GCT GGT TGG TGT GAA ATT GGA GCC TCT        528
Asp Pro Asn Arg Asn Phe Asp Ala Gly Trp Cys Glu Ile Gly Ala Ser
    140                 145                 150

CGA AAC CCC TGT GAT GAA ACT TAC TGT GGA CCT GCC GCA GAG TCT GAA        576
Arg Asn Pro Cys Asp Glu Thr Tyr Cys Gly Pro Ala Ala Glu Ser Glu
155                 160                 165                 170

AAG GAG ACC AAG GCC CTG GCT GAT TTC ATC CGC AAC AAA CTC TCT TCC        624
Lys Glu Thr Lys Ala Leu Ala Asp Phe Ile Arg Asn Lys Leu Ser Ser
                175                 180                 185
```

```
ATC AAG GCA TAT CTG ACA ATC CAC TCG TAC TCC CAA ATG ATG ATC TAC        672
Ile Lys Ala Tyr Leu Thr Ile His Ser Tyr Ser Gln Met Met Ile Tyr
        190                 195                 200

CCT TAC TCA TAT GCT TAC AAA CTC GGT GAG AAC AAT GCT GAG TTG AAT        720
Pro Tyr Ser Tyr Ala Tyr Lys Leu Gly Glu Asn Asn Ala Glu Leu Asn
            205                 210                 215

GCC CTG GCT AAA GCT ACT GTG AAA GAA CTT GCC TCA CTG CAC GGC ACC        768
Ala Leu Ala Lys Ala Thr Val Lys Glu Leu Ala Ser Leu His Gly Thr
    220                 225                 230

AAG TAC ACA TAT GGC CCG GGA GCT ACA ACA ATC TAT CCT GCT GCT GGG        816
Lys Tyr Thr Tyr Gly Pro Gly Ala Thr Thr Ile Tyr Pro Ala Ala Gly
235                 240                 245                 250

GGC TCT CGC GAC TGG GCT TAT GAC CAA GGA ATC AGA TAT TCC TTC ACC        864
Gly Ser Arg Asp Trp Ala Tyr Asp Gln Gly Ile Arg Tyr Ser Phe Thr
                255                 260                 265

TTT GAA CTT CGA GAT ACA GGC AGA TAT GGC TTT CTC CTT CCA GAA TCC        912
Phe Glu Leu Arg Asp Thr Gly Arg Tyr Gly Phe Leu Leu Pro Glu Ser
            270                 275                 280

CAG ATC CGG GCT ACC TGC GAG GAG ACC TTC CTG GCA ATC AAG TAT GTT        960
Gln Ile Arg Ala Thr Cys Glu Glu Thr Phe Leu Ala Ile Lys Tyr Val
    285                 290                 295

GCC AGC TAC GTC CTG GAA CAC CTG TAC CAC CAC CAT CAC CAC CAT GAG       1008
Ala Ser Tyr Val Leu Glu His Leu Tyr His His His His His His Glu
300                 305                 310

TTC GAG GAG CAG AAG CTG ATC TCT GAG GAG GAC CTG AAC TAATAAGAAT       1057
Phe Glu Glu Gln Lys Leu Ile Ser Glu Glu Asp Leu Asn
315                 320                 325

TC                                                                   1059

(2) INFORMATION FOR SEQ ID NO: 64:

(i) SEQUENCE CHARACTERISTICS:
        (A) LENGTH: 349 amino acids
        (B) TYPE: amino acid
        (D) TOPOLOGY: linear (ii) MOLECULE TYPE: protein (xi) SEQUENCE DESCRIPTION: SEQ ID NO: 64:

Met Lys Tyr Leu Leu Pro Thr Ala Ala Ala Gly Leu Leu Leu Leu Ala
-22         -20                 -15                 -10

Ala Gln Pro Ala Met Ala Ala Thr Gly His Ser Tyr Glu Lys Tyr Asn
    -5                  1                   5                   10

Lys Trp Glu Thr Ile Glu Ala Trp Thr Gln Val Ala Thr Glu Asn
                15                  20                  25

Pro Ala Leu Ile Ser Arg Ser Val Ile Gly Thr Thr Phe Glu Gly Arg
                30                  35                  40

Ala Ile Tyr Leu Leu Lys Val Gly Lys Ala Gly Gln Asn Lys Pro Ala
        45                  50                  55

Ile Phe Met Asp Cys Gly Phe His Ala Arg Glu Trp Ile Ser Pro Ala
        60                  65                  70

Phe Cys Gln Trp Phe Val Arg Glu Ala Val Arg Thr Tyr Gly Arg Glu
75                  80                  85                  90

Ile Gln Val Thr Glu Leu Leu Asp Lys Leu Asp Phe Tyr Val Leu Pro
                95                  100                 105

Val Leu Asn Ile Asp Gly Tyr Ile Tyr Thr Trp Thr Lys Ser Arg Phe
                110                 115                 120

Trp Arg Lys Thr Arg Ser Thr His Thr Gly Ser Ser Cys Ile Gly Thr
        125                 130                 135
```

```
Asp Pro Asn Arg Asn Phe Asp Ala Gly Trp Cys Glu Ile Gly Ala Ser
    140                 145                 150
Arg Asn Pro Cys Asp Glu Thr Tyr Cys Gly Pro Ala Ala Glu Ser Glu
155                 160                 165                 170
Lys Glu Thr Lys Ala Leu Ala Asp Phe Ile Arg Asn Lys Leu Ser Ser
                175                 180                 185
Ile Lys Ala Tyr Leu Thr Ile His Ser Tyr Ser Gln Met Met Ile Tyr
                190                 195                 200
Pro Tyr Ser Tyr Ala Tyr Lys Leu Gly Glu Asn Asn Ala Glu Leu Asn
            205                 210                 215
Ala Leu Ala Lys Ala Thr Val Lys Glu Leu Ala Ser Leu His Gly Thr
    220                 225                 230
Lys Tyr Thr Tyr Gly Pro Gly Ala Thr Thr Ile Tyr Pro Ala Ala Gly
235                 240                 245                 250
Gly Ser Arg Asp Trp Ala Tyr Asp Gln Gly Ile Arg Tyr Ser Phe Thr
                255                 260                 265
Phe Glu Leu Arg Asp Thr Gly Arg Tyr Gly Phe Leu Leu Pro Glu Ser
                270                 275                 280
Gln Ile Arg Ala Thr Cys Glu Glu Thr Phe Leu Ala Ile Lys Tyr Val
                285                 290                 295
Ala Ser Tyr Val Leu Glu His Leu Tyr His His His His His His Glu
    300                 305                 310
Phe Glu Glu Gln Lys Leu Ile Ser Glu Glu Asp Leu Asn
315                 320                 325

(2) INFORMATION FOR SEQ ID NO: 65:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 65:

GGATTTGGGG GAGGAACCTG GCTTCTGCTG                                         30

(2) INFORMATION FOR SEQ ID NO: 66:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 66:

Ala Pro Pro Val Ala Gly Pro Ser
1               5

(2) INFORMATION FOR SEQ ID NO: 67:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide
```

(xi) SEQUENCE DESCRIPTION: SEQ ID NO: 67:

Val Pro Glu Val Ser Ser Val Phe
1               5

(2) INFORMATION FOR SEQ ID NO: 68:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 68:

GCAGCAGGAT AGATTGTTGT AGC                                           23

(2) INFORMATION FOR SEQ ID NO: 69:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 69:

CAATCTATCC TGCTGCTGGG AACTCTCGCG                                    30

(2) INFORMATION FOR SEQ ID NO: 70:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 70:

GGTCATAAGC CCAGTCTTTA GAGTTCCCAG                                    30

(2) INFORMATION FOR SEQ ID NO: 71:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 71:

CTATCCTGCT GCTGGGAACT CTAAAGACTG                                    30

(2) INFORMATION FOR SEQ ID NO: 72:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 72:

CAATCTATCC TGCTGCTGGG ACTTCTAAAG                                    30

(2) INFORMATION FOR SEQ ID NO: 73:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 73:

GGAATCAGAT ATTCCTTCGG CTTTGAAC                  28

(2) INFORMATION FOR SEQ ID NO: 74:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 74:

GGAATATCTG ATTCCTTGGT C                           21

(2) INFORMATION FOR SEQ ID NO: 75:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 75:

CAATCTATCC TGCTGCTGGG TCTTCTAAAG                 30

(2) INFORMATION FOR SEQ ID NO: 76:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 76:

GATTGTTGTA GCTCCCGGGC                            20

(2) INFORMATION FOR SEQ ID NO: 77:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 77:

GGAGCTACAA CAATCTATCC TAACGCTGGG                 30

(2) INFORMATION FOR SEQ ID NO: 78:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: other nucleic acid (xi) SEQUENCE DESCRIPTION: SEQ ID NO: 78:

GGAGCTACAA CAATCTATCC TTTCGCTGGG                                30

(2) INFORMATION FOR SEQ ID NO: 79:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 79:

GGGTAGATCA TCATTTGGGA GTACG                                     25

(2) INFORMATION FOR SEQ ID NO: 80:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 80:

CCAAATGATG ATCTACCCTT ACAACTATGC                                30

(2) INFORMATION FOR SEQ ID NO: 81:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 81:

CAATCTATCC TGCTGCTGGG ACTTCTCGCG                                30

(2) INFORMATION FOR SEQ ID NO: 82:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 82:

CATTTGGGAG TACGAGTGGA TTG                                       23

(2) INFORMATION FOR SEQ ID NO: 83:

(i) SEQUENCE CHARACTERISTICS:
        (A) LENGTH: 25 base pairs
        (B) TYPE: nucleic acid
        (C) STRANDEDNESS: single (D) TOPOLOGY: linear (ii) MOLECULE TYPE: other nucleic acid (xi) SEQUENCE DESCRIPTION: SEQ ID NO: 83:

CGTACTCCCA AATGATGACT TACCC                                    25

(2) INFORMATION FOR SEQ ID NO: 84:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO: 84:

Gly Ser Ser Ile Gly
 1               5

(2) INFORMATION FOR SEQ ID NO: 85:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO: 85:

Gly Ser Ser Cys Ile Gly
 1               5

(2) INFORMATION FOR SEQ ID NO: 86:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 86:

Glu Gln Lys Leu Ile Ser Glu Glu Asp Leu
 1               5                  10

(2) INFORMATION FOR SEQ ID NO: 87:

(i) SEQUENCE CHARACTERISTICS:
        (A) LENGTH: 360 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: CDS
        (B) LOCATION:118..237

(xi) SEQUENCE DESCRIPTION: SEQ ID NO: 87:

TCACACTTTG CAAAGCATTA GCATTTTTGT CCATAAGATA AGCGGATCCT GCCTGACGGT    60

TTTTGCCGCG ACTCTCTACT GTTTCTCCAT ACCTGTTTTT CTGGATGGAG TAAGACC     117

ATG AAA TAC CTA TTG CCT ACG GCA GCC GCT GGA TTG TTA TTA CTC GCT    165
Met Lys Tyr Leu Leu Pro Thr Ala Ala Ala Gly Leu Leu Leu Leu Ala
 1               5                  10                  15

-continued

```
GCC CAA CCA GCC ATG GCG GTA CCA ATA GCA GAT CTA ATG TCT CTA GAT        213
Ala Gln Pro Ala Met Ala Val Pro Ile Ala Asp Leu Met Ser Leu Asp
         20              Ala Val Pro Ile Ala Asp Leu Met Ser Leu Asp
                                    25                  30

GTT ACC TCG AGT TCG AAG AAT TCC TAG AGTCGACATT ATATTACTAA              260
Val Thr Ser Ser Ser Lys Asn Ser
         35                 40

TTAATTGGGG ACCCTAGAGG TCCCCTTTTT TATTTTAAAA AGCATGCGGA TCCGTCGGAA      320

ATACAGGAAC GCACGCTGGA TGGCCCTTCG CTGGGATGGT                            360
```